US012741940B2

(12) United States Patent
Savall et al.

(10) Patent No.: US 12,741,940 B2
(45) Date of Patent: Sep. 22, 2026

(54) DOPAMINE RECEPTOR D1 AGONISTS AND METHODS OF USE

(71) Applicants: Sanford Burnham Prebys Medical Discovery Institute, La Jolla, CA (US); Mayo Foundation for Medical Education and Research, Rochester, MN (US)

(72) Inventors: Brad Savall, San Diego, CA (US); Andrew J. Haak, Rochester, MN (US); Daniel J. Tschumperlin, Rochester, MN (US)

(73) Assignees: Sanford Burnham Prebys Medical Discovery Institute, La Jolla, CA (US); Mayo Foundation for Medical Education and Research, Rochester, MN (US)

( * ) Notice: Subject to any disclaimer, the term of this patent is extended or adjusted under 35 U.S.C. 154(b) by 390 days.

(21) Appl. No.: 17/628,875

(22) PCT Filed: Jul. 29, 2020

(86) PCT No.: PCT/US2020/044099
§ 371 (c)(1),
(2) Date: Jan. 20, 2022

(87) PCT Pub. No.: WO2021/021953
PCT Pub. Date: Feb. 4, 2021

(65) Prior Publication Data

US 2022/0267277 A1 Aug. 25, 2022

Related U.S. Application Data

(60) Provisional application No. 62/880,604, filed on Jul. 30, 2019.

(51) Int. Cl.

| | |
|---|---|
| ***C07D 221/18*** | (2006.01) |
| ***A61K 9/00*** | (2006.01) |
| ***A61K 9/20*** | (2006.01) |
| ***A61K 9/48*** | (2006.01) |
| ***A61P 19/04*** | (2006.01) |
| ***C07D 471/04*** | (2006.01) |

(52) U.S. Cl.
CPC .......... *C07D 221/18* (2013.01); *A61K 9/0019* (2013.01); *A61K 9/0053* (2013.01); *A61K 9/2054* (2013.01); *A61K 9/4825* (2013.01); *A61P 19/04* (2018.01); *C07D 471/04* (2013.01)

(58) Field of Classification Search
None
See application file for complete search history.

(56) References Cited

U.S. PATENT DOCUMENTS

| | | | |
|---|---|---|---|
| 4,315,938 | A | 2/1982 | Schneider et al. |
| 2011/0190332 | A1 | 8/2011 | Mailman |

FOREIGN PATENT DOCUMENTS

| | | | |
|---|---|---|---|
| WO | WO-9602513 | A1 | 2/1996 |
| WO | WO-9736902 | A1 | 10/1997 |
| WO | WO-2019028059 | A1 | 2/2019 |
| WO | WO-2019104038 | A1 | 5/2019 |
| WO | WO-2019152733 | A1 | 8/2019 |
| WO | WO-2021021953 | A2 | 2/2021 |

OTHER PUBLICATIONS

Gu et al. "trans-2,6-, 3,6- and 4,6-Diaza-5,6,6a,7,8, 12b-hexahydrobenzo[C]phenanthrene-10,11-diols as dopamine agonists" Bioorganic & Medicinal Chemistry Letters 9 (1999) 1341-1346 (Year: 1999).*
Cho. Recent Advances in Oral Prodrug Discovery. Annual Reports in Medicinal Chemistry 41:395-407 (2006).
Nogrady. Chapter 4: Pro Drugs and Soft Drugs. In: Medicinal Chemistry: A Biochemical approach. New York: Oxford University Press, p. 388-392 (1985).
PCT/US2020/044099 International Invitation to Pay Additional Fees dated Sep. 24, 2020.
PCT/US2020/044099 International Search Report and Written Opinion dated Feb. 12, 2021.
PubChem Substance ID No. 349296614.
Rooseboom et al. Enzyme-catalyzed activation of anticancer prodrugs. Pharmacological Reviews 56:53-102 (2004).
Silverman et al. Chapter 8: Prodrugs and drug delivery systems. In: The Organic Chemistry of Drug Design and Drug Action. San Diego: Academic Press, Inc. p. 352-401 (1992).
Knoerzer et al. Synthesis and biological evaluation of a series of substituted benzo[a]phenanthridines as agonists at D1 and D2 dopamine receptors. J Med Chem 38(16):3062-70 (1995).

* cited by examiner

*Primary Examiner* — Adam C Milligan
*Assistant Examiner* — Jed A Kucharczk
(74) *Attorney, Agent, or Firm* — WILSON SONSINI GOODRICH & ROSATI

(57) ABSTRACT

Described herein are small molecule agonists of dopamine receptor D1 that inhibit YAP/TAZ, compositions, and methods of using these compounds and compositions. The methods of using such compounds in the treatment of conditions, diseases, or disorders associated with fibrotic disease are described herein.

14 Claims, 2 Drawing Sheets

Alveolar Epithelial Cells
Lung Fibroblasts

DOPAMINE RECEPTOR D1 AGONISTS AND METHODS OF USE

CROSS REFERENCE

This application is the U.S. National Stage application of International Application No. PCT/US2020/044099, filed on Jul. 29, 2020, and claims the benefit of U.S. Provisional Application No. 62/880,604, filed on Jul. 30, 2019, all of which are incorporated herein by reference in their entirety.

FIELD OF THE INVENTION

The present invention generally relates to compounds that inhibit YAP/TAZ in fibroblasts, methods of making such compounds, pharmaceutical compositions and medicaments comprising such compounds, and methods of using such compounds in the treatment of conditions, diseases, or disorders associated with fibrotic disease.

BACKGROUND OF THE INVENTION

Fibrotic diseases, including tissue fibrosis across all organs, affects a vast population of people. In the U.S. alone, over half a million people are affected by liver and lung fibrosis. These diseases remain very challenging to treat clinically. In examples such as idiopathic pulmonary fibrosis (IPF) and scleroderma, therapeutic options are extremely limited. In fact, for this group of diseases, the five-year survival rate can be as bleak as many late stage aggressive cancers.

BRIEF SUMMARY OF THE INVENTION

Described herein are small molecule agonists of dopamine receptor D1 that inhibit YAP/TAZ. In one aspect described herein, is a compound having there structure of Formula (I), or a pharmaceutically acceptable salt or solvate thereof:

Formula (I)

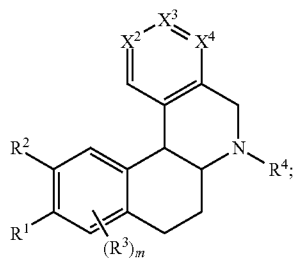

wherein:

- $X^2$ is N or $CR^5$;
- $X^3$ is N or $CR^6$;
- $X^4$ is N or $CR^7$;
- or $X^1$ and $X^2$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$;
- or $X^2$ and $X^3$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$;
- or $X^3$ and $X^4$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$;
- m is 0, 1, or 2;
- each $R^1$ and $R^2$ is independently hydrogen, halogen, —CN, —OH, —$OR^a$, —SH, —$SR^a$, —S(═O)$R^a$, —$NO_2$, —$N(R^b)_2$, —$S(═O)_2R^a$, —$NHS(═O)_2R^a$, —$S(═O)_2N(R^b)_2$, —C(═O)$R^a$, —OC(═O)$R^a$, —C(═O)$OR^b$, —OC(═O)OR, —C(═O)$N(R^b)_2$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;
- or $R^1$ and $R^2$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;
- $R^3$ is hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;
- $R^4$ is hydrogen or $C_1$-$C_6$ alkyl;
- each $R^5$, $R^6$, and $R^7$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;
- or $R^5$ and $R^6$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;
- or $R^6$ and $R^7$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;
- each $R^8$ is independently halogen, —CN, —OH, —$OR^a$, —$N(R^b)_2$, —$S(═O)_2R^a$, —$NHS(═O)_2R^a$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl;
- each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, the compound having the structure of Formula (I), has the structure of Formula (II), or a pharmaceutically acceptable salt or solvate thereof:

Formula (II)

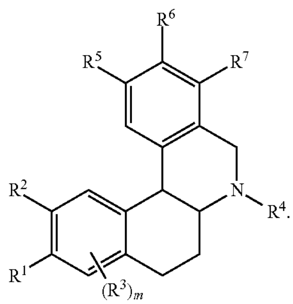

In some embodiments, the compound having the structure of Formula (I), has the structure of Formula (III-2), or a pharmaceutically acceptable salt or solvate the thereof:

Formula (III-2)

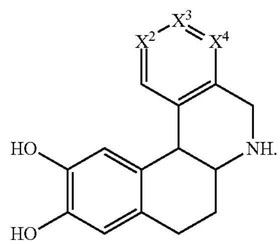

In some embodiments, the compound having the structure of Formula (I), has the structure of Formula (IIIa), (IIIb), or (IIIc), or a pharmaceutically acceptable salt or solvate the thereof:

Formula (IIIa)

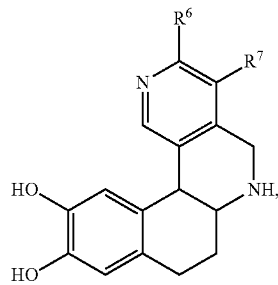

Formula (IIIb)

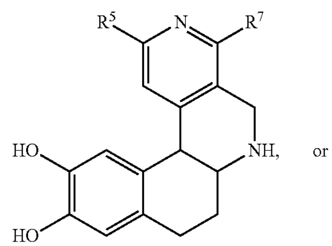

or

Formula (IIIc)

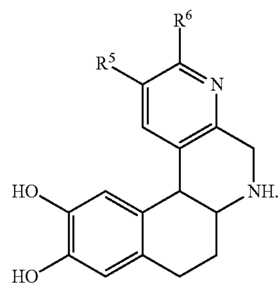

In some embodiments, the compound having the structure of Formula (I), has the structure of Formula (IV), or a pharmaceutically acceptable salt or solvate the thereof:

Formula (IV)

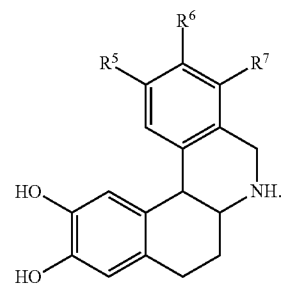

In another aspect described herein, is a compound having there structure of Formula (V), or a pharmaceutically acceptable salt or solvate thereof:

Formula (V)

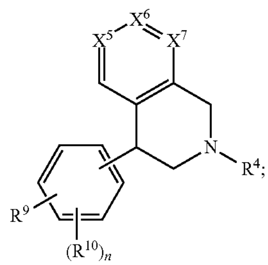

wherein:

$X^5$ is N or $CR^{11}$;

$X^6$ is N or $CR^{12}$;

$X^7$ is N or $CR^{13}$;

or $X^5$ and $X^6$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^{14}$;

or $X^6$ and $X^7$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^{14}$;

n is 0, 1, or 2;

$R^4$ is hydrogen or $C_1$-$C_6$ alkyl;

each $R^9$ and $R^{10}$ is independently hydrogen, halogen, —CN, —OH, —OR, —SH, —$SR^a$, —S(═O)$R^a$, —$NO_2$, —$N(R^b)_2$, —S(═O)$_2R^a$, —NHS(═O)$_2R^a$, —S(═O)$_2N(R^b)_2$, —C(═O)$R^a$, —OC(═O)$R^a$, —C(═O)$OR^b$, —OC(═O)$OR^b$, —C(═O)$N(R^b)_2$, —OC(═O)$N(R^b)_2$, —$NR^b$C(═O)$N(R^b)_2$, —$NR^b$C(═O)$R^a$, —$NR^b$C(═O)$OR^b$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$;

or $R^9$ and $R^{10}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{14}$;

each $R^{11}$, $R^{12}$, and $R^{13}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl, and $C_1$-$C_6$ heteroalkyl is unsubstituted or substituted with one, two, or three $R^{14}$;

each $R^{14}$ is independently halogen, —CN, —OH, —$OR^a$, —$N(R^b)_2$, —S(═O)$_2R^a$, —NHS(═O)$_2R^a$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, the compound having the structure of Formula (V) has the structure of Formula (VI), or a pharmaceutically acceptable salt or solvate thereof:

Formula (VI)

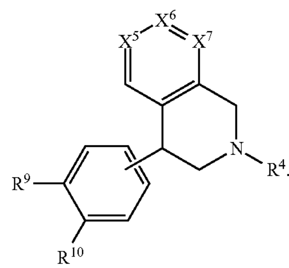

In some embodiments, the compound having the structure of Formula (VI) has the structure of Formula (VIIa) or (VIIb), or a pharmaceutically acceptable salt or solvate thereof:

Formula (VIIa)

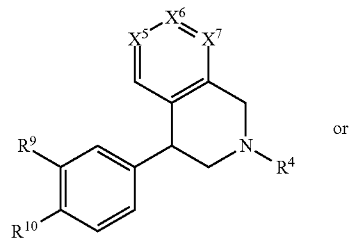

or

Formula (VIIb)

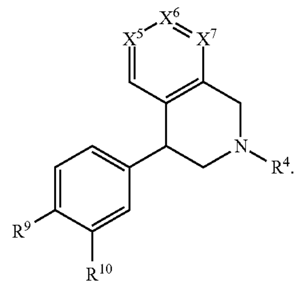

In some embodiments, the compound having the structure of Formula (VI) has the structure of Formula (VIIIa), (VIIIb), or (VIIIc), or a pharmaceutically acceptable salt or solvate thereof:

Formula (VIIIa)

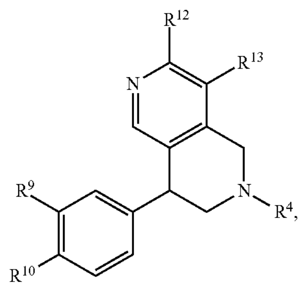

Formula (VIIIb)

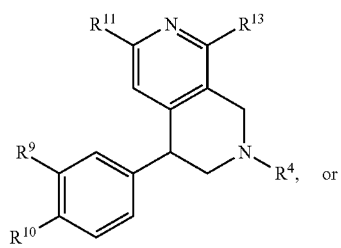

or

Formula (VIIIc)

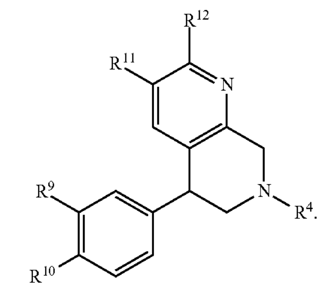

In another aspect described herein, is a compound having there structure of Formula (IX), or a pharmaceutically acceptable salt or solvate thereof:

Formula (IX)

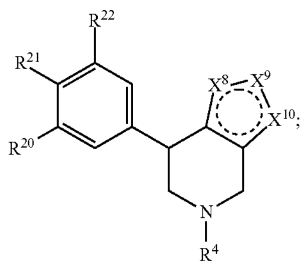

wherein:

$X^8$ is N, O, S, or $CR^{15}$;

$X^9$ is N, O, S, or $CR^{16}$;

$X^{10}$ is N, O, S, or $CR^{17}$;

provided that only one of $X^8$, $X^9$, and $X^{10}$ is O or S;

$R^4$ is hydrogen or $C_1$-$C_6$ alkyl;

each $R^{15}$, $R^{16}$, and $R^{17}$ is independently hydrogen, halogen, —CN, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$;

each $R^{20}$, $R^{21}$, and $R^{22}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{19}$;

or $R^{20}$ and $R^{21}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{19}$;

or $R^{21}$ and $R^{22}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{19}$;

each $R^{18}$ and $R^{19}$ is independently halogen, —CN, —OH, —$OR^a$, —$N(R^b)_2$, —$S(=O)_2R^a$, —$NHS(=O)_2R^a$, —$OC(=O)N(R^b)_2$, —$NR^bC(=O)N(R^b)_2$, —$NR^bC(=O)R^a$, —$NR^bC(=O)OR$, $C_1$-$C_6$ alkyl, $C_1$-$C_6$ haloalkyl, $C_1$-$C_6$ hydroxyalkyl, $C_1$-$C_6$ heteroalkyl, or cycloalkyl which is unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, the compound having the structure of Formula (IX) has the structure of Formula (X), or a pharmaceutically acceptable salt or solvate thereof:

Formula (X)

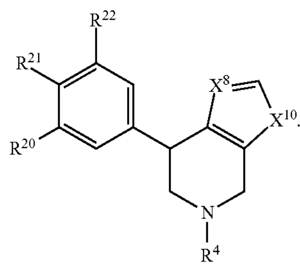

In some embodiments, the compound having the structure of Formula (X) has the structure of Formula (Xa) or (Xb), or a pharmaceutically acceptable salt or solvate thereof:

Formula (Xa)

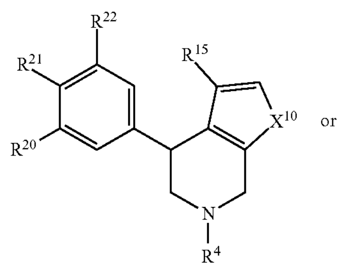

or

Formula (Xb)

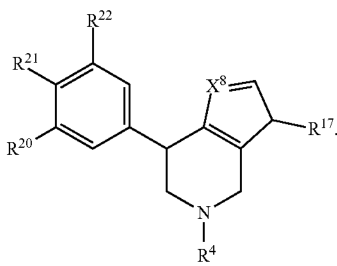

In some embodiments, the compound having the structure of Formula (X) has the structure of Formula (Xa-1), or a pharmaceutically acceptable salt or solvate thereof:

Formula (Xa-1)

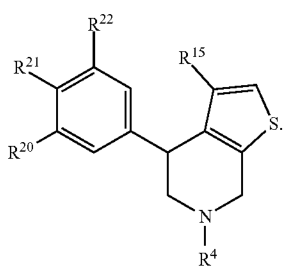

Any combination of the groups described above for the various variables is contemplated herein. Throughout the specification, groups and substituents thereof are chosen by one skilled in the field to provide stable moieties and compounds.

In another aspect provided herein, is a pharmaceutical composition comprising a compound disclosed herein, or a pharmaceutically acceptable salt, or solvate thereof, and at least one pharmaceutically acceptable excipient. In some embodiments, the compound disclosed herein, or a pharmaceutically acceptable salt thereof, is formulated for administration to a mammal by intravenous administration, subcutaneous administration, oral administration, inhalation, nasal administration, dermal administration, or ophthalmic administration. In some embodiments, the compound disclosed herein, or a pharmaceutically acceptable salt thereof, is in the form of a tablet, a pill, a capsule, a liquid, a suspension, a gel, a dispersion, a solution, an emulsion, an ointment, or a lotion.

In another embodiment described herein, is a method of treating a disease or condition in a mammal that would benefit by inhibition of YAP/TAZ, the method comprising administering to the mammal a therapeutically effective amount of a compound as described herein, or a pharmaceutically acceptable salt or solvate thereof.

In another embodiment provided herein, is a method of treating or preventing a fibrotic pathology, the method comprising administering to a mammal in need thereof a therapeutically effective amount the mammal a compound as described herein, or a pharmaceutically acceptable salt or solvate thereof. In some embodiments, the fibrotic pathology is interstitial lung disease (ILD). In some embodiments, the fibrotic pathology is selected from pulmonary fibrosis (PF) and idiopathic pulmonary fibrosis (IPF). In some embodiments, the fibrotic pathology is selected from liver tissue fibrosis, cardiac fibrosis, kidney fibrosis, and skin tissue fibrosis.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION

Figure 1:
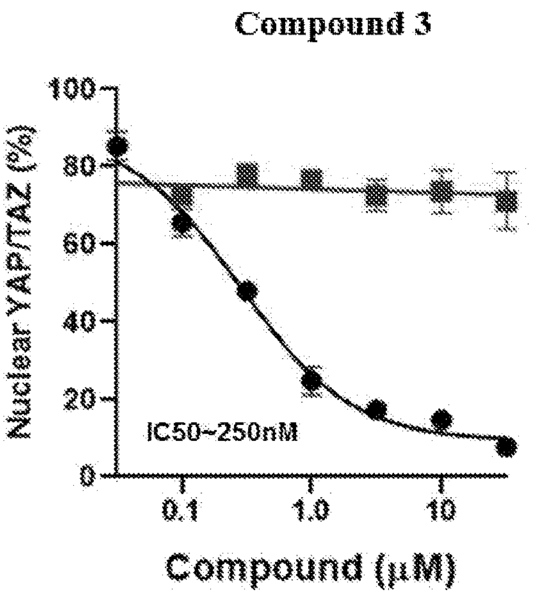
FIG. 1 demonstrates that Compound 3 (left) and Compound 4a (right) selectively inhibit YAP/TAZ nuclear localization in human lung fibroblasts and not in human alveolar epithelial cells.
Figure 1:
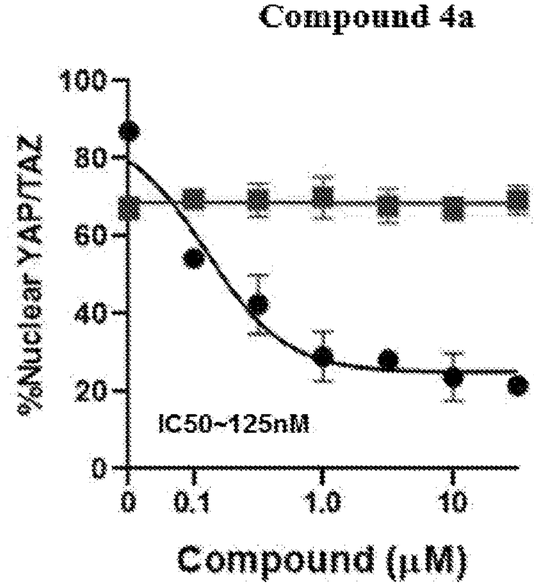

Idiopathic Pulmonary Fibrosis (IPF) has a prevalence of ~18 cases per 100,000 individuals in the United States, and accounts for ~40-80,000 deaths annually in the U.S. and Europe. IPF is rapidly progressive, with a median survival of 2.5-3.5 years. Despite the prevalence and severity of this disease, only two FDA approved therapies are available (Pirfenidone and Nintedanib), and both show only modest benefits in patient symptoms and quality of life. Importantly, neither has been shown to definitively prolong life expectancy or improve lung function. Beyond IPF, fibrosis is associated with the pathologies responsible for ~40% of all deaths from chronic disease, with prominent roles in kidney, liver, and cardiovascular disease, as well as systemic sclerosis, all of which currently lack FDA approved therapies that target organ fibrosis. Both FDA approved therapies available (Pirfenidone and Nintedanib) for IPF show only modest benefits in patient symptoms and quality of life. Importantly, neither has been shown to definitively prolong life expectancy or improve lung function.

Tissue fibrosis can occur in multiple vital organs including heart, lung, liver, and kidney. Fibrosis is a progressive process which, through multiple mechanisms, transforms a normal healthy organ into an architecturally and functionally compromised tissue. From a clinical standpoint they represent a serious problem as the therapeutic options remain minimal and the prognosis is generally very poor. Dopamine receptors, which are almost exclusively researched as part of the central nervous system, are actually highly expressed in the periphery as well in select tissues and cells in the body.

These receptors signal through downstream pathways which play a major role in tissue fibrosis. The present work shows that a Gas-coupled receptor, such as a dopamine receptor D1 (DRD1), as a viable therapeutic target for the treatment or prevention of tissue fibrosis in multiple organs. Dopamine receptor D1, also known as DRD1, is a protein that in humans is encoded by the DRD1 gene. Based upon Northern blot and in situ hybridization, DRD1 mRNA expression in the central nervous system is highest in the dorsal striatum (caudate and putamen) and ventral striatum (nucleus accumbens and olfactory tubercle). Lower levels of DRD1 mRNA expression occur in the basolateral amygdala, cerebral cortex, septum, thalamus, and hypothalamus.

YAP and TAZ are transcriptional co-activators and central effectors of the Hippo pathway. Originally identified based on their roles in organ growth and size control during tissue morphogenesis, the Hippo pathway and YAP/TAZ in adult tissues regulate epithelial and endothelial homeostasis, stem cell function and tissue regeneration. An array of mechanical and biochemical signals have been implicated as upstream regulators of YAP and TAZ, with multiple pro-fibrotic stimuli including matrix stiffness, TGFβ/SMAD, MRTF/SRF, and WNT signaling all potentially involved.

G protein coupled receptors are linked to effector proteins from four main classes of G-proteins (e.g., Gα12/13, Gαq/11, Gαi/o or Gas). In some instances, G protein coupled receptor stimulates YAP/TAZ nuclear translocation and transcriptional activity. In other instances, G protein coupled receptors inhibit YAP/TAZ nuclear localization and activity via elevation of cAMP. In some embodiments, activation (agonism) of a G protein coupled receptor results in YAP/TAZ hyper phosphorylation and inactivation under physiological conditions (e.g., agonism of the receptor prevents YAP/TAZ nuclear localization). This is in contrast to inactivation (antagonism) of G protein coupled receptor, which stimulates YAP/TAZ nuclear translocation and transcriptional activity, which results in expression of profibrotic genes, such as Acta2 (aSMA), Ctgf (Connective tissue growth factor), Fn1 (Fibronectin), Col1a1 (Collagen I), and Col1a2 (Collagen II).

In some embodiments, the present disclosure provides a method of agonizing a G protein coupled receptor in a cell, the method comprising contacting the cell with any one of compounds described herein, or a pharmaceutically acceptable salt thereof. In some embodiments, the present disclosure provides a method of promoting YAP phosphorylation in a cell, the method comprising contacting the cell with any one of compounds described herein, or a pharmaceutically acceptable salt thereof.

Compounds

Described herein are small molecule agonists of dopamine receptor D1 that inhibit YAP/TAZ. In one aspect, described herein is a compound of Formula (Ia), or a pharmaceutically acceptable salt or solvate thereof:

Formula (Ia)

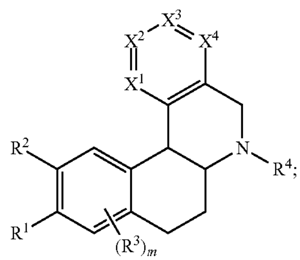

wherein:

$X^1$ is N or $CR^{24}$;

$X^2$ is N or $CR^5$;

$X^3$ is N or $CR^6$;

$X^4$ is N or $CR^7$;

or $X^1$ and $X^2$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$;

or $X^2$ and $X^3$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$;

or $X^3$ and $X^4$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$;

m is 0, 1, or 2;

each $R^1$ and $R^2$ is independently hydrogen, halogen, —CN, —OH, $—OR^a$, —SH, $—SR^a$, $—S(=O)R^a$, $—NO_2$, $—N(R^b)_2$, $—S(=O)_2R^a$, $—NHS(=O)_2R^a$, $—S(=O)_2N(R^b)_2$, $—C(=O)R^a$, $—OC(=O)R^a$, $—C(=O)OR^b$, —OC(=O)OR, $—C(=O)N(R^b)_2$, $—OC(=O)N(R^b)_2$, $—NR^bC(=O)N(R^b)_2$, $—NR^bC(=O)R^a$, $—NR^bC(=O)OR$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

or $R^1$ and $R^2$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

$R^3$ is hydrogen, halogen, —CN, —OH, $—OR^a$, —SH, $—SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

$R^4$ is hydrogen or $C_1$-$C_6$ alkyl;

each $R^5$, $R^6$, $R^7$, and $R^{24}$ is independently hydrogen, halogen, —CN, —OH, $—OR^a$, —SH, $—SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

or $R^5$ and $R^6$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

or $R^6$ and $R^7$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

or $R^5$ and $R^{24}$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

each $R^8$ is independently halogen, —CN, —OH, —$OR^a$, —$N(R^b)_2$, —$S(=O)_2R^a$, —$NHS(=O)_2R^a$, —$OC(=O)N(R^b)_2$, —$NR^bC(=O)N(R^b)_2$, —$NR^bC(=O)R^a$, —$NR^bC(=O)OR$, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In another aspect described herein, is a compound of Formula (I), or a pharmaceutically acceptable salt or solvate thereof:

Formula (I)

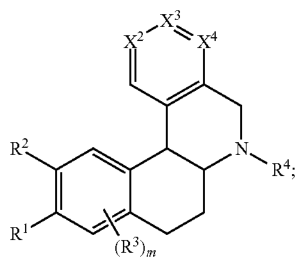

wherein:

$X^2$ is N or $CR^5$;

$X^3$ is N or $CR^6$;

$X^4$ is N or $CR^7$;

m is 0, 1, or 2;

each $R^1$ and $R^2$ is independently hydrogen, halogen, —CN, —OH, —$OR^a$, —SH, —$SR^a$, —$S(=O)R^a$, —$NO_2$, —$N(R^b)_2$, —$S(=O)_2R^a$, —$NHS(=O)_2R^a$, —$S(=O)_2N(R^b)_2$, —$C(=O)R^a$, —$OC(=O)R^a$, —$C(=O)OR^b$, —$OC(=O)OR$, —$C(=O)N(R^b)_2$, —$OC(=O)N(R^b)_2$, —$NR^bC(=O)N(R^b)_2$, —$NR^bC(=O)R^a$, —$NR^bC(=O)OR$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

or $R^1$ and $R^2$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

$R^3$ is hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

$R^4$ is hydrogen or $C_1$-$C_6$ alkyl;

each $R^5$, $R^6$, and $R^7$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

or $R^5$ and $R^6$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

or $R^6$ and $R^7$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

each $R^8$ is independently halogen, —CN, —OH, —$OR^a$, —$N(R^b)_2$, —$S(=O)_2R^a$, —$NHS(=O)_2R^a$, —$OC(=O)N(R^b)_2$, —$NR^bC(=O)N(R^b)_2$, —$NR^bC(=O)R^a$, —$NR^bC(=O)OR$, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, the compound having the structure of Formula (I) or (Ia) is not (6aS,12bR)-2-methyl-5,6,6a,7, 8,12b-hexahydrobenzo[a]phenanthridine-3,10,11-triol. In some embodiments, when $R^1$ and $R^2$ are —OH; $R^4$ is hydrogen; $R^5$ is $C_1$-$C_6$ alkyl; and $R^6$ is OH; then $R^7$ is not hydrogen. In some embodiments, when $R^1$ and $R^2$ are —OH; $R^4$ is hydrogen; $R^5$ is —$CH_3$; and $R^6$ is OH; then $R^7$ is not hydrogen. In some embodiments, when $R^1$ and $R^2$ are —OH; $R^5$ is —$CH_3$; $R^6$ is —OH; and $R^7$ is hydrogen; then $R^4$ is not hydrogen. In some embodiments, when $R^1$ and $R^2$ are —OH; $R^5$ is $C_1$-$C_6$ alkyl; $R^6$ is —OH; and $R^7$ is hydrogen; then $R^4$ is not hydrogen. In some embodiments, when $R^1$ and $R^2$ are —OH; $R^4$ is hydrogen; $R^6$ is OH; and $R^7$ is not hydrogen. $R^5$ is not —$CH_3$.

In some embodiments, the compound having the structure of Formula (I) or (Ia) is not (6aR,12bS)-5,6,6a,7,8,12b-hexahydrobenzo[a]phenanthridine-2,10,11-triol. In some embodiments, when $R^1$ and $R^2$ are —OH; $R^4$ is hydrogen; $R^6$ is OH; then $R^5$ and $R^7$ are not both hydrogen. In some embodiments, when $R^1$ and $R^2$ are —OH; $R^6$ is OH; then $R^5$ and $R^7$ are both hydrogen; then $R^4$ is not hydrogen.

In some embodiments, the compound having the structure of Formula (I) or (Ia) is not 5,6,6a,7,8,12b-hexahydrobenzo[a]phenanthridine-10,11-diol. In some embodiments, when $R^1$ and $R^2$ are —OH and $R^4$ is hydrogen; at least one of $R^5$, $R^6$, or $R^7$ is not hydrogen. In some embodiments, when $R^1$ and $R^2$ are —OH and each of $R^5$, $R^6$, or $R^7$ is hydrogen; then $R^4$ not hydrogen. In some embodiments, when $R^4$ is hydrogen and each of $R^5$, $R^6$, or $R^7$ is hydrogen; then one of $R^1$ or $R^2$ is not —OH.

In some embodiments, when $R^1$ and $R^2$ are —OH; $R^4$ is hydrogen; then only one of $R^5$, $R^6$ and $R^7$ is hydrogen. In some embodiments, when $R^1$ and $R^2$ are —OH, then at least two of $R^5$, $R^6$, or $R^7$ are —OH. In some embodiments, when $R^1$ and $R^2$ are —OH and $R^4$ is hydrogen; then at least two of $R^5$, $R^6$, or $R^7$ are —OH.

In some embodiments, the compound of Formula (I), or a pharmaceutically acceptable salt or solvate thereof, has the structure of Formula (II), or a pharmaceutically acceptable salt or solvate thereof:

Formula (II)

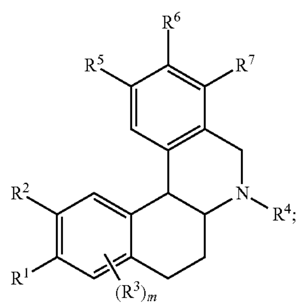

wherein:

m is 0, 1, or 2;

each $R^1$ and $R^2$ is independently hydrogen, halogen, —CN, —OH, —$OR^a$, —SH, —$SR^a$, —S(═O)$R^a$, —$NO_2$, —N$(R^b)_2$, —S(═O)$_2R^a$, —NHS(═O)$_2R^a$, —S(═O)$_2$N$(R^b)_2$, —C(═O)$R^a$, —OC(═O)$R^a$, —C(═O)$OR^b$, —OC(═O)OR, —C(═O)N$(R^b)_2$, —OC(═O)N$(R^b)_2$, —$NR^b$C(═O)N$(R^b)_2$, —$NR^b$C(═O)$R^a$, —$NR^b$C(═O)OR, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl, and $C_1$-$C_6$ heteroalkyl is unsubstituted or substituted with one, two, or three $R^8$;

or $R^1$ and $R^2$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

$R^3$ is hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

$R^4$ is hydrogen or $C_1$-$C_6$ alkyl;

each $R^5$, $R^6$, and $R^7$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$;

or $R^5$ and $R^6$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

or $R^6$ and $R^7$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$;

each $R^8$ is independently halogen, —CN, —OH, —$OR^a$, —N$(R^b)_2$, —S(═O)$_2R^a$, —NHS(═O)$_2R^a$, —OC(═O)N$(R^b)_2$, —$NR^b$C(═O)N$(R^b)_2$, —$NR^b$C(═O)$R^a$, —$NR^b$C(═O)OR, $C_1$-$C_6$ alkyl, $C_1$-$C_6$ haloalkyl, $C_1$-$C_6$ hydroxyalkyl, $C_1$-$C_6$ heteroalkyl, or cycloalkyl, wherein each alkyl, heteroalkyl, and cycloalkyl is independently unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, each $R^1$ and $R^2$ is independently hydrogen, halogen, —CN, —OH, —$OR^a$, —SH, —$SR^a$, —S(═O)$R^a$, —$NO_2$, —N$(R^b)_2$, —S(═O)$_2R^a$, —NHS(═O)$_2R^a$, —S(═O)$_2$N$(R^b)_2$, —C(═O)$R^a$, —OC(═O)$R^a$, —C(═O)OR, —OC(═O)OR, —C(═O)N$(R^b)_2$, —OC (=O)N($R^b$)$_2$, —NR$^b$C(=O)N($R^b$)$_2$, —NR$^b$C(=O)R$^a$, or —NR$^b$C(=O)OR; or $R^1$ and $R^2$ with the intervening atoms to which they are attached form a fused 5-membered or 6-membered ring that is a fused cycloalkyl, fused heterocycloalkyl, fused phenyl or fused heteroaryl, wherein the fused ring is unsubstituted or substituted with one or two $R^8$. In some embodiments, each $R^1$ and $R^2$ is independently hydrogen, halogen, —OH, —OR$^a$, —S(=O)R$^a$, —S(=O)$_2$R$^a$, —NHS(=O)$_2$R$^a$, —S(=O)$_2$N($R^b$)$_2$, —C(=O)R$^a$, —OC(=O)R$^a$, —C(=O)OR, —OC(=O)OR, —C(=O)N($R^b$)$_2$, —OC(=O)N($R^b$)$_2$, —NR$^b$C(=O)N($R^b$)$_2$, —NR$^b$C(=O)R$^a$, or —NRC(=O)OR; or $R^1$ and $R^2$ with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^8$. In some embodiments, each $R^1$ and $R^2$ is independently hydrogen, halogen, —OH, —OR$^a$, —S(=O)R$^a$, —N($R^b$)$_2$, —S(=O)$_2$R$^a$, —NHS(=O)$_2$R$^a$, —S(=O)$_2$N($R^b$)$_2$, —C(=O)R$^a$, —OC(=O)R$^a$, —C(=O)OR$^b$, —OC(=O)OR, —C(=O)N($R^b$)$_2$, —OC(=O)N($R^b$)$_2$, —NR$^b$C(=O)N($R^b$)$_2$, —NR$^b$C(=O)R$^a$, or —NRC(=O)OR; or $R^1$ and $R^2$ with the intervening atoms to which they are attached form a fused 5-membered ring that is a fused cycloalkyl, fused heterocycloalkyl, fused phenyl or fused heteroaryl, wherein the fused ring is unsubstituted or substituted with one or two $R^8$.

In some embodiments, each $R^1$ and $R^2$ is independently —OH, —OR$^a$, —SH, —SR$^a$, —S(=O)R$^a$, —NO$_2$, —N($R^b$)$_2$, —S(=O)$_2$R$^a$, —NHS(=O)$_2$R$^a$, —S(=O)$_2$N($R^b$)$_2$, —C(=O)R$^a$, —OC(=O)R$^a$, —C(=O)OR$^b$, —OC(=O)OR, —C(=O)N($R^b$)$_2$, —OC(=O)N($R^b$)$_2$, —NR$^b$C(=O)N($R^b$)$_2$, —NR$^b$C(=O)R$^a$, or —NR$^b$C(=O)OR. In some embodiments, each $R^1$ and $R^2$ is independently hydrogen, halogen, —CN, —OH, —OR$^a$, —SH, —SR$^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$. In some embodiments, each $R^1$ and $R^2$ is independently hydrogen, halogen, —CN, —OH, or —OR$^a$. In some embodiments, each $R^1$ and $R^2$ is independently —Cl, —Br, or —F. In some embodiments, each $R^1$ and $R^2$ is independently hydrogen, —OH, or —OR$^a$. In some embodiments, each $R^1$ and $R^2$ is independently —OR$^a$. In some embodiments, each $R^1$ and $R^2$ is independently —OCH$_3$ or —OCH$_2$CH$_3$. In some embodiments, each $R^1$ and $R^2$ is —OH.

In some embodiments, $R^1$ and $R^2$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$. In some embodiments, $R^1$ and $R^2$ with the intervening atoms to which they are attached form a fused 5-membered ring that is a fused cycloalkyl, fused heterocycloalkyl, fused phenyl, or fused heteroaryl; wherein the fused ring is unsubstituted or substituted with one or two $R^8$. In some embodiments, $R^1$ and $R^2$ with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$.

In some embodiments, $R^3$ is hydrogen, halogen, —CN, —OH, —OR$^a$, —SH, —SR$^a$, $C_1$-$C_6$ alkyl. In some embodiments, $R^3$ is hydrogen, halogen, —CN, —OH, —OR$^a$. In some embodiments, each $R^1$ and $R^2$ is independently —Cl, —Br, or —F. In some embodiments, $R^3$ is $C_1$-$C_6$ alkyl. In some embodiments, $R^3$ is —CH$_3$ or —CH$_2$CH$_3$. In some embodiments, $R^3$ is —OH, —OCH$_3$ or —OCH$_2$CH$_3$. In some embodiments, $R^3$ is —Cl, —Br, or —F. In some embodiments, $R^3$ is hydrogen.

In some embodiments, each $R^5$, $R^6$, and $R^7$ is independently hydrogen, halogen, —CN, —OH, —OR$^a$, —SH, —SR$^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$.

In some embodiments, $R^5$ is hydrogen; $R^6$ is —OH, —OR$^a$, or $C_1$-$C_6$ alkyl; and $R^7$ is hydrogen, —OH, —OR$^a$, or $C_1$-$C_6$ alkyl. In some embodiments, $R^5$ is hydrogen; $R^6$ is —OH or —OR$^a$; and $R^7$ is hydrogen, —OH, or —OR$^a$. In some embodiments, $R^5$ is hydrogen; $R^6$ is —OH; and $R^7$ is —OH.

In some embodiments, $R^5$ is OH, —OR$^a$, or $C_1$-$C_6$ alkyl; $R^6$ is hydrogen, —OH, —OR$^a$, or $C_1$-$C_6$ alkyl; and $R^7$ is hydrogen. In some embodiments, $R^5$ is OH or —OR$^a$; $R^6$ is hydrogen, —OH, or —OR$^a$; and $R^7$ is hydrogen. In some embodiments, $R^5$ is OH; $R^6$ is —OH; and $R^7$ is hydrogen.

In some embodiments, $R^5$ and $R^6$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$. In some embodiments, $R^5$ and $R^6$ are taken together with the intervening atoms to which they are attached form a fused 5-membered ring, that is a fused cycloalkyl, fused heterocycloalkyl, or fused heteroaryl; wherein the fused ring is unsubstituted or substituted with one or two $R^8$. In some embodiments, $R^5$ and $R^6$ are taken together with the intervening atoms to which they are attached form a fused 6-membered ring, that is a fused cycloalkyl, fused heterocycloalkyl, fused phenyl, or fused heteroaryl; wherein the fused ring is unsubstituted or substituted with one or two $R^8$.

In some embodiments, $R^6$ and $R^7$ are taken together with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^8$. In some embodiments, $R^6$ and $R^7$ are taken together with the intervening atoms to which they are attached form a fused 5-membered ring. In some embodiments, $R^6$ and $R^7$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^8$.

In some embodiments, m is 1 or 2. In some embodiments, m is 2. In some embodiments, m is 1. In some embodiments, m is 0.

In some embodiments, the compound having the structure of Formula (Ia), or a pharmaceutically acceptable salt or solvate thereof, has the structure of Formula (III-1), or a pharmaceutically acceptable salt or solvate thereof:

Formula (III-1)

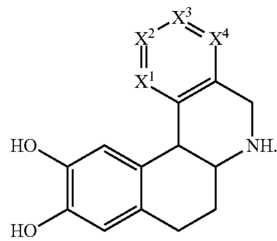

In some embodiments of Formula (III-1), $X^1$ is N; $X^2$ is CR5; $X^3$ is $CR^6$; and $X^4$ is $CR^7$. In some embodiments, $X^1$ is $CR^{24}$; $X^2$ is N; $X^3$ is $CR^6$; and $X^4$ is $CR^7$. In some embodiments, $X^1$ is $CR^{24}$; $X^2$ is $CR^5$; $X^3$ is N; and $X^4$ is $CR^7$. In some embodiments, $X^1$ is $CR^{24}$; $X^2$ is $CR^5$; $X^3$ is $CR^6$; and $X^4$ is N.

In some embodiments of Formula (III-1), $X^1$ and $X^2$ are taken together with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^8$. In some embodiments of Formula (III-1), $X^2$ and $X^3$ are taken together with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^8$. In some embodiments of Formula (III-1), $X^3$ and $X^4$ are taken together with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^8$.

In some embodiments, the compound having the structure of Formula (I), or a pharmaceutically acceptable salt or solvate thereof, has the structure of Formula (III-2), or a pharmaceutically acceptable salt or solvate thereof:

Formula (III-2)

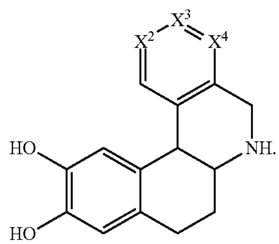

In some embodiments of Formula (III-2), $X^2$ is N; $X^3$ is $CR^6$; and $X^4$ is $CR^7$. In some embodiments, $X^2$ is $CR^5$; $X^3$ is N; and $X^4$ is $CR^7$. In some embodiments, $X^2$ is $CR^5$; $X^3$ is $CR^6$; and $X^4$ is N.

In some embodiments of Formula (III-2), $X^2$ and $X^3$ are taken together with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^8$. In some embodiments of Formula (III-2), $X^3$ and $X^4$ are taken together with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^8$.

In some embodiments, the compound having the structure of Formula (III-1) or (III-2), or a pharmaceutically acceptable salt or solvate thereof, has the structure of Formula (IIIa), (IIIb), (IIIc), or (IIId), or a pharmaceutically acceptable salt thereof:

Formula (IIIa)

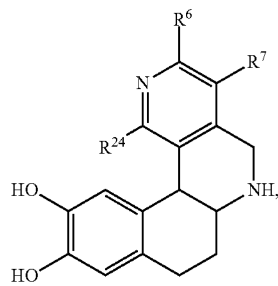

Formula (IIIb)

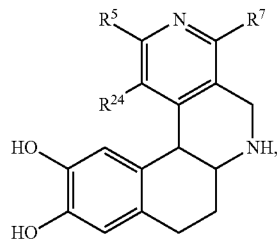

Formula (IIIc)

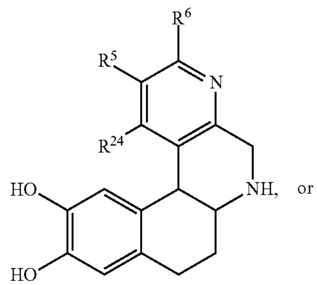

or

Formula (IIId)

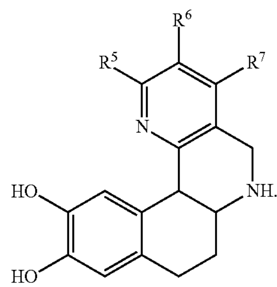

In some embodiments, $X^2$ is N; and $R^{24}$, $R^6$ and $R^7$ is each independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$. In some embodiments, $X^2$ is N; and $R^{24}$, $R^6$, and $R^7$ is each independently hydrogen, OH, or —$OR^a$. In some embodiments, $X^2$ is N; and $R^6$ is hydrogen; and $R^7$ is —$OR^a$. In some embodiments, $X^2$ is N; and $R^7$ is hydrogen; and $R^6$ is —$OR^a$.

In some embodiments, $X^3$ is N; and $R^{24}$, $R^5$ and $R^7$ is each independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$. In some embodiments, $X^3$ is N; and $R^{24}$, $R^5$, and $R^7$ is each independently hydrogen, OH, or —$OR^a$. In some embodiments, $X^3$ is N; and $R^5$ is hydrogen; and $R^7$ is —$OR^a$. In some embodiments, $X^3$ is N; and $R^7$ is hydrogen; and $R^5$ is —$OR^a$.

In some embodiments, $X^4$ is N; and $R^{24}$, $R^5$, and $R^6$ is each independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$. In some embodiments, $X^4$ is N; and $R^{24}$, $R^5$, and $R^6$ is each independently hydrogen, OH, or —$OR^a$. In some embodiments, $X^3$ is N; and $R^5$ is hydrogen; and $R^6$ is —$OR^a$. In some embodiments, $X^3$ is N; and $R^6$ is hydrogen; and $R^5$ is —$OR^a$.

In some embodiments, $X^1$ is N; and $R^5$, $R^6$ and $R^7$ is each independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^8$. In some embodiments, $X^1$ is N; and $R^5$, $R^6$, and $R^7$ is each independently hydrogen, OH, or —$OR^a$.

In some embodiments, the compound having the structure of Formula (I), or a pharmaceutically acceptable salt or solvate thereof, has the structure of Formula (IV), or a pharmaceutically acceptable salt or solvate thereof:

Formula (IV)

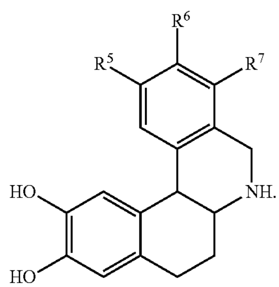

In another aspect, described herein is a compound of Formula (V), or a pharmaceutically acceptable salt or solvate thereof:

Formula (V)

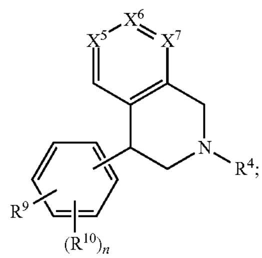

wherein:

$X^5$ is N or $CR^{11}$;

$X^6$ is N or $CR^{12}$;

$X^7$ is N or $CR^{13}$;

or $X^5$ and $X^6$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^{14}$;

or $X^6$ and $X^7$ are taken together with the intervening atoms to which they are attached form a fused 6-membered ring that is a fused cycloalkyl, fused heterocycloalkyl, fused phenyl, or fused heteroaryl; wherein the fused ring is unsubstituted or substituted with one or two $R^{14}$;

n is 0, 1, or 2;

$R^4$ is hydrogen or $C_1$-$C_6$ alkyl;

each $R^9$ and $R^{10}$ is independently hydrogen, halogen, —CN, —OH, —$OR^a$, —SH, —$SR^8$, —S(═O)$R^a$, —$NO_2$, —N$(R^b)_2$, —S(═O)$_2R^a$, —NHS(═O)$_2R^a$, —S(═O)$_2$N$(R^b)_2$, —C(═O)$R^a$, —OC(═O)$R^a$, —C(═O)$OR^b$, —OC(═O)OR, —C(═O)N$(R^b)_2$, —OC(═O)N$(R^b)_2$, —$NR^b$C(═O)N$(R^b)_2$, —NRC(═O)$R^a$, —NRC(═O)OR, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$;

or $R^9$ and $R^{10}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{14}$;

each $R^{11}$, $R^{12}$, and $R^{13}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$;

each $R^{14}$ is independently halogen, —CN, —OH, —$OR^a$, —N$(R^b)_2$, —S(═O)$_2R^a$, —NHS(═O)$_2R^a$, —OC(═O)N$(R^b)_2$, —$NR^b$C(═O)N$(R^b)_2$, —$NR^b$C(═O)$R^a$, —$NR^b$C(═O)OR, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, $X^5$ and $X^6$ are taken together with the intervening atoms to which they are attached form a fused 5-membered ring that is a fused cycloalkyl, fused heterocycloalkyl, fused phenyl or fused heteroaryl, wherein the fused ring is unsubstituted or substituted with one or two $R^{14}$. In some embodiments, $X^5$ and $X^6$ are taken together with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^{14}$.

In some embodiments, $X^6$ and $X^7$ are taken together with the intervening atoms to which they are attached form a fused 5-membered ring that is a fused cycloalkyl, fused heterocycloalkyl, fused phenyl or fused heteroaryl, wherein the fused ring is unsubstituted or substituted with one or two $R^{14}$. In some embodiments, $X^6$ and $X^7$ are taken together with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^{14}$.

In another aspect, described herein is a compound of Formula (V), or a pharmaceutically acceptable salt or solvate thereof:

Formula (V)

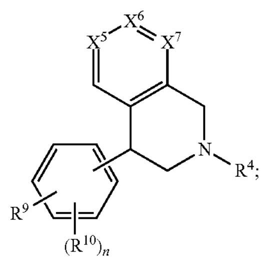

wherein:

$X^5$ is N or $CR^{11}$;

$X^6$ is N or $CR^{12}$;

$X^7$ is N or $CR^3$;

n is 0, 1, or 2;

$R^4$ is hydrogen or $C_1$-$C_6$ alkyl;

each $R^9$ and $R^{10}$ is independently hydrogen, halogen, —CN, —OH, —$OR^a$, —SH, —$SR^a$, —S(═O)$R^a$, —$NO_2$, —$N(R^b)_2$, —$S(═O)_2R^a$, —NHS$(═O)_2R^a$, —$S(═O)_2N(R^b)_2$, —C(═O)$R^a$, —OC(═O)$R^a$, —C(═O)$OR^b$, —OC(═O)$OR^b$, —C(═O)$N(R^b)_2$, —OC(═O)$N(R^b)_2$, —$NR^b$C(═O)$N(R^b)_2$, —$NR^b$C(═O)$R^a$, —$NR^b$C(═O)$OR^b$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$;

or $R^9$ and $R^{10}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{14}$;

each $R^{11}$, $R^{12}$, and $R^{13}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$;

each $R^{14}$ is independently halogen, —CN, —OH, —$OR^a$, —$N(R^b)_2$, —$S(═O)_2R^a$, —NHS$(═O)_2R^a$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, n is 1 or 2. In some embodiments, n is 2. In some embodiments, n is 1. In some embodiments, n is 0.

In some embodiments, the compound having the structure of Formula (V), or a pharmaceutically acceptable salt or solvate thereof, has the structure of Formula (VI), or a pharmaceutically acceptable salt or solvate thereof:

Formula (VI)

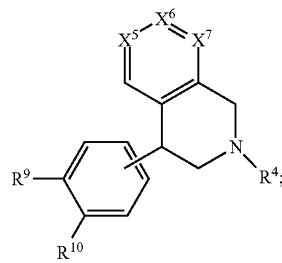

wherein:

$X^5$ is N or $CR^{11}$;

$X^6$ is N or $CR^{12}$;

$X^7$ is N or $CR^{13}$;

$R^4$ is hydrogen or $C_1$-$C_6$ alkyl;

each $R^9$ and $R^{10}$ is independently hydrogen, halogen, —CN, —OH, —$OR^a$, —SH, —$SR^a$, —S(═O)$R^a$, —$NO_2$, —$N(R^b)_2$, —$S(═O)_2R^a$, —NHS$(═O)_2R^a$, —$S(═O)_2N(R^b)_2$, —C(═O)$R^a$, —OC(═O)$R^a$, —C(═O)$OR^b$, —OC(═O)OR, —C(═O)$N(R^b)_2$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$;

or $R^9$ and $R^{10}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{14}$;

each $R^{11}$, $R^{12}$, and $R^{13}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$;

each $R^{14}$ is independently halogen, —CN, —OH, —$OR^a$, —$N(R^b)_2$, —$S(=O)_2R^a$, —$NHS(=O)_2R^a$, —$OC(=O)N(R^b)_2$, —$NRC(=O)N(R^b)_2$, —$NR^bC(=O)R^a$, —$NR^bC(=O)OR$, $C_1$-$C_6$ alkyl, $C_1$-$C_6$ haloalkyl, $C_1$-$C_6$ hydroxyalkyl, $C_1$-$C_6$ heteroalkyl, or cycloalkyl which is unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, each $R^9$ and $R^{10}$ is independently hydrogen, halogen, —CN, —OH, —$OR^a$, —SH, —$SR^a$, —$S(=O)R^a$, —$NO_2$, —$N(R^b)_2$, —$S(=O)_2R^a$, —$NHS(=O)_2R^a$, —$S(=O)_2N(R^b)_2$, —$C(=O)R^a$, —$OC(=O)R^a$, —$C(=O)OR$, —$OC(=O)OR$, —$C(=O)N(R^b)_2$, —$OC(=O)N(R^b)_2$, —$NR^bC(=O)N(R^b)_2$, —$NRC(=O)R^a$, or —$NR^bC(=O)OR$; or $R^9$ and $R^{10}$ with the intervening atoms to which they are attached form a fused 5-membered or 6-membered ring that is a fused cycloalkyl, fused heterocycloalkyl, fused phenyl or fused heteroaryl, wherein the fused ring is unsubstituted or substituted with one or two $R^{14}$. In some embodiments, each $R^9$ and $R^{10}$ is independently hydrogen, halogen, —OH, —$OR^a$, —$S(=O)R^a$, —$S(=O)_2R^a$, —$NHS(=O)_2R^a$, —$S(=O)_2N(R^b)_2$, —$C(=O)R^a$, —$OC(=O)R^a$, —$C(=O)OR$, —$OC(=O)OR$, —$C(=O)N(R^b)_2$, —$OC(=O)N(R^b)_2$, —$NR^bC(=O)N(R^b)_2$, —$NR^bC(=O)R^a$, or —$NR^bC(=O)OR$; or $R^9$ and $R^{10}$ with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^{14}$. In some embodiments, each $R^9$ and $R^{10}$ is independently hydrogen, halogen, —OH, —$OR^a$, —$S(=O)R^a$, —$N(R^b)_2$, —$S(=O)_2R^a$, —$NHS(=O)_2R^a$, —$S(=O)_2N(R^b)_2$, —$C(=O)R^a$, —$OC(=O)R^a$, —$C(=O)OR^b$, —$OC(=O)OR$, —$C(=O)N(R^b)_2$, —$OC(=O)N(R^b)_2$, —$NR^bC(=O)N(R^b)_2$, —$NR^bC(=O)R^a$, or —$NRC(=O)OR$; or $R^9$ and $R^{10}$ with the intervening atoms to which they are attached form a fused 5-membered ring that is a fused cycloalkyl, fused heterocycloalkyl, fused phenyl or fused heteroaryl, wherein the fused ring is unsubstituted or substituted with one or two $R^{14}$.

In some embodiments, each $R^9$ and $R^{10}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$. In some embodiments, each $R^9$ and $R^{10}$ is independently hydrogen, halogen, —CN, —OH, or —$OR^a$. In some embodiments, each $R^9$ and $R^{10}$ is independently —Cl, —Br, or —F. In some embodiments, each $R^9$ and $R^{10}$ is independently hydrogen, —OH, or —$OR^a$. In some embodiments, each $R^9$ and $R^{10}$ is independently —$OR^a$. In some embodiments, each $R^9$ and $R^{10}$ is independently —$OCH_3$ or —$OCH_2CH_3$. In some embodiments, each $R^9$ and $R^{10}$ is independently —OH.

In some embodiments, each $R^9$ and $R^{10}$ is independently hydrogen, halogen, —CN, —OH, —$OR^a$, —SH, —$SR^a$, —$S(=O)R^a$, —$NO_2$, —$N(R^b)_2$, —$S(=O)_2R^a$, —$NHS(=O)_2R^a$, —$S(=O)_2N(R^b)_2$, —$C(=O)R^a$, —$OC(=O)R^a$, —$C(=O)OR$, —$OC(=O)OR$, —$C(=O)N(R^b)_2$, —$OC(=O)N(R^b)_2$, —$NR^bC(=O)N(R^b)_2$, —$NRC(=O)R^a$, or —$NR^bC(=O)OR$.

In some embodiments, $R^9$ and $R^{10}$ with the intervening atoms to which they are attached form a fused 5-membered or 6-membered ring that is a fused cycloalkyl, fused heterocycloalkyl, fused phenyl or fused heteroaryl, wherein the fused ring is unsubstituted or substituted with one or two $R^{14}$. In some embodiments, $R^9$ and $R^{10}$ with the intervening atoms to which they are attached form a fused 5-membered ring that is a fused cycloalkyl, fused heterocycloalkyl, fused phenyl or fused heteroaryl, wherein the fused ring is unsubstituted or substituted with one or two $R^{14}$. In some embodiments, $R^9$ and $R^{10}$ with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^{15}$.

In some embodiments, each $R^{11}$, $R^{12}$, and $R^{13}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$. In some embodiments, each $R^{11}$, $R^{12}$, and $R^{13}$ is independently $C_1$-$C_6$ alkyl, $C_2$-$C_6$ alkenyl, $C_2$-$C_6$ alkynyl, or $C_1$-$C_6$ heteroalkyl. In some embodiments, each $R^{11}$, $R^{12}$, and $R^{13}$ is independently $C_1$-$C_6$ alkyl. In some embodiments, each $R^{11}$, $R^{12}$, and $R^{13}$ is independently hydrogen, halogen, —CN, —OH, —$OR^a$. In some embodiments, each $R^{11}$, $R^{12}$, and $R^{13}$ is hydrogen.

In some embodiments, $X^5$ is N; $X^6$ is $CR^{12}$; and $X^7$ is $CR^{13}$. In some embodiments, $X^5$ is $CR^{11}$; $X^6$ is N; and $X^7$ is $CR^{13}$. In some embodiments, $X^5$ is $CR^{11}$; $X^6$ is $CR^{12}$; and $X^7$ is N.

In some embodiments; $R^{11}$ is hydrogen, —OH, —$OR^a$, or $C_1$-$C_6$ alkyl; and $R^{13}$ is hydrogen. In some embodiments; $R^{11}$ is —OH; and $R^{13}$ is hydrogen. In some embodiments; $R^{11}$ is hydrogen; and $R^{13}$ is hydrogen.

In some embodiments; $R^{12}$ is hydrogen, —OH, —$OR^a$, or $C_1$-$C_6$ alkyl; and $R^{13}$ is hydrogen. In some embodiments; $R^{12}$ is —OH; and $R^{13}$ is hydrogen. In some embodiments; $R^{12}$ is hydrogen; and $R^{13}$ is hydrogen.

In some embodiments; $R^{11}$ is hydrogen, —OH, —$OR^a$, or $C_1$-$C_6$ alkyl; and $R^{12}$ is hydrogen. In some embodiments;

$R^{11}$ is —OH; and $R^{12}$ is hydrogen. In some embodiments; $R^{11}$ is hydrogen; and $R^{12}$ is hydrogen.

In some embodiments, the compound having the structure of Formula (VI), or a pharmaceutically acceptable salt or solvate thereof, has the structure of Formula (VIIa) or (VIIb), or a pharmaceutically acceptable salt or solvate thereof:

Formula (VIIa)

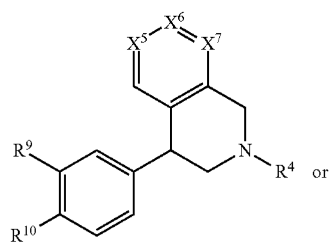

or

Formula (VIIb)

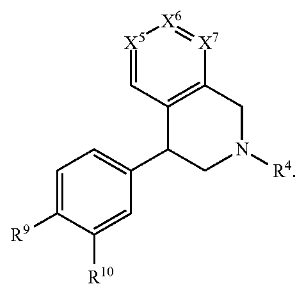

In some embodiments, $X^5$ is N; $X^6$ is $CR^{12}$; and $X^7$ is $CR^{13}$. In some embodiments, $X^5$ is $CR^{11}$; $X^6$ is N; and $X^7$ is $CR^{13}$. In some embodiments, $X^5$ is $CR^{11}$; $X^4$ is $CR^{12}$; and $X^7$ is N.

In some embodiments, the compound having the structure of Formula (VI), or a pharmaceutically acceptable salt or solvate thereof, has the structure of Formula (VIIIa), (VIIIb), or (VIIIc), or a pharmaceutically acceptable salt or solvate thereof:

Formula (VIIIa)

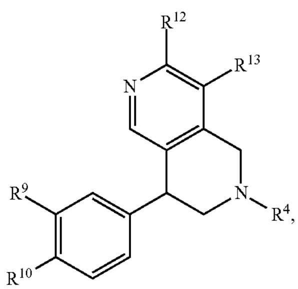

Formula (VIIIb)

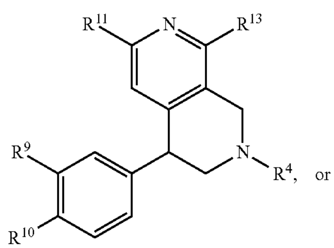

or

-continued

Formula (VIIIc)

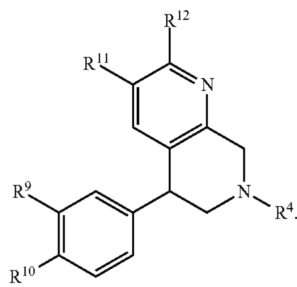

In some embodiments, $X^5$ is N; and $R^{12}$ and $R^{13}$ is each independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$. In some embodiments, $X^5$ is N; and $R^{12}$ and $R^{13}$ is each independently hydrogen, OH, or —$OR^a$. In some embodiments, $X^5$ is N; and $R^{12}$ is hydrogen; and $R^{13}$ is —$OR^a$. In some embodiments, $X^5$ is N; and $R^{13}$ is hydrogen; and $R^{12}$ is —$OR^a$.

In some embodiments, $X^6$ is N; and $R^{11}$ and $R^{13}$ is each independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{14}$. In some embodiments, $X^6$ is N; and $R^{11}$ and $R^{13}$ is each independently hydrogen, OH, or —$OR^a$. In some embodiments, $X^6$ is N; and $R^{11}$ is hydrogen; and $R^{13}$ is —$OR^a$. In some embodiments, $X^6$ is N; and $R^{13}$ is hydrogen; and $R^{11}$ is —$OR^a$.

In some embodiments, $X^7$ is N; and $R^{11}$ and $R^{12}$ is each independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{13}$. In some embodiments, $X^7$ is N; and $R^{11}$ and $R^{12}$ is each independently hydrogen, OH, or —$OR^a$. In some embodiments, $X^7$ is N; and $R^{11}$ is hydrogen; and $R^{12}$ is —$OR^a$. In some embodiments, $X^7$ is N; and $R^{12}$ is hydrogen; and $R^{11}$ is —$OR^a$.

In another aspect, described herein is a compound of Formula (IX), or a pharmaceutically acceptable salt or solvate thereof:

Formula (IX)

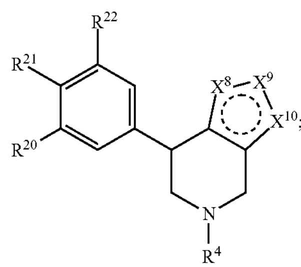

wherein:

$X^8$ is N, O, S, or $CR^{11}$;

$X^9$ is N, O, S, or $CR^{16}$;

$X^{10}$ is N, O, S, or $CR^{17}$;

provided that only one of $X^8$, $X^9$, and $X^{10}$ is O or S;

$R^4$ is hydrogen or $C_1$-$C_6$ alkyl;

each $R^{15}$, $R^{16}$, and $R^{17}$ is independently hydrogen, halogen, —CN, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$;

each $R^{20}$, $R^{21}$, and $R^{22}$ is independently hydrogen, halogen, —CN, —OH, —$OR^a$, —SH, —$SR^a$, —S(═O)$R^a$, —$NO_2$, —$N(R^b)_2$, —$S(═O)_2R^a$, —NHS$(═O)_2R^a$, —$S(═O)_2N(R^b)_2$, —C(═O)$R^a$, —OC(═O)$R^a$, —C(═O)OR, —OC(═O)OR, —C(═O)$N(R^b)_2$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{19}$;

or $R^{20}$ and $R^{21}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{19}$;

or $R^{21}$ and $R^{22}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{19}$;

each $R^{18}$ and $R^{19}$ is independently halogen, —CN, —OH, —$OR^a$, —$N(R^b)_2$, —$S(═O)_2R^a$, —NHS$(═O)_2R^a$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_1$-$C_6$ haloalkyl, $C_1$-$C_6$ hydroxyalkyl, $C_1$-$C_6$ heteroalkyl, or cycloalkyl which is unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, each $R^{15}$, $R^{16}$, and $R^{17}$ is independently hydrogen, halogen, —CN, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$. In some embodiments, each $R^{15}$, $R^{16}$, and $R^{17}$ is independently $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$. In some embodiments, each $R^{15}$, $R^{16}$, and $R^{17}$ is independently $C_1$-$C_6$ alkyl or $C_2$-$C_6$ alkenyl. In some embodiments, each $R^{15}$, $R^{16}$, and $R^{17}$ is independently $C_1$-$C_6$ alkyl. In some embodiments, each $R^{15}$, $R^{16}$, and $R^{17}$ is independently —$CH_3$, —$CH_2CH_3$, —$(CH_2)_2CH_3$, —$(CH_2)_3CH_3$, or —$CH_2(CH_3)_2$. In some embodiments, each $R^{15}$, $R^{16}$, and $R^{17}$ is independently —$(CH_2)_2CH_3$, —$(CH_2)_3CH_3$, or —$CH(CH_3)_2$. In some embodiments, each $R^{15}$, $R^{16}$, and $R^{17}$ is independently —$(CH_2)_2CH_3$. In some embodiments, each $R^{15}$, $R^{16}$, and $R^{17}$ is independently —$(CH_2)_3CH_3$. In some embodiments, each $R^{15}$, $R^{16}$, and $R^{17}$ is independently —$CH(CH_3)_2$. In some embodiments, each $R^{15}$, $R^{16}$, and $R^{17}$ is independently hydrogen, halogen, or —CN. In some embodiments, each $R^{15}$, $R^{16}$, and $R^{17}$ is independently hydrogen, —Br, —Cl, or —F. In some embodiments, each $R^{15}$, $R^{16}$, and $R^{17}$ is independently hydrogen.

In some embodiments, each $R^{20}$, $R^{21}$, and $R^{22}$ is independently hydrogen, halogen, —CN, —OH, —$OR^a$, —SH, —$SR^a$, —S(═O)$R^a$, —$NO_2$, —$N(R^b)_2$, —$S(═O)_2R^a$, —NHS$(═O)_2R^a$, —$S(═O)_2N(R^b)_2$, —C(═O)$R^a$, —OC(═O)$R^a$, —C(═O)OR, —OC(═O)OR, —C(═O)$N(R^b)_2$, —OC(═O)$N(R^b)_2$, —$NR^b$C(═O)$N(R^b)_2$, —NRC(═O)$R^a$, or —$NR^b$C(═O)OR. In some embodiments, each $R^{20}$, $R^{21}$, and $R^{22}$ is independently hydrogen, halogen, —CN, —OH, —$OR^a$, —SH, —$SR^a$, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{19}$. In some embodiments, each $R^{20}$, $R^{21}$, and $R^{22}$ is independently hydrogen, halogen, —CN, —OH, —$OR^a$, $C_1$-$C_6$ alkyl, $C_2$-$C_6$ alkenyl, $C_2$-$C_6$ alkynyl, or $C_1$-$C_6$ heteroalkyl. In some embodiments, each $R^{20}$, $R^{21}$, and $R^{22}$ is independently hydrogen, halogen, —CN, —OH, —$OR^a$. In some embodiments, each $R^{20}$, $R^{21}$, and $R^{22}$ is independently hydrogen, —Cl, —Br, or —F. In some embodiments, each $R^{20}$, $R^{21}$, and $R^{22}$ is independently $C_1$-$C_6$ alkyl. In some embodiments, each $R^{20}$, $R^{21}$, and $R^{22}$ is independently —$CH_3$, —$CH_2CH_3$, or $CH(CH_3)_2$. In some embodiments, each $R^{20}$, $R^{21}$, and $R^{22}$ is independently —OH or —$OCH_3$.

In some embodiments, $R^{20}$ and $R^{21}$ are independently —OH or —$OR^a$; and $R^{22}$ is hydrogen or halogen. In some embodiments, $R^{20}$ and $R^{21}$ are independently —OH or —$OCH_3$; and $R^{22}$ is hydrogen or halogen. In some embodiments, $R^{20}$ and $R^{21}$ is —OH; and $R^{22}$ is hydrogen. In some embodiments, $R^{20}$ and $R^{21}$ is —$OCH_3$; and $R^{22}$ is hydrogen.

In some embodiments, $R^{21}$ and $R^{22}$ are independently —OH or —$OR^a$; and $R^{20}$ is hydrogen or halogen. In some embodiments, $R^{21}$ and $R^{22}$ are independently —OH or —$OCH_3$; and $R^{20}$ is hydrogen or halogen. In some embodiments, $R^{21}$ and $R^{22}$ is —OH; and $R^{20}$ is hydrogen. In some embodiments, $R^{21}$ and $R^{22}$ is —$OCH_3$; and $R^{20}$ is hydrogen.

In some embodiments, $R^{20}$ and $R^{22}$ are independently —OH or —$OR^a$; and $R^{21}$ is hydrogen or halogen. In some embodiments, $R^{20}$ and $R^{22}$ are independently —OH or —$OCH_3$; and $R^{21}$ is hydrogen or halogen. In some embodiments, $R^{20}$ and $R^{22}$ is —OH; and $R^{21}$ is hydrogen. In some embodiments, $R^{20}$ and $R^{22}$ is —$OCH_3$; and $R^{21}$ is hydrogen.

In some embodiments, $R^{20}$ and $R^{21}$ are taken together with the intervening atoms to which they are attached form a fused 5-membered or 6-membered ring that is a fused cycloalkyl, fused heterocycloalkyl, fused phenyl or fused heteroaryl, wherein the fused ring is unsubstituted or substituted with one or two $R^{19}$. In some embodiments, $R^{20}$ and $R^{21}$ with the intervening atoms to which they are attached form a fused 5-membered ring that is a fused cycloalkyl, fused heterocycloalkyl, fused phenyl or fused heteroaryl, wherein the fused ring is unsubstituted or substituted with one or two $R^{19}$. In some embodiments, $R^{20}$ and $R^{21}$ with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^{19}$.

In some embodiments, $R^{21}$ and $R^{22}$ are taken together with the intervening atoms to which they are attached form a fused 5-membered or 6-membered ring that is a fused cycloalkyl, fused heterocycloalkyl, fused phenyl or fused heteroaryl, wherein the fused ring is unsubstituted or substituted with one or two $R^{19}$. In some embodiments, $R^{21}$ and $R^{22}$ with the intervening atoms to which they are attached form a fused 5-membered ring that is a fused cycloalkyl, fused heterocycloalkyl, fused phenyl or fused heteroaryl, wherein the fused ring is unsubstituted or substituted with one or two $R^{19}$. In some embodiments, $R^{21}$ and $R^{22}$ with the intervening atoms to which they are attached form a fused 6-membered ring that is a fused cycloalkyl, fused heterocycloalkyl, fused phenyl or fused heteroaryl, wherein the fused ring is unsubstituted or substituted with one or two $R^{19}$.

In some embodiments, $X^8$ is N; $X^9$ is N; and $X^{10}$ is $CR^{17}$. In some embodiments, $X^8$ is $CR^{15}$; $X^9$ is N; and $X^{10}$ is N. In some embodiments, $X^8$ is N; $X^9$ is N; and $X^{10}$ is N. In some embodiments, $X^8$ is O or S; $X^9$ is $CR^{16}$; and $X^{10}$ is $CR^{17}$. In some embodiments, $X^8$ is S; $X^9$ is $CR^{16}$; and $X^{10}$ is $CR^{17}$. In some embodiments, $X^8$ is $CR^{15}$; $X^9$ is $CR^{16}$; and $X^{10}$ is O or S. In some embodiments, $X^8$ is $CR^{15}$; $X^9$ is $CR^{16}$; and $X^{10}$ is S.

In some embodiments, the compound of Formula (IX) is not 4-(3a,4,5,6,7,7a-hexahydrothieno[2,3-c]pyridin-4-yl) benzene-1,2-diol. In some embodiments, when $X^{10}$ is S; $R^4$ is hydrogen; $R^{20}$ is hydrogen; and each of $R^{21}$ and $R^{22}$ is —OH; $R^{15}$ is not hydrogen. In some embodiments, when $X^{10}$ is S; $R^4$ is hydrogen; $R^{15}$ is hydrogen; and $R^{21}$ and $R^{22}$ are each —OH; $R^{20}$ is not hydrogen. In some embodiments, when $X^{10}$ is S; $R^{15}$ is hydrogen; $R^{20}$ is hydrogen and $R^{21}$ and $R^{22}$ are each —OH; the $R^4$ is not hydrogen. $R^{20}$ is not hydrogen.

In some embodiments, the compound have the structure of Formula (IX), or a pharmaceutically acceptable salt or solvate thereof, has the structure of Formula (X), or a pharmaceutically acceptable salt or solvate thereof:

Formula (X)

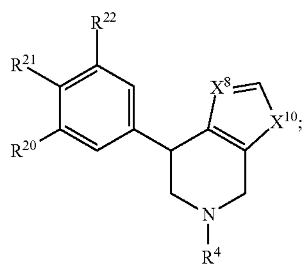

wherein:

$X^8$ is O, S, or $CR^{15}$;

$X^{10}$ is O, S, or $CR^{17}$;

provided that only one of $X^8$ and $X^{10}$ is O or S;

$R^4$ is hydrogen or $C_1$-$C_6$ alkyl;

each $R^{15}$ and $R^{17}$ is independently hydrogen, halogen, —CN, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$;

each $R^{15}$, $R^{16}$, and $R^{17}$ is independently hydrogen, halogen, —CN, —$C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$;

each $R^{20}$, $R^{21}$, and $R^{22}$ is independently hydrogen, halogen, —CN, —OH, —$OR^a$, —SH, —$SR^a$, —S(═O)$R^a$, —$NO_2$, —$N(R^b)_2$, —$S(═O)_2R^a$, —$NHS(═O)_2R^a$, —$S(═O)_2N(R^b)_2$, —C(═O)$R^a$, —OC(═O)$R^a$, —C(═O)OR, —OC(═O)OR, —C(═O)$N(R^b)_2$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{19}$;

or $R^{20}$ and $R^{21}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{19}$;

or $R^{21}$ and $R^{22}$ with the intervening atoms to which they are attached form a fused 5-membered or 6-membered ring that is a fused cycloalkyl, fused heterocycloalkyl, fused phenyl, or fused heteroaryl; wherein the fused ring is unsubstituted or substituted with one or two $R^{18}$;

each $R^{18}$ and $R^{19}$ is independently halogen, —CN, —OH, —$OR^a$, —$N(R^b)_2$, —$S(═O)_2R^a$, —$NHS(═O)_2R^a$, —OC(═O)$N(R^b)_2$, —$NR^b$C(═O)$N(R^b)_2$, —$NR^b$C(═O)$R^a$, —$NR^b$C(═O)OR, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl;

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl; and each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl.

In some embodiments, $X^8$ is O or S; and $X^{10}$ is $CR^{17}$. In some embodiments, $X^8$ is S; and $X^{10}$ is $CR^{17}$. In some embodiments, $X^8$ is $CR^{15}$; and $X^{10}$ is O or S. In some embodiments, $X^8$ is $CR^1$; and $X^{10}$ is S.

In some embodiments, the compound having the structure of Formula (X), or a pharmaceutically acceptable salt or solvate thereof, has the structure of Formula (Xa) or (Xb), or a pharmaceutically acceptably salt or solvate thereof:

Formula (Xa)

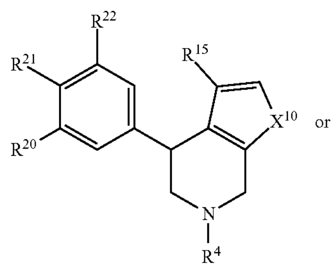

or

Formula (Xb)

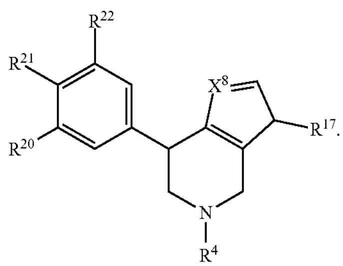

In some embodiments, $R^{15}$ is halogen, —CN, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$. In some embodiments, $R^{15}$ is $C_1$-$C_6$ alkyl, $C_2$-$C_6$ alkenyl, $C_2$-$C_6$ alkynyl, or $C_1$-$C_6$ heteroalkyl. In some embodiments, $R^{15}$ is $C_1$-$C_6$ alkyl. In some embodiments, $R^{15}$ is —$CH_3$, —$CH_2CH_3$, —$(CH_2)_2CH_3$, —$(CH_2)_3CH_3$, or —$CH(CH_3)_2$. In some embodiments, $R^{15}$ is —$(CH_2)_2CH_3$, —$(CH_2)_3CH_3$, or —$CH(CH_3)_2$. In some embodiments, $R^{15}$ is —$(CH_2)_2CH_3$. In some embodiments, $R^{15}$ is —$(CH_2)_3CH_3$. In some embodiments, $R^{15}$ is —$CH(CH_3)_2$.

In some embodiments, $R^{17}$ is halogen, —CN, $C_1$-$C_6$ alkyl, $C_2$-$C_6$ alkenyl, $C_2$-$C_6$ alkynyl, or $C_1$-$C_6$ heteroalkyl; wherein alkyl, alkenyl, alkynyl and $C_1$-$C_6$ heteroalkyl is unsubstituted or substituted with one, two, or three $R^{18}$. In some embodiments, $R^{17}$ is $C_1$-$C_6$ alkyl, $C_2$-$C_6$ alkenyl, $C_2$-$C_6$ alkynyl, or $C_1$-$C_6$ heteroalkyl. In some embodiments, $R^{17}$ is $C_1$-$C_6$ alkyl. In some embodiments, $R^{17}$ is —$CH_3$, —$CH_2CH_3$, —$(CH_2)_2CH_3$, —$(CH_2)_3CH_3$, or —$CH(CH_3)_2$. In some embodiments, $R^{17}$ is —$(CH_2)_2CH_3$, —$(CH_2)_3CH_3$, or —$CH(CH_3)_2$. In some embodiments, $R^{17}$ is —$(CH_2)_2CH_3$. In some embodiments, $R^{17}$ is —$(CH_2)_3CH_3$. In some embodiments, $R^{17}$ is —$CH(CH_3)_2$.

In some embodiments, the compound having the structure of Formula (X), or a pharmaceutically acceptable salt or solvate thereof, has the structure of Formula (Xa-1), or a pharmaceutically acceptably salt or solvate thereof:

Formula (Xa-1)

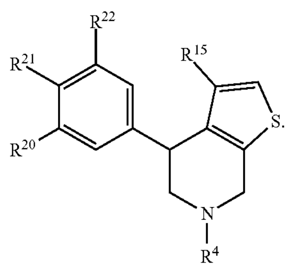

In some embodiments, $R^4$ is $C_1$-$C_6$ alkyl. In some embodiments, $R^4$ is —$CH_3$, —$CH_2CH_3$, —$(CH_2)_2CH_3$, —$CH(CH_3)CH_2CH_3$, or —$CH(CH_3)_2$. In some embodiments, $R^4$ is —$CH_3$. In some embodiments, $R^4$ is —$CH(CH_3)_2$. In some embodiments $R^4$ is hydrogen.

In some embodiments, each $R^8$, $R^{14}$, $R^{18}$, and $R^{19}$ is independently halogen, —CN, —OH, —OR a, —$N(R^b)_2$, —$S(=O)_2R^a$, —$NHS(=O)_2R^a$, —$OC(=O)N(R^b)_2$, —$NR^bC(=O)N(R^b)_2$, —$NR^bC(=O)R^a$, —$NR^bC(=O)OR$, $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl. In some embodiments, each $R^8$, $R^{14}$, $R^{18}$, and $R^{19}$ is independently halogen, —CN, —OH, —$OR^a$, —$N(R^b)_2$. In some embodiments, each $R^8$, $R^{14}$, $R^{18}$, and $R^{19}$ is independently —$S(=O)_2R^a$, —$NHS(=O)_2R^a$, —$OC(=O)N(R^b)_2$, —$NR^bC(=O)N(R^b)_2$, —$NR^bC(=O)R^a$, or —$NR^bC(=O)OR$. In some embodiments, each $R^8$, $R^{14}$, $R^{18}$, and $R^{19}$ is independently $C_1$-$C_6$ alkyl, $C_1$-$C_6$ haloalkyl, $C_1$-$C_6$ hydroxyalkyl, $C_1$-$C_6$ heteroalkyl, or cycloalkyl; wherein each alkyl, heteroalkyl, and cycloalkyl is independently unsubstituted or substituted with one, two, or three halogen, $C_1$-$C_6$ alkyl, or $C_1$-$C_6$ haloalkyl.

In some embodiments, each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl. In some embodiments, each $R^a$ is independently $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl. In some embodiments each $R^a$ is independently $C_1$-$C_6$ alkyl or $C_1$-$C_6$ heteroalkyl; wherein the alkyl or heteroalkyl is independently unsubstituted or substituted with one, two, or three halogen, —OH, $C_1$-$C_6$ alkyl, or $C_1$-$C_6$ haloalkyl. In some embodiments, each $R^a$ is independently $C_1$-$C_6$ alkyl; wherein the alkyl is unsubstituted or substituted with one, two, or three halogen.

In some embodiments, each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl. In some embodiments, each $R^b$ is independently hydrogen, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl. In some embodiments, each $R^b$ is independently hydrogen, $C_1$-$C_6$ alkyl or $C_1$-$C_6$ heteroalkyl; wherein the alkyl or heteroalkyl is independently unsubstituted or substituted with one, two, or three halogen, —OH, $C_1$-$C_6$ alkyl, or $C_1$-$C_6$ haloalkyl. In some embodiments, each $R^b$ is independently $C_1$-$C_6$ alkyl; wherein the alkyl is unsubstituted or substituted with one, two, or three halogen. In some embodiments, each $R^b$ is hydrogen.

In some embodiments, two $R^b$ groups on a nitrogen atom are taken together with the nitrogen atom to which they are attached to form a heterocycloalkyl which is unsubstituted or substituted with one, two, or three halogen, $C_1$-$C_6$ alkyl, or $C_1$-$C_6$ haloalkyl. In some embodiments, two $R^b$ groups on a nitrogen atom are taken together with the nitrogen atom to which they are attached to form a 3- to 7-membered heterocycloalkyl which is unsubstituted or substituted with one, two, or three halogen, $C_1$-$C_6$ alkyl, or $C_1$-$C_6$ haloalkyl. In some embodiments, two $R^b$ groups on a nitrogen atom are taken together with the nitrogen atom to which they are attached to form a 5- or 6-membered heterocycloalkyl which is unsubstituted or substituted with one, two, or three halogen, $C_1$-$C_6$ alkyl, or $C_1$-$C_6$ haloalkyl. In some embodiments, two $R^b$ groups on a nitrogen atom are taken together with the nitrogen atom to which they are attached to form pyrrolidine, piperidine, or morpholine which is unsubstituted or substituted with one, two, or three halogen, $C_1$-$C_6$ alkyl, or $C_1$-$C_6$ haloalkyl. In some embodiments, two $R^b$ groups on a nitrogen atom are taken together with the nitrogen atom to which they are attached to form pyrrolidine, piperidine, or morpholine. Any combination of the groups described above for the various variables is contemplated herein. Throughout the specification, groups and substituents thereof are chosen by one skilled in the field to provide stable moieties and compounds.

Any combination of the groups described above for the various variables is contemplated herein. Throughout the specification, groups and substituents thereof are chosen by one skilled in the field to provide stable moieties and compounds.

In some embodiments, the compound is a compound selected from Table 1, or a pharmaceutically acceptable salt or solvate thereof.

TABLE 1

| Name | Structure |
|---|---|
| 5,6,6a,7,8,12b-hexahydrobenzo[a]phenanthridine-3,4,10,11-tetraol | 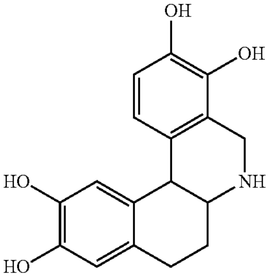 [SMILES: Oc1cc2c(cc1O)C1c3ccc(O)c(O)c3CNC1CC2] |
| (6aR,12bR)-5,6,6a,7,8,12b-hexahydrobenzo[a]phenanthridine-3,4,10,11-tetraol | 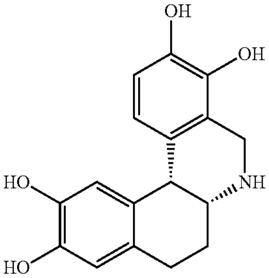 [SMILES: Oc1cc2c(cc1O)[C@@H]1c3ccc(O)c(O)c3CN[C@@H]1CC2] |

TABLE 1-continued

| Name | Structure |
|---|---|
| (6aR,12bS)-5,6,6a,7,8,12b-hexahydrobenzo[a]phenanthridine-3,4,10,11-tetraol | 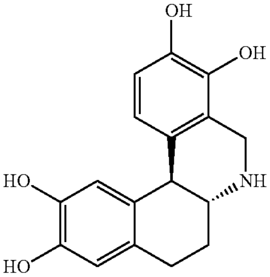 [SMILES: Oc1cc2c(cc1O)[C@H]1c3ccc(O)c(O)c3CN[C@@H]1CC2] |
| (6aR,12bS)-5,6,6a,7,8,12b-hexahydrobenzo[a]phenanthridine 2,10,11-triol | 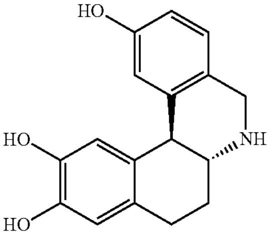 [SMILES: Oc1ccc2c(c1)[C@@H]1c3cc(O)c(O)cc3CC[C@H]1NC2] |
| (6aR,12bS)-2-methyl-5,6,6a,7,8,12b-hexahydrobenzo[a]phenanthridine-3,10,11-triol | 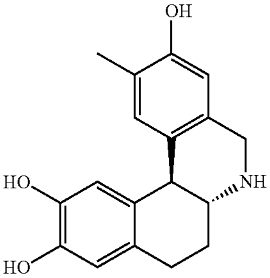 [SMILES: Cc1cc2c(cc1O)CN[C@@H]1CCc3cc(O)c(O)cc3[C@@H]21] |
| (6aS,12bR)-2-methyl-5,6,6a,7,8,12b-hexahydrobenzo[a]phenanthridine-3,10,11-triol | 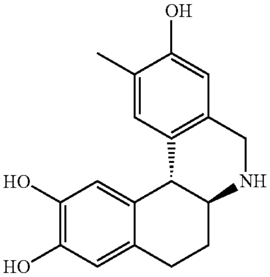 [SMILES: Cc1cc2c(cc1O)CN[C@H]1CCc3cc(O)c(O)cc3[C@H]21] |
| trans-(6a,12b)-5,6,6a,7,8,12b-hexahydrobenzo[a]phenanthridine-2,3,10,11-tetraol | 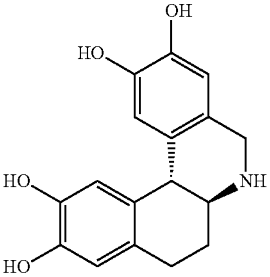 [SMILES: Oc1cc2c(cc1O)[C@@H]1c3cc(O)c(O)cc3CN[C@H]1CC2] |

In some embodiments, the compound is a compound selected from Table 2, or a pharmaceutically acceptable salt or solvate thereof.

TABLE 2

| Name | Structure |
| --- | --- |
| 4-(1,2,3,4-tetrahydro-2,7-naphthyridin-4-yl)benzene-1,2-diol | 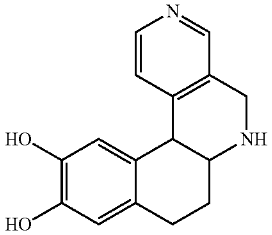 [SMILES: Oc1cc2c(cc1O)C1c3ccncc3CNC1CC2] |
| 4-(6-methyl-1,2,3,4-tetrahydro-2,7-naphthyridin-4-yl)benzene-1,2-diol | 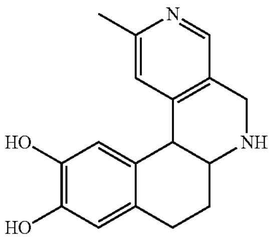 [SMILES: Cc1cc2c(cn1)CNC1CCc3cc(O)c(O)cc3C21] |
| 4-(1,2,3,4-tetrahydro-2,6-naphthyridin-4-yl)benzene-1,2-diol | 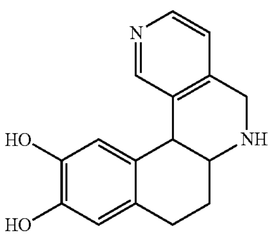 [SMILES: Oc1cc2c(cc1O)C1c3cnccc3CNC1CC2] |
| 4-(5,6,7,8-tetrahydro-1,7-naphthyridin-5-yl)benzene-1,2-diol | 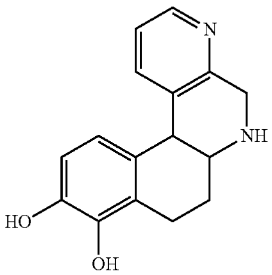 [SMILES: Oc1ccc2c(c1O)CCC1NCc3ncccc3C21] |
| 4-(3-methyl-5,6,7,8-tetrahydro-1,7-naphthyridin-5-yl)benzene-1,2-diol | 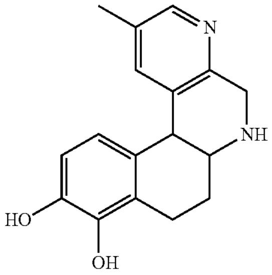 [SMILES: Cc1cnc2c(c1)C1c3ccc(O)c(O)c3CCC1NC2] |

In some embodiments, the compound is a compound of Table 3, or a pharmaceutically acceptable salt or solvate thereof.

TABLE 3

| Name | Structure |
| --- | --- |
| 3-chloro-5-(4,5,6,7-tetrahydrothieno[2,3-c]pyridin-4-yl)benzene-1,2-diol | 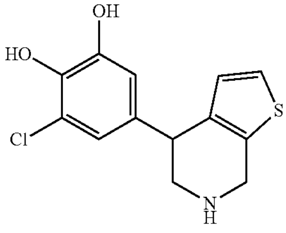 [SMILES: Oc1cc(C2CNCc3sccc32)cc(Cl)c1O] |
| 4-(3-chloro-4,5-dimethoxyphenyl)-4,5,6,7-tetrahydrothieno[2,3-c]pyridine | 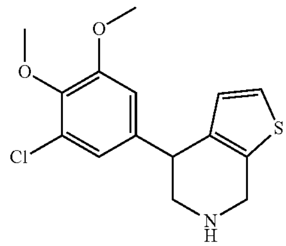 [SMILES: COc1cc(C2CNCc3sccc32)cc(Cl)c1OC] |
| (R)-4-(3-propyl-4,5,6,7-tetrahydrothieno[2,3-c]pyridin-4-yl)benzene-1,2-diol | 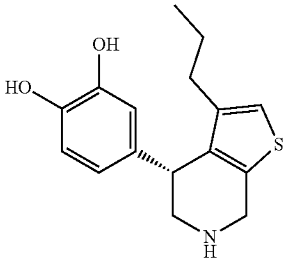 [SMILES: CCCc1csc2c1[C@@H](c1ccc(O)c(O)c1)CNC2] |
| (S)-4-(3-propyl-4,5,6,7-tetrahydrothieno[2,3-c]pyridin-4-yl)benzene-1,2-diol | 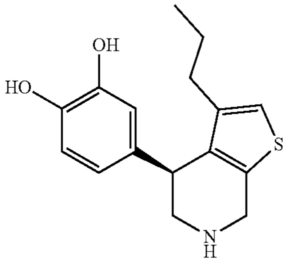 [SMILES: CCCc1csc2c1[C@H](c1ccc(O)c(O)c1)CNC2] |
| 3-chloro-2-methoxy-5-(4,5,6,7-tetrahydrothieno[2,3-c]pyridin-4-yl)phenol | 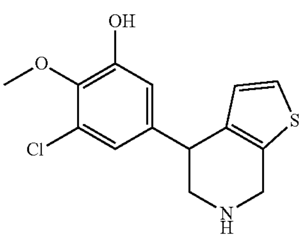 [SMILES: COc1c(O)cc(C2CNCc3sccc32)cc1Cl] |
| 4-(3,4-dimethoxyphenyl)-3-propyl-4,5,6,7-tetrahydrothieno[2,3-c]pyridine | 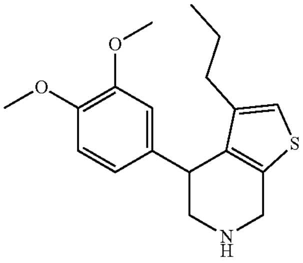 [SMILES: CCCc1csc2c1C(c1ccc(OC)c(OC)c1)CNC2] |

TABLE 3-continued

| Name | Structure |
|---|---|
| 4-(3-propyl-4,5,6,7-tetrahydrothieno[2,3-c]pyridin-4-yl)benzene-1,2-diol | 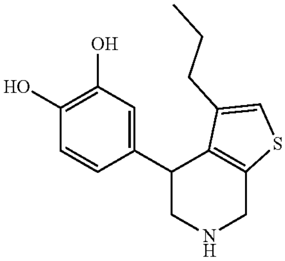 [SMILES: CCCc1csc2c1C(c1ccc(O)c(O)c1)CNC2] |
| (R)-4-(4,5,6,7-tetrahydrothieno[2,3-c]pyridin-4-yl)benzene-1,2-diol | 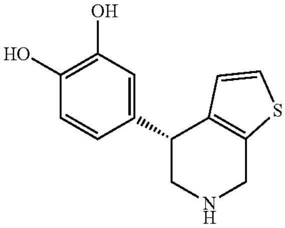 [SMILES: Oc1ccc([C@H]2CNCc3sccc32)cc1O] |
| (S)-4-(4,5,6,7-tetrahydrothieno[2,3-c]pyridin-4-yl)benzene-1,2-diol | 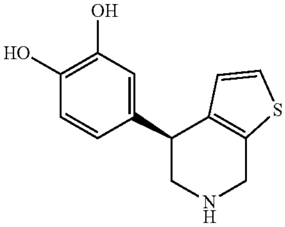 [SMILES: Oc1ccc([C@@H]2CNCc3sccc32)cc1O] |
| 4-(6-methyl-4,5,6,7-tetrahydrothieno[2,3-c]pyridin-4-yl)benzene-1,2-diol | 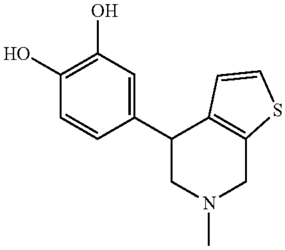 [SMILES: CN1Cc2sccc2C(c2ccc(O)c(O)c2)C1] |
| 4-(3,4-dimethoxyphenyl)-4,5,6,7-tetrahydrothieno[2,3-c]pyridine | 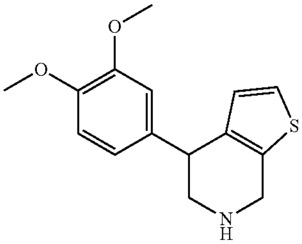 [SMILES: COc1ccc(C2CNCc3sccc32)cc1OC] |

Additional compounds include:

(6aR,12bS)-(+)-10, 11-dihydroxy-5, 6, 6a, 7, 8, 12b-hexahydro-benzo[a]phenanthridine;

(6aS,12bR)-(−)-10, 11-dihydroxy-5, 6, 6a, 7, 8, 12b-hexahydro-benzo[a]phenanthridine;

(6aR,12bS)-(+)-2-methyl-10,11-dihydroxy-5,6,6a,7,8,12b-hexa-hydrobenzo[a]phenanthridine;

(6aS,12bR)-(−)-2-methyl-10,11-dihydroxy-5,6,6a,7,8,12b-hexa-hydrobenzo[a]phenanthridine;

(6aR,12bS)-(+)-3-methyl-10,11-dihydroxy-5,6,6a,7,8,12b-hexa-hydrobenzo[a]phenanthridine;

(6aS,12bR)-(−)-3-methyl-10,11-dihydroxy-5,6,6a,7,8,12b-hexa-hydrobenzo[a]phenanthridine;

(6aR,12bS)-(+)-4-methyl-10,11-dihydroxy-5,6,6a,7,8,12b-hexa-hydrobenzo[a]phenanthridine;

(6aS,12bR)-(−)-4-methyl-10,11-dihydroxy-5,6,6a,7,8,12b-hexa-hydrobenzo[a]phenanthridine;

(6aR,12bS)-(+)-2-phenyl-10,11-dihydroxy-5,6,6a,7,8,12b-hexa-hydrobenzo[a]phenanthridine;

(6aS,12bR)-(−)-2-phenyl-10,11-dihydroxy-5,6,6a,7,8,12b-hexa-hydrobenzo[a]phenanthridine;

(6aR,12bS)-(+)-N-methyl-2-methyl-10,11-dihydroxy-5,6,6a,7,8,12b-hexahydrobenzo[a]phenanthridine;

(6aS,12bR)-(−)-N-methyl-2-methyl-10,11-dihydroxy-5,6,6a,7,8,12b-hexahydrobenzo[a]phenanthridine;

(6aR,12bS)-(+)-N-propyl-3-methyl-10,11-dihydroxy-5,6,6a,7,8,12b-hexahydrobenzo[a]phenanthridine;

(6aS,12bR)-(−)-N-propyl-3-methyl-10,11-dihydroxy-5,6,6a,7,8,12b-hexahydrobenzo[a]phenanthridine;

(6aR,12bS)-(+)-2-ethyl-10,11-dihydroxy-5,6,6a,7,8,12b-hexa-hydrobenzo[a]phenanthridine;

(6aS,12bR)-(−)-2-ethyl-10,11-dihydroxy-5,6,6a,7,8,12b-hexa-hydrobenzo[a]phenanthridine;

(6aR,12bS)-(+)-3-ethyl-10,11-dihydroxy-5,6,6a,7,8,12b-hexa-hydrobenzo[a]phenanthridine;

(6aS,12bR)-(−)-3-ethyl-10,11-dihydroxy-5,6,6a,7,8,12b-hexa-hydrobenzo[a]phenanthridine;

(6aR,12bS)-(+)-3,4-dimethyl-10-bromo-11-hydroxy-5,6,6a,7,8,12b-hexahydrobenzo[a]phenanthridine;

(6aS,12bR)-(−)-3,4-dimethyl-10-bromo-11-hydroxy-5,6,6a,7,8,12b-hexahydrobenzo[a]phenanthridine;

(6aR,12bS)-(+)-N-propyl-2,3-dimethyl-10,11-dihydroxy-5,6,6a,7,8,12b-hexahydrobenzo[a]phenanthridine;

(6aS,12bR)-(−)-N-propyl-2,3-dimethyl-10,11-dihydroxy-5,6,6a,7,8,12b-hexahydrobenzo[a]phenanthridine;

(6aR,12bS)-(+)-N-ethyl-3,4-dimethyl-10-bromo-11-hydroxy-5,6,6a,7,8,12b-hexahydrobenzo[a]phenanthridine;

(6aS,12bR)-(−)-N-ethyl-3,4-dimethyl-10-bromo-11-hydroxy-5,6,6a,7,8,12b-hexahydrobenzo[a]phenanthridine;

(6aR,12bS)-(+)-N-methyl-4-ethyl-10,11-dihydroxy-5,6,6a,7,8,12b-hexahydrobenzo[a]phenanthridine;

(6aS,12bR)-(−)-N-methy 1-4-ethyl-10,11-dihydroxy-5,6,6a,7,8,12b-hexahydrobenzo[a]phenanthridine;

(6aR,12bS)-(+)-N-butyl-3,10,11-trihydroxy-5,6,6a,7,8,12b-hexahydrobenzo[a]phenanthridine;

(6aS,12bR)-(−)-N-butyl-3,10,11-trihydroxy-5,6,6a,7,8,12b-hexahydrobenzo[a]phenanthridine;

(6aR,12bS)-(+)-2-methyl-3,10,11-trihydroxy-5,6,6a,7,8,12b-hexahydrobenzo[a]phenanthridine;

(6aS,12bR)-(−)-2-methyl-3,10,11-trihydroxy-5,6,6a,7,8,12b-hexahydrobenzo[a]phenanthridine;

(6aR,12bS)-(+)-3-fluoro-10,11-dihydroxy-5,6,6a,7,8,12b-hexa-hydrobenzo[a]phenanthridine;

(6aS,12bR)-(−)-3-fluoro-10,11-dihydroxy-5,6,6a,7,8,12b-hexa-hydrobenzo[a]phenanthridine;

(6aR,12bS)-(+)-10-bromo-2,11-dihydroxy-5,6,6a,7,8,12b-hexa-hydrobenzo[a]phenanthridine;

(6aS,12bR)-(−)-10-bromo-2,11-dihydroxy-5,6,6a,7,8,12b-hexa-hydrobenzo[a]phenanthridine;

(6aR,12bS)-(+)-2-bromo-10,11-dihydroxy-5,6,6a,7,8,12b-hexa-hydrobenzo[a]phenanthridine;

(6aS,12bR)-(−)-2-bromo-10,11-dihydroxy-5,6,6a,7,8,12b-hexa-hydrobenzo[a]phenanthridine;

(6aR,12bS)-(+)-3-bromo-10-methoxy-11-hydroxy-5,6,6a,7,8,12b-hexahydrobenzo[a]phenanthridine;

(6aS,12bR)-(−)-3-bromo-10-methoxy-11-hydroxy-5,6,6a,7,8,12b-hexahydrobenzo[a]phenanthridine;

(6aR,12bS)-(+)-4-bromo-10-methoxy-11-hydroxy-5,6,6a,7,8,12b-hexahydrobenzo[a]phenanthridine;

(6aS,12bR)-(−)-4-bromo-10-methoxy-11-hydroxy-5,6,6a,7,8,12b-hexahydrobenzo[a]phenanthridine;

(6aR,12bS)-(+)-2-methyl-3-bromo-10-methoxy-11-hydroxy-5,6,6a,7,13,12b-hexahydrobenzo[a]phenanthridine;

(6aS,12bR)-(−)-2-methyl-3-bromo-10-methoxy-11-hydroxy-5,6,6a,7,8,12b-hexahydrobenzo[a]phenanthridine;

(6aR,12bS)-(+)-N-methyl-2-fluoro-10,11-dihydroxy-5,6,6a,7,8,12b-hexahydrobenzo[a]phenanthridine;

(6aS,12bR)-(−)-N-methy 1-2-fluoro-10,11-dihydroxy-5,6,6a,7,8,12b-hexahydrobenzo[a]phenanthridine;

(6aR,12bS)-(+)-N-methyl-3-fluoro-10,11-dihydroxy-5,6,6a,7,8,12b-hexahydrobenzo[a]phenanthridine;

(6aS,12bR)-(−)-N-methyl-3-fluoro-10,11-dihydroxy-5,6,6a,7,8,12b-hexahydrobenzo[a]phenanthridine;

(6aR,12bS)-(+)-N-methyl-4-fluoro-10,11-dihydroxy-5,6,6a,7,8,12b-hexahydrobenzo[a]phenanthridine;

(6aS,12bR)-(−)-N-methy 1-4-fluoro-10,11-dihydroxy-5,6,6a,7,8,12b-hexahydrobenzo[a]phenanthridine;

(6aR,12bS)-(+)-N-ethyl-10-fluoro-3,11-dihydroxy-5,6,6a,7,8,12b-hexahydrobenzo[a]phenanthridine;

(6aS,12bR)-(−)-N-ethyl-10-fluoro-3,11-dihydroxy-5,6,6a,7,8,12b-hexahydrobenzo[a]phenanthridine;

(6aR,12bS)-(+)-N-ethyl-2-methyl-10-fluoro-3,11-dihydroxy-5,6,6a,7,8,12b-hexahydrobenzo[a]phenanthridine;

(6aS,12bR)-(−)-N-ethyl-2-methyl-10-fluoro-3,11-dihydroxy-5,6,6a,7,8,12b-hexahydrobenzo[a]phenanthridine;

(6aR,12bS)-(+)-N-ethyl-2-methoxy-4-methyl-10-fluoro-11-hydroxy-5,6,6a,7,8,12b-hexahydrobenzo[a]phenanth-ridine; (6aS,12bR)-(−)-N-ethyl-2-methoxy-4-methyl-10-fluoro-11-hydroxy-5,6,6a,7,8,12b-hexahydrobenzo[a]phenanthridine;

(6aR,12bS)-(+)-N-propyl-3-methoxy-10-chloro-11-hydroxy-5,6,6a,7,8,12b-hexahydrobenzo[a]phenanthridine;

(6aS,12bR)-(−)-N-propyl-3-methoxy-10-chloro-11-hydroxy-5,6,6a,7,8,12b-hexahydrobenzo[a]phenanthridine;

(6aR,12bS)-(+)-N-propyl-4-methoxy-3-methyl-10-chloro-11-hydroxy-5,6,6a,7,8,12b-hexahydrobenzo[a]phenanthridine;

(6aS,12bR)-(−)-N-propyl-4-methoxy-3-methyl-10-chloro-11-hydroxy-5,6,6a,7,8,12b-hexahydrobenzo[a]phenanthridine;

(6aR,12bS)-(+)-N-propyl-2-ethoxy-10,11-dihydroxy-5,6,6a,7,8,12b-hexahydrobenzo[a]phenanthridine;

(6aS,12bR)-(−)-N-propyl-2-ethoxy-10,11-dihydroxy-5,6,6a,7,8,12b-hexahydrobenzo[a]phenanthridine;

(6aR,12bS)-(+)-N-propy 1-4,10,11-trihydroxy-5,6,6a,7,8,12b-hexahydrobenzo[a]phenanthridine;

(6aS,12bR)-(−)-N-propyl-4,10,11-trihydroxy-5,6,6a,7,8,12b-hexahydrobenzo[a]phenanthridine;

(6aR,12bS)-(+)-N-butyl-2-methyl-10,11-dihydroxy-5,6,6a,7,8,12b-hexahydrobenzo[a]phenanthridine;

(6aS,12bR)-(−)-N-butyl-2-methyl-10,11-dihydroxy-5,6,6a,7,8,12b-hexahydrobenzo[a]phenanthridine;

(6aR,12bS)-(+)-N-butyl-4-methyl-3,10,11-trihydroxy-5,6,6a,7,8,12b-hexahydrobenzo[a]phenanthridine;

(6aS,12bR)-(−)-N-butyl-4-methyl-3,10,11-trihydroxy-5,6,6a,7,8,12b-hexahydrobenzo[a]phenanthridine;

(6aR,12bS)-(+)-N-butyl-3-chloro-2,10,11-trihydroxy-5,6,6a,7,8,12b-hexahydrobenzo[a]phenanthridine;

(6aS,12bR)-(−)-N-butyl-3-chloro-2,10,11-trihydroxy-5,6,6a,7,8,12b-hexahydrobenzo[a]phenanthridine;

(6aR,12bS)-(+)-N-butyl-2-chloro-3,10,11-trihydroxy-5,6,6a,7,8,12b-hexahydrobenzo[a]phenanthridine;

(6aS,12bR)-(−)-N-butyl-2-chloro-3,10,11-trihydroxy-5,6,6a,7,8,12b-hexahydrobenzo[a]phenanthridine;

(6aR,12bS)-(+)-N-butyl-3-methyl-10-iodo-11-hydroxy-5,6,6a,7,8,12b-hexahydrobenzo[a]phenanthridine;

(6aS,12bR)-(−)-N-butyl-3-methyl-10-iodo-11-hydroxy-5,6,6a,7,8,12b-hexahydrobenzo[a]phenanthridine.

Further Forms of Compounds

In some aspects, a compound disclosed herein possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, “Enantiomers, Racemates and Resolutions”, John Wiley And Sons, Inc., 1981. In one aspect, stereoisomers are obtained by stereoselective synthesis.

In some embodiments, compounds described herein are prepared as prodrugs. A “prodrug” refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the “prodrug”) to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews,* 56:53-102, 2004; Aesop Cho, "Recent Advances in Oral Prodrug Discovery", *Annual Reports in Medicinal Chemistry, Vol.* 41, 395-407, 2006; T. Higuchi and V. Stella, *Pro-drugs as Novel Delivery Systems*, Vol. 14 of the A.C.S. Symposium Series).

In some embodiments, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g., with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine, chlorine, and iodine such as, for example, $^{2}H$, $^{3}H$, $^{13}C$, $^{14}C$, $^{15}N$, $^{18}O$, $^{17}O$ $^{35}S$, $^{18}F$, $^{36}Cl$, and $^{125}I$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound disclosed herein with acids. Pharmaceutically acceptable salts are also obtained by reacting a compound disclosed herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g., lithium, sodium, potassium), an alkaline earth ion (e.g., magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Methods of Synthesis

In some embodiments, the syntheses of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure).

DEFINITIONS

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed invention.

The terms below, as used herein, have the following meanings, unless indicated otherwise:

"Oxo" refers to the =O substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_5$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. Unless stated otherwise specifically in the specification, an alkyl group may be optionally substituted as described below.

"Alkylene" refers to a straight or branched divalent hydrocarbon chain linking the rest of the molecule to a radical group. In some embodiments, the alkylene is $—CH_2—$, $—CH_2CH_2—$, or $—CH_2CH_2CH_2—$. In some embodiments, the alkylene is $—CH_2—$. In some embodiments, the alkylene is $—CH_2CH_2—$. In some embodiments, the alkylene is $—CH_2CH_2CH_2—$.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkyl" refers to an alkyl radical as described above where one or more carbon atoms of the alkyl is replaced with a O, N (i.e., NH, N-alkyl) or S atom. "Heteroalkylene" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to $—OCH_2OMe$, $—OCH_2CH_2OMe$, or $—OCH_2CH_2OCH_2CH_2NH_2$. Representative heteroalkylene groups include, but are not limited to $—OCH_2CH_2O—$, $—OCH_2CH_2OCH_2CH_2O—$, or $—OCH_2CH_2OCH_2CH_2OCH_2CH_2O—$.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to $—CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

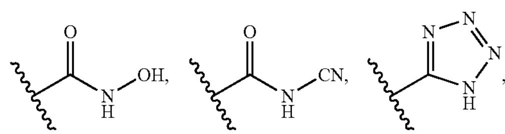

-continued

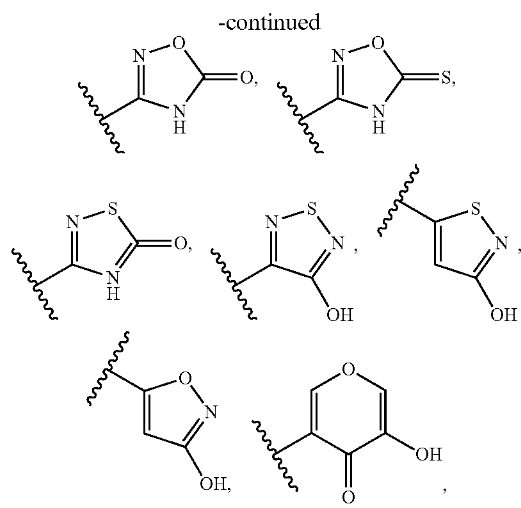

and the like.

"Cycloalkyl" refers to a monocyclic or polycyclic non-aromatic radical, wherein each of the atoms forming the ring (i.e., skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. In some embodiments, the monocyclic cycloalkyl is cyclopentyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclic ring or a heteroaryl ring, any carbon atom on the existing ring structure which becomes part of the fused heterocyclic ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2$H, —$CO_2$alkyl, nitro, and amino, including mono- and di-substituted amino groups (e.g., —$NH_2$, —NHR, —$NR_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2$H, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (═O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

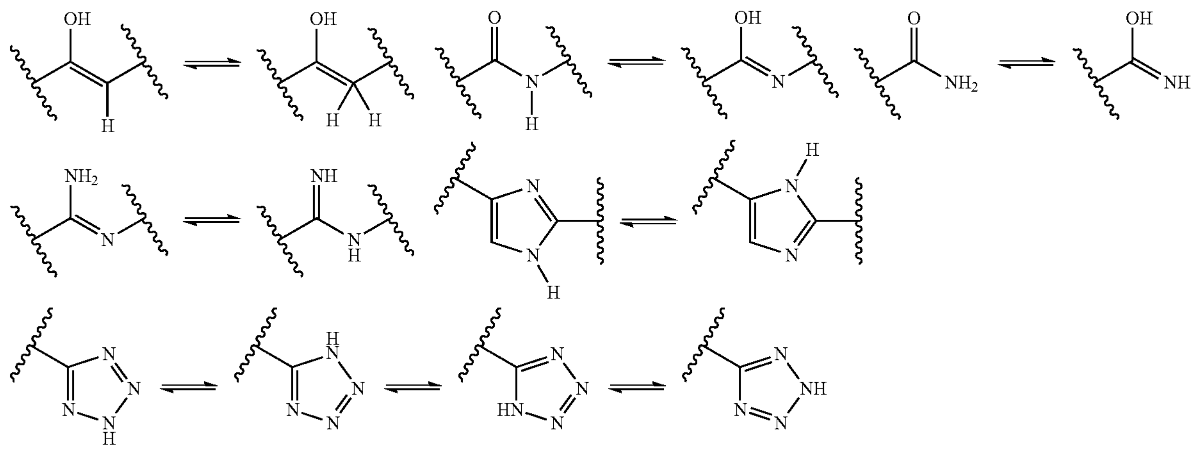

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999);

and *Remington: The Science and Practice of Pharmacy*, 20th Edition, 2003, Gennaro, Ed., Lippincott, Williams & Wilkins).

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound of Formula (I) and a co-agent, are both administered to a patient simultaneously in the form of a single entity or dosage. The term "non-fixed combination" means that the active ingredients, e.g., a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In one aspect, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound disclosed herein with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds disclosed herein are administered orally.

In some embodiments, the compounds disclosed herein are administered topically. In such embodiments, the compound disclosed herein is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds disclosed herein are administered topically to the skin.

In another aspect, the compounds disclosed herein are administered by inhalation.

In another aspect, the compounds disclosed herein are formulated for intranasal administration. Such formulations include nasal sprays, nasal mists, and the like.

In another aspect, the compounds disclosed herein are formulated as eye drops.

In any of the aforementioned aspects are further embodiments in which the effective amount of the compound disclosed herein is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound disclosed herein, including further embodiments in which (i) the compound is administered once; (ii) the compound is administered to the mammal multiple times over the span of one day; (iii) the compound is administered continually; or (iv) the compound is administered continuously.

In any of the aforementioned aspects are further embodiments comprising multiple administrations of the effective amount of the compound disclosed herein, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound disclosed herein is temporarily suspended or the dose of the compound being administered is temporarily reduced; at the end of the drug holiday, dosing of the compound is resumed. In one embodiment, the length of the drug holiday varies from 2 days to 1 year.

In certain embodiments, the compound disclosed herein is administered in a local rather than systemic manner.

In some embodiments, the compound disclosed herein is administered topically. In some embodiments, the compound disclosed herein is administered systemically.

In some embodiments, the pharmaceutical formulation is in the form of a tablet. In other embodiments, pharmaceutical formulations of the compounds disclosed herein are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound disclosed herein is formulated for use as an aerosol, a mist or a powder.

For buccal or sublingual administration, the compositions may take the form of tablets, lozenges, or gels formulated in a conventional manner.

In some embodiments, compounds disclosed herein are prepared as transdermal dosage forms.

In one aspect, a compound disclosed herein is formulated into a pharmaceutical composition suitable for intramuscular, subcutaneous, or intravenous injection.

In some embodiments, the compound disclosed herein is be administered topically and can be formulated into a variety of topically administrable compositions, such as solutions, suspensions, lotions, gels, pastes, medicated sticks, balms, creams or ointments.

In some embodiments, the compounds disclosed herein are formulated in rectal compositions such as enemas, rectal gels, rectal foams, rectal aerosols, suppositories, jelly suppositories, or retention enemas.

Methods of Dosing and Treatment Regimens

In one aspect, the compounds disclosed herein are used in the preparation of medicaments for the treatment of diseases or conditions described herein. In addition, a method for treating any of the diseases or conditions described herein in a subject in need of such treatment, involves administration of pharmaceutical compositions that include at least one compound disclosed herein or a pharmaceutically acceptable salt, active metabolite, prodrug, or solvate thereof, in therapeutically effective amounts to said subject.

In certain embodiments, the compositions containing the compound disclosed herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds disclosed herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound disclosed herein in combination with another therapeutic agent.

In one specific embodiment, a compound disclosed herein is co-administered with a second therapeutic agent, wherein the compound disclosed herein and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

Methods of Treatment

In some embodiments, the present disclosure provides a method of agonizing a G protein coupled receptor in a cell, the method comprising contacting the cell with any one of compounds described herein, or a pharmaceutically acceptable salt thereof. In some embodiments, the present disclosure provides a method of promoting YAP phosphorylation in a cell, the method comprising contacting the cell with any one of compounds described herein, or a pharmaceutically acceptable salt thereof. In some embodiments, agonism of the G protein coupled receptor results in YAP/TAZ phosphorylation and subsequent degradation. In some embodiments, the present disclosure provides a method of inhibiting YAP/TAZ function in a cell (e.g., inhibiting expression of a profibrotic gene in a cell), the method comprising contacting the cell with any one of the compounds of the present disclosure, or a pharmaceutically acceptable salt thereof. In some embodiments, agonism of the G protein coupled receptor results in inhibition of YAP/TAZ function in a cell and subsequent inhibition of expression of profibrotic genes in the cell. In some embodiments, inhibiting YAP/TAZ function in a cell results in prevention of accumulation of extracellular matrix in a tissue. In some embodiments, agonism of G protein coupled receptor reverses fiber formation and extracellular matrix accumulation. In some embodiments, the fiber formation is induced by trauma or tissue injury. Normally cells generate just the right amount of tissue to replace old tissue or repair damage. Excessive connective tissue generation (e.g., in response to trauma or injury) results in pathological accumulation of fibrotic tissue (e.g., extracellular matrix proteins) leading to organ or tissue thickening and scarring.

In some embodiments, the present disclosure provides a method of treating a disease or condition in a mammal that would benefit from inhibition of YAP/TAZ activity, comprising administering to the mammal a compound as disclosed herein, or a pharmaceutically acceptable salt or solvate thereof.

In some embodiments, the present disclosure provides a method of treating or preventing a fibrotic pathology in a subject, the method comprising administering to the subject in need thereof a therapeutically effective amount of any one of the compounds described herein, or a pharmaceutically acceptable salt thereof. In some embodiments, the subject in need of treatment of fibrotic pathology is diagnosed with fibrotic pathology by a treating physician.

In some embodiments, the fibrotic pathology is interstitial lung disease (ILD). In some embodiments, fibrotic pathology is lung tissue fibrosis, e.g., pulmonary fibrosis (PF) or idiopathic pulmonary fibrosis (IPF). Despite the name, cystic fibrosis is not considered an interstitial lung disease or predominantly a fibrotic pathology. Cystic fibrosis results from impaired ion transport, mucus dysfunction, and failure to effectively clear pathogens from the airways, which eventually results in scarring of the airways and lungs.

In some embodiments, fibrotic pathology is a liver tissue fibrosis, e.g., cirrhosis or biliary atresia. In some embodiments, fibrotic pathology is a heart tissue fibroses (cardiac fibrosis), e.g., atrial fibrosis, endomyocardial fibrosis, or post-myocardial infarction scarring. In some embodiments, fibrotic pathology is a brain tissue fibrosis, e.g., glial scar. In some embodiments, fibrotic pathology is arterial stiffness, arthrofibrosis (knee, shoulder, elbow, or other joints), chronic kidney disease and fibrosis, liver fibrosis, nonalcoholic fatty liver, nonalcoholic steatohepatitis, Crohn's disease (intestinal scarring), Dupuytren's contracture (scar tissue in hands or fingers), skin tissue fibrosis, e.g., keloid (a scar on the skin), mediastinal fibrosis (soft tissue of the mediastinum), Peyronie's disease (scar in a penial tissue), nephrogenic systemic fibrosis, progressive massive fibrosis, retroperitoneal fibrosis (scar on the soft tissue of the retroperitoneum) or adhesive capsulitis.

In some embodiments, the subject in need of prevention of fibrotic pathology is diagnosed with tissue trauma or injury by a treating physician. Suitable examples of tissue injury include injury caused by inhaled substances (e.g., silica or asbestos), drug-induced injury (injury caused by an antibiotic or an anticancer drug), tissue injury caused by autoimmune disease (e.g., rheumatoid arthritis, sclerosis, such as systemic sclerosis, lupus), injury caused by infection (e.g., tuberculosis, pneumonia, respiratory virus), or sarcoidosis.

EXAMPLES

Preparation of Compounds

Abbreviations

CAN: Ceric ammonium nitrate
DCM: Dichloromethane
DIEA: Diisopropylethylamine
DMF: Dimethyl formamide
DMSO: Dimethyl sulfoxide
EA: Ethyl acetate
ESI Electrospray ionization HATU: 1-[Bis(dimethylamino)methylene]-1H-1,2,3-triazolo[4,5-b]pyridinium 3-oxid hexafluorophosphate
HPLC: High performance liquid chromatography
HRMS: High resolution mass spectrometry
h or hr(s): Hour(s)
MeOH: Methanol
Ms: Mesyl, or methanesulfonyl
min(s): Minutes
m/z: Mass-to-charge ratio
1H NMR: Proton nuclear magnetic resonance
13C NMR: Carbon nuclear magnetic resonance
PE: Petroleum ether
rt: Room temperature
TFA: Trifluoroacetic acid

Examples 1 and 2: Synthesis of (6aR,12bR)-5,6,6a,7,8,12b-hexahydrobenzo[a]phenanthridine-3,4,10,11-tetraol (Compound 1) and (6aR,12bS)-5,6,6a,7,8,12b-hexahydrobenzo[a]phenanthridine-3,4,10,11-tetraol (Compound 2)

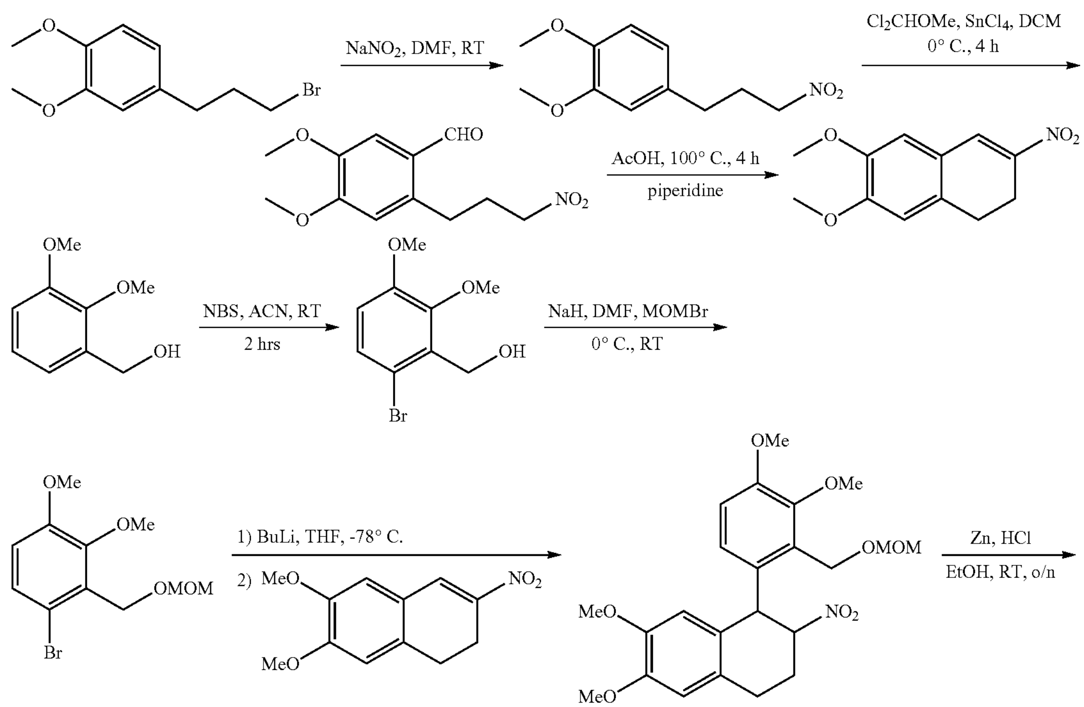

-continued

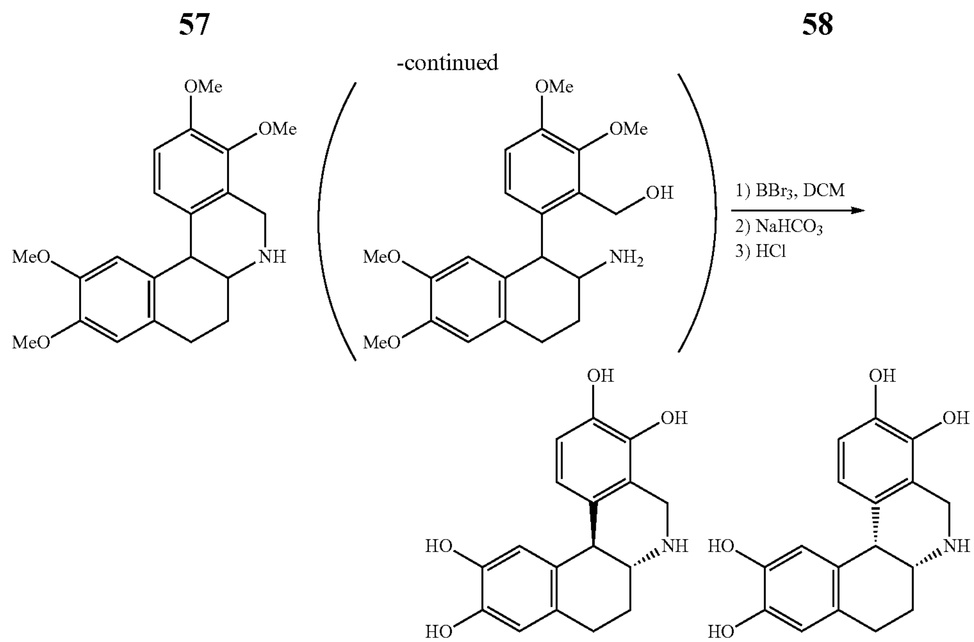

Step 1

To a solution of 3-(3,4-dimethoxyphenyl)propanoic acid (4.2 g, 20 mmol) in THF (20 mL) was added $BH_3$-DMS (10M, 2.2 mL, 22 mmol) and the reaction was stirred at 0° C. under $N_2$ for 4 hrs. The reaction mixture was quenched with MeOH (5 mL) and concentrated to dryness in vacuum. After that, the dry mixture was poured into $H_2O$ (100 mL) and extracted with DCM (50 mL×3). The combined DCM layers were washed with brine (100 mL), dried over $Na_2SO_4$ and concentrated to give 3-(3,4-dimethoxyphenyl)propan-1-ol (3.6 g, yield: 92%) as a colorless oil.

Step 2

To a solution of 3-(3,4-dimethoxyphenyl)propan-1-ol (3.6 g, 18.36 mmol) and $CBr_4$ (6.09 g, 18.36 mmol) in DCM (20 mL) was added $PPh_3$ (4.7 g, 18 mmol) and the reaction was stirred at 0° C. for 4 hrs. The reaction mixture was poured into $H_2O$ (100 mL) and extracted with DCM (50 mL×3). The combined DCM layers were washed with brine (150 mL), dried over $Na_2SO_4$ and concentrated to dryness in vacuum. The residue was purified by silica gel column (PE/EA=7/1) to give 4-(3-bromopropyl)-1,2-dimethoxybenzene (4 g, yield: 84%) as a colorless oil.

Step 3

A solution of 4-(3-bromopropyl)-1,2-dimethoxybenzene (4 g, 15.44 mmol) and $NaNO_2$ (1.38 g, 20.07 mmol) in DMF (20 mL) was stirred at 0° C. overnight. The reaction mixture was poured into $H_2O$ (100 mL) and extracted with DCM (50 mL×3). The combined DCM layers were washed with brine (150 mL), dried over $Na_2SO_4$ and concentrated to dryness in vacuum. The residue was purified by silica gel column (PE/EA=3/1) to give 1,2-dimethoxy-4-(3-nitropropyl)benzene (1.44 g, yield: 41%) as a colorless oil.

Step 4

To a solution of 1,2-dimethoxy-4-(3-nitropropyl)benzene (1.4 g, 6.22 mmol) in dry DCM (10 mL) was added $SnCl_4$ (0.73 mL, 6.22 mmol) and $Cl_2CHOMe$ (0.56 mL, 6.22 mmol). The reaction was then stirred at 0° C. for 4 hrs. The reaction mixture was poured into $H_2O$ (70 mL) and extracted with DCM (30 mL×3). The combined DCM layers were washed with 2 M (HCl) (10 mL), dried over $Na_2SO_4$ and concentrated to give 4,5-dimethoxy-2-(3-nitropropyl) benzaldehyde (1.54 g, yield: 94%) as a brown solid.

Step 5

To a solution of 4,5-dimethoxy-2-(3-nitropropyl)benzaldehyde (1.54 g, 6.08 mmol) in AcOH (10 mL) was added piperidine (1.2 mL, 12.1 mmol) and the reaction was stirred at 100° C. for 4 hrs. The reaction mixture was poured into $H_2O$ (70 mL) and extracted with DCM (30 mL×3). The combined DCM layers were washed with brine (100 mL), dried over $Na_2SO_4$ and concentrated to dryness in vacuum. The residue was purified by silica gel column (PE/EA=3/1) to give 6,7-dimethoxy-3-nitro-1,2-dihydronaphthalene (1.26 g, yield: 88%) as a yellow solid.

Step 6

To a solution of (2,3-dimethoxyphenyl)methanol (6.72 g, 40 mmol) in MeCN (100 mL) was added NBS (7.6 g, 40.2 mmol) in one portion. The reaction was stirred at room temperature for 2 hrs. The reaction was monitored by TLC. The reaction solution was concentrated under reduced pressure. The residue was dissolved in EA (100 mL) and washed with saturated $NaHCO_3$ solution (100 mL×3). The organic layer was dried over $Na_2SO_4$ and concentrated to give (6-bromo-2,3-dimethoxyphenyl)methanol (10 g, yield: quantitative) as a yellow solid. $^1$HNMR (400 MHz, $CDCl_3$): δ=7.27 (d, J=7.6 Hz, 1H), 6.77 (d, J=8.8 Hz, 1H), 4.83 (s, 2H), 3.90 (s, 3H), 3.86 (s, 3H).

Step 7

To a solution of (6-bromo-2,3-dimethoxyphenyl)methanol (8.7 g, 35.2 mmol) in DMF (70 mL) was added NaH (1.7 g, 60%, 42.3 mmol) at 0° C. under $N_2$. The reaction was stirred 0° C. for 30 mins and MOMBr (3.4 mL, 42.3 mmol) was added. The reaction was then stirred for 2 hrs at room temperature. The reaction solution was poured into water (350 mL) and extracted with EA (200 mL). The organic layer was washed with water (200 mL) and brine (200 mL), dried over $Na_2SO_4$ and concentrated. The residue was purified by silica gel column (PE/EA=10/1) to give 1-bromo-3,4-dimethoxy-2-((methoxymethoxy)methyl)benzene (6.8 g, yield: 68%) as a colorless oil. $^1$HNMR (400 MHz, $CDCl_3$): δ=7.29 (d, J=9.2 Hz, 1H), 6.79 (d, J=9.2 Hz, 1H), 4.77 (s, 2H), 4.74 (s, 2H), 3.88 (s, 3H), 3.85 (s, 3H), 3.47 (s, 3H).

Step 8

To a solution of 1-bromo-3,4-dimethoxy-2-((methoxymethoxy)methyl)benzene (1.16 g, 4 mmol) in THE (20 mL) was added n-BuLi (2.5 M, 2 mL, 4.8 mmol) slowly at −78° C. under $N_2$. The reaction was stirred at −78° C. for 30 mins and 6,7-dimethoxy-3-nitro-1,2-dihydronaphthalene (940 mg, 4 mmol) was added. The reaction was warmed to room temperature slowly and stirred overnight. The reaction was quenched with saturated $NH_4Cl$ solution (4 mL) and partitioned between EA (50 mL) and water (50 mL). The organic layer was dried over $Na_2SO_4$ and concentrated. The residue was purified by silica gel column (PE/EA=2/1) to give 1-(3,4-dimethoxy-2-((methoxymethoxy)methyl)phenyl)-6,7-dimethoxy-2-nitro-1,2,3,4-tetrahydronaphthalene (840 mg, yield: 47%) as a yellow oil. $^1$HNMR (400 MHz, $CDCl_3$): δ=6.95-6.74 (m, 2H), 6.67-6.57 (m, 2H), 4.85-4.74 (m, 3H), 4.47-4.36 (m, 2H), 3.92-3.80 (m, 12H), 3.66-3.58 (m, 3H), 3.44-3.38 (m, 3H), 2.66-2.20 (m, 2H).

Step 9

To a solution of 1-(3,4-dimethoxy-2-((methoxymethoxy)methyl)phenyl)-6,7-dimethoxy-2-nitro-1,2,3,4-tetrahydronaphthalene (840 mg, 1.88 mmol) in EtOH (50 mL) was added conc. HCl (15 mL). The reaction was stirred at room temperature for 1 hr under $N_2$. Zn (powder, 953 mg, 14.6 mmol) was added and the reaction was stirred at 25° C. overnight. The reaction was concentrated. The residue was adjusted to pH=6 with $NH_4OH$ and purified by reverse phase column to give crude product. The crude product was further purified by prep-HPLC ($AcONH_4$) to give 3,4,10,11-tetramethoxy-5,6,6a,7,8,12b-hexahydrobenzo[a]phenanthridine (17 mg, yield: 3%) as a yellow solid.

$^1$HNMR (400 MHz, $CD_3OD$): δ=7.12 (d, J=8.4 Hz, 0.65H), 7.00 (d, J=8.4 Hz, 0.65H), 6.94 (d, J=8.4 Hz, 0.35H), 6.88 (d, J=8.8 Hz, 0.35H), 6.83 (s, 0.65H), 6.76 (s, 0.65H), 6.69 (s, 0.65H), 6.66 (s, 0.35H), 4.27-4.18 (m, 2H), 4.06-4.00 (m, 2H), 3.87-3.58 (m, 13H), 2.89-2.74 (m, 2H), 2.20-2.09 (m, 1H), 1.76 (overlap, 1H). MS: m/z 356.0 ($M+H^+$).

Purification also give an intermediate (6-(2-amino-6,7-dimethoxy-1,2,3,4-tetrahydronaphthalen-1-yl)-2,3-dimethoxyphenyl)methanol (150 mg, yield: 21%) as a yellow solid.

$^1$HNMR (400 MHz, DMSO-$d_6$): δ=6.88 (d, J=8.4 Hz, 0.5H), 6.85 (d, J=8.8 Hz, 0.5H), 6.70 (s, 0.5H), 6.69 (s, 0.5H), 6.83 (s, 0.65H), 6.48 (d, J=8.4 Hz, 0.5H), 6.38 (d, J=8.8 Hz, 0.5H), 6.30 (s, 0.5H), 6.15 (s, 0.5H), 4.79 (d, J=11.2 Hz, 0.5H), 4.68-4.59 (m, 1.5H), 4.50 (d, J=6.4 Hz, 0.5H), 4.14 (d, J=6.8 Hz, 0.5H), 3.52 (s, 1.5H), 3.44 (s, 1.5H), 3.11 (overlap, 1H), 2.88-2.78 (m, 2H), 2.00-1.96 (m, 0.5H), 1.75-1.64 (m, 1.5H). MS: m/z 374.0 ($M+H^+$).

Step 10

To a solution of 3,4,10,11-tetramethoxy-5,6,6a,7,8,12b-hexahydrobenzo[a]phenanthridine (23 mg, 0.065 mmol) was added $BBr_3$ (0.06 mL, 0.65 mmol) slowly at −78° C. under $N_2$. The reaction was warmed to room temperature slowly and stirred overnight. MeOH (2 mL) was added under $N_2$ at 0° C. to quench the reaction. The resulting solution was concentrated. The residue was purified by prep-HPLC (TFA) to give two isomers.

Isomer 1 was made HCl salt by addition of 2N HCl and concentration to give HCl salt of trans-(6a,12b)-5,6,6a,7,8,12b-hexahydrobenzo[a]phenanthridine-3,4,10,11-tetraol (6 mg, yield: 27%) as a white solid. $^1$HNMR (400 MHz, $CD_3OD$): δ=6.86 (s, 3H), 6.68 (s, 1H), 4.45-4.37 (m, 2H), 4.09 (d, J=11.6 Hz, 1H), 3.06-2.77 (m, 3H), 2.32-2.27 (m, 1H), 1.96-1.90 (m, 1H). MS: m/z 300.1 ($M+H^+$).

Isomer 2 was further purified by prep-HPLC ($AcONH_4$) to give AcOH salt of cis-(6a,12b)-5,6,6a,7,8,12b-hexahydrobenzo[a]phenanthridine-3,4,10,11-tetraol (2.2 mg, yield: 9%) as a yellow solid. $^1$HNMR (400 MHz, $CD_3OD$): δ=6.80 (d, J=8.4 Hz, 1H), 6.64-6.60 (m, 3H), 4.26-4.17 (m, 2H), 4.01 (d, J=4.4 Hz, 1H), 3.86-3.82 (m, 1H), 2.81-2.77 (m, 2H), 2.28-2.23 (m, 1H), 1.96-1.84 (m, 4H). MS: m/z 300.1 ($M+H^+$).

Example 3: Synthesis of Trans-(6a,12b)-2-methyl-5,6,6a,7,8,12b-hexahydro-benzo[a]phenanthridine-3,10,11-triol (Compound 3)

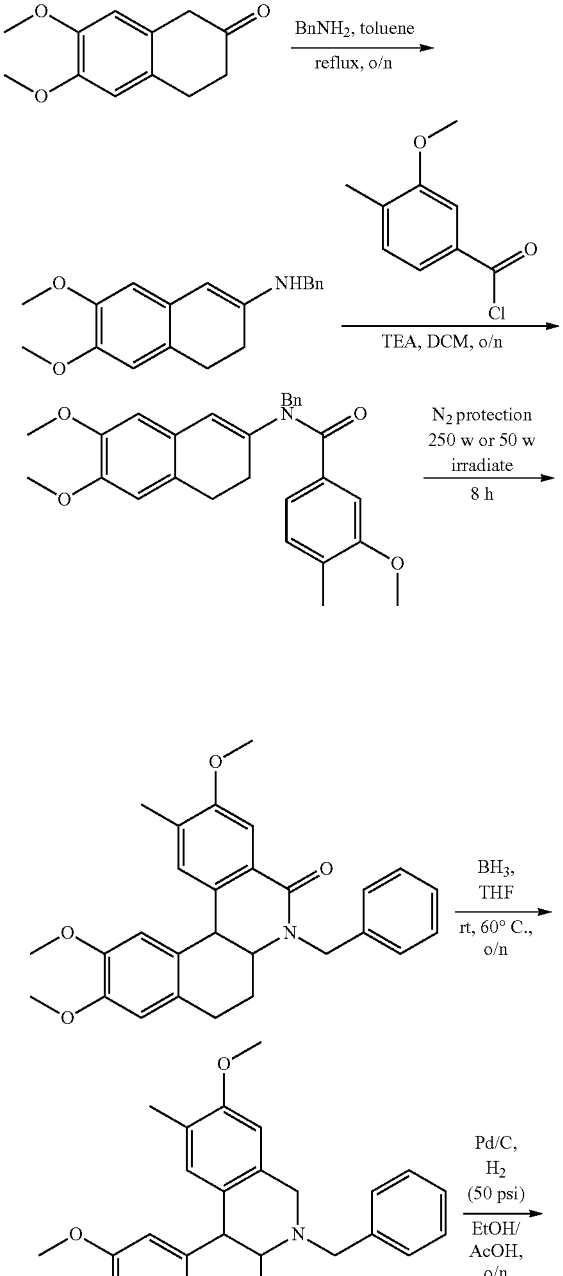

-continued

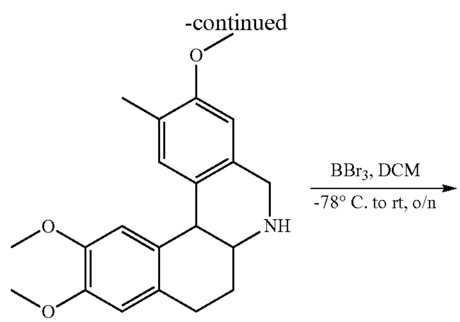

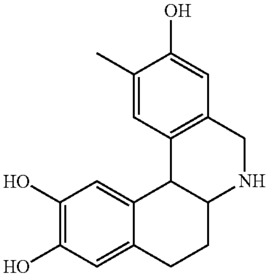

trans

Step 1

To a suspension of 6,7-dimethoxy-3,4-dihydronaphthalen-2(1H)-one (1.0 g, 4.85 mmol) in toluene (40 mL) was added $BnNH_2$ (571 mg, 5.33 mmol). The mixture was stirred at refluxing (150° C.) under $N_2$ with continuous water removal via a D-S apparatus for 16 hrs. The reaction mixture was concentrated to dryness to get N-benzyl-6,7-dimethoxy-3,4-dihydronaphthalen-2-amine (crude) which was used for the next step directly.

Step 2

To a suspension of 3-methoxy-4-methylbenzoic acid (1.61 g, 9.70 mmol) in DCM (20 mL) was added $(COCl)_2$ (2.46 g, 19.4 mmol) and DMF (1 drop). The mixture was stirred at room temperature for 1 hr. Then the mixture was concentrated to get 3-methoxy-4-methylbenzoyl chloride (crude) as a yellow oil.

To a suspension of N-benzyl-6,7-dimethoxy-3,4-dihydronaphthalen-2-amine (crude) and $Et_3N$ (1.96 g, 19.4 mmol) in DCM (20 mL) was added 3-methoxy-4-methylbenzoyl chloride (crude, ~4.85 mmol) in DCM (2 mL) under $N_2$. The mixture was stirred at room temperature for 16 hrs. The mixture was concentrated. The residue was treated with saturated $NaHCO_3$ solution (30 mL) to pH=8 and extracted with DCM (90 mL). The organic layer was dried over $Na_2SO_4$ and concentrated. The residue was purified by silica gel column (PE/EA=6/1 to 3/1), then by reverse phase column (MeCN/$H_2O$) to give N-benzyl-N-(6,7-dimethoxy-3,4-dihydronaphthalen-2-yl)-3-methoxy-4-methylbenzamide (300 mg, 14%) as a yellow solid. MS: m/z 444.5 ($M+H^+$).

Step 3

A solution of N-benzyl-N-(6,7-dimethoxy-3,4-dihydronaphthalen-2-yl)-3-methoxy-4-methylbenzamide (300 mg, 0.667 mmol) in THE (60 mL) was stirred in a quartz flask under $N_2$ while irradiating with a 500 w high-pressure Hg-Lamp for 8 hrs. The reaction was monitored by TLC and LCMS. The mixture was concentrated. The residue was triturated with MeOH (5 mL) to give trans-(6a,12b)-6-benzyl-3,10,11-trimethoxy-2-methyl-6,6a,7,8-tetrahydrobenzo[a]phenanthridin-5(12bH)-one (183 mg, 61%) as a yellow solid. $^1$HNMR (300 MHz, DMSO-$d_6$): δ=7.54 (s, 1H), 7.35 (t, J=7.8 Hz, 3H), 7.26 (t, J=7.5 Hz, 3H), 6.98 (s, 1H), 6.77 (s, 1H), 5.20 (d, J=16.2 Hz, 1H), 4.78 (d, J=16.2 Hz, 1H), 4.27 (d, J=11.4 Hz, 1H), 3.89 (s, 3H), 3.77 (d, J=8.1 Hz, 6H), 3.36 (s, 1H), 2.66 (s, 2H), 2.22 (s, 3H), 2.18-2.10 (m, 1H), 1.70-1.62 (m, 1H). MS: m/z 444.6 ($M+H^+$).

Step 4

To a solution of trans-(6a,12b)-6-benzyl-3,10,11-trimethoxy-2-methyl-6,6a,7,8-tetrahydrobenzo[a]phenanthridin-5(12bH)-one (180 mg, 0.406 mmol) in THE (20 mL) was added $BH_3$ (1.4 mL, 4.06 mmol) at room temperature under $N_2$. The reaction was stirred at 60° C. for 16 hrs. The reaction quenched with MeOH. To the resulting was added 6 M HCl (20 mL) and stirred at 60° C. for 1 hr. The mixture was treated with saturated $NaHCO_3$ solution to pH=8 and extracted with EA (60 mL). The organic layer was washed with brine (60 mL), dried over $Na_2SO_4$ and concentrated. The residue was purified by reverse phase column to give trans-(6a,12b)-6-benzyl-3,10,11-trimethoxy-2-methyl-5,6,6a,7,8,12b-hexahydrobenzo[a]phenanthridine (111 mg, 63%) as yellow solid. MS: m/z 430.6 ($M+H^+$).

Step 5

To a suspension of trans-(6a,12b)-6-benzyl-3,10,11-trimethoxy-2-methyl-5,6,6a,7,8,12b-hexahydrobenzo[a]phenanthridine (110 mg, 0.256 mmol) in EtOH/AcOH/$H_2O$ (20 mL/2 mL/1 mL) was added Pd/C (80 mg). The mixture was stirred at room temperature under $H_2$ (50 psi) for 16 hrs. The reaction mixture was filtered through a Celite pad. The filtrate was concentrated. The residue was purified by prep-HPLC to give trans-(6aR,12bS)-3,10,11-trimethoxy-2-methyl-5,6,6a,7,8,12b-hexahydrobenzo[a]phenanthridine (59 mg, 68%) as white solid. MS: m/z 340.5 ($M+H^+$).

Step 6

To a suspension of trans-(6aR,12bS)-3,10,11-trimethoxy-2-methyl-5,6,6a,7,8,12b-hexahydrobenzo[a]phenanthridine (59 mg, 0.174 mmol) in DCM (10 mL) was added $BBr_3$ (0.2 mL) under $N_2$ at −78° C. The mixture was stirred at room temperature for 16 hrs. The reaction mixture quenched by MeOH and concentrated. The residue was purified by prep-HPLC (TFA), made HCl salt by addition of 2N HCl and concentration to give HCl salt of trans-(6a,12b)-2-methyl-5,6,6a,7,8,12b-hexahydrobenzo[a]phenanthridine-3,10,11-triol (11 mg, yield: 21%) as a yellow solid. $^1$HNMR (400 MHz, DMSO-$d_6$): δ=7.25 (s, 1H), 6.83 (s, 1H), 6.74 (s, 1H), 6.69 (s, 1H), 4.33 (dd, J=22.8 Hz, 14.8 Hz, 2H), 4.09 (d, J=11.2 Hz, 1H), 3.05-2.98 (m, 1H), 2.97-2.90 (m, 1H), 2.85-2.77 (m, 1H), 2.34-2.26 (m, 1H), 2.24 (s, 3H), 1.99-1.90 (s, 1H). MS: m/z 298.1 ($M+H^+$).

Example 4: Synthesis of (6aR,12bS)-10,11-dimethoxy-2-methyl-5,6,6a,7,8,12b-hexahydrobenzo[a]phenanthridin-3-ol (Compound 4a) and (6aS,12bR)-10,11-dimethoxy-2-methyl-5,6,6a,7,8,12b-hexahydrobenzo[a]phenanthridin-3-ol (Compound 4b)

Method A

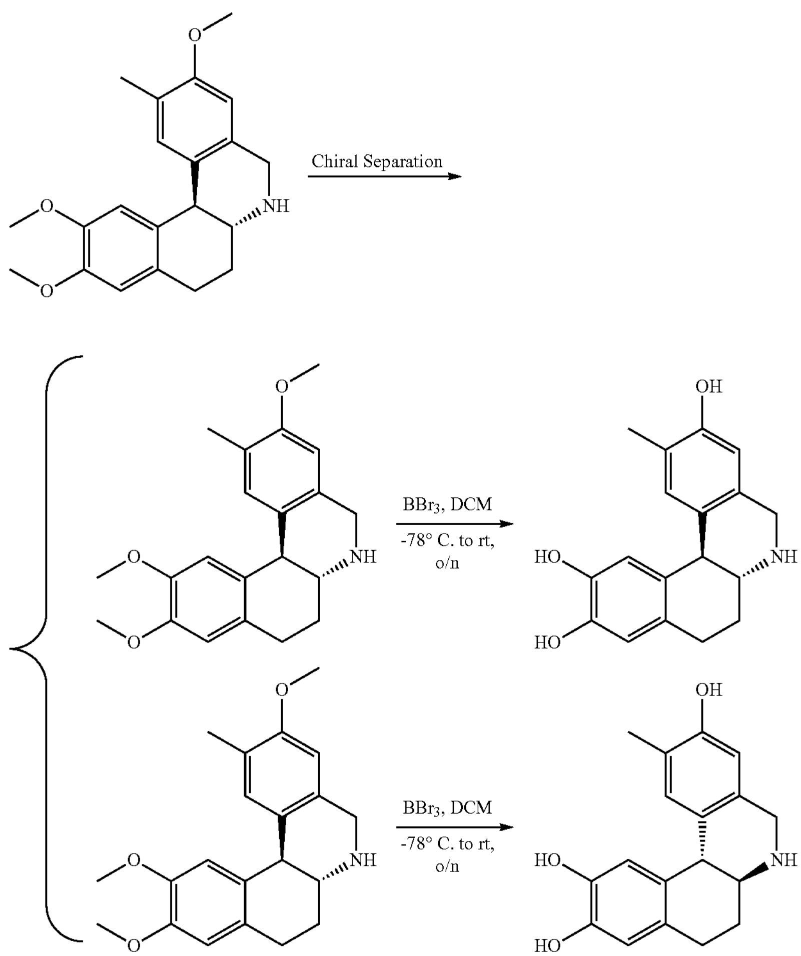

Step 1 trans-(6aR,12bS)-3,10,11-trimethoxy-2-methyl-5,6,6a,7,8,12b-hexahydrobenzo[a]phenanthridine (450 mg, 1.33 mmol) was resolved by chiral separation to give (6aR,12bS)-3,10,11-trimethoxy-2-methyl-5,6,6a,7,8,12b-hexahydrobenzo[a]phenanthridine (160 mg, yield 36%) as a white solid. $^1$HNMR (400 MHz, $CDCl_3$): δ=7.24 (s, 1H), 6.91 (s, 1H), 6.72 (s, 1H), 6.65 (s, 1H), 4.19 (s, 2H), 3.92 (d, J=10.8 Hz, 1H), 3.89 (s, 3H), 3.84 (s, 3H), 3.80 (s, 3H), 2.92-2.78 (m, 3H), 2.29-2.22 (m, 4H), 1.93-1.83 (m, 1H). ee %=98.7%.

Chiral separation also give another isomer (6aS,12bR)-3,10,11-trimethoxy-2-methyl-5,6,6a,7,8,12b-hexahydrobenzo[a]phenanthridine (180 mg, yield: 40%) as a white solid.

$^1$HNMR (400 MHz, $CDCl_3$): δ=7.22 (s, 1H), 6.91 (s, 1H), 6.71 (s, 1H), 6.68 (s, 1H), 4.08 (d, J=10.8 Hz, 1H), 3.89 (s, 3H), 3.84 (s, 3H), 3.81 (s, 3H), 2.96-2.83 (m, 3H), 2.37-2.33 (m, 2H), 2.21 (s, 3H), 2.09-2.03 (m, 2H). ee %=99.7%.

Step 2

The title compound (HCl salt) was prepared using general procedure for trans-(6a,12b)-2-methyl-5,6,6a,7,8,12b-hexahydrobenzo[a]phenanthridine-3,10,11-triol.

Meethod B

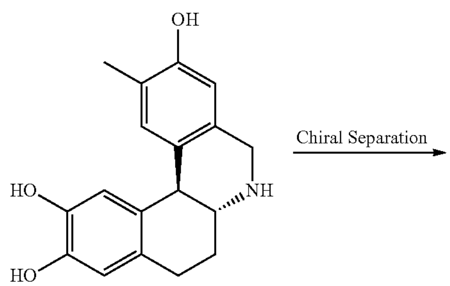

-continued

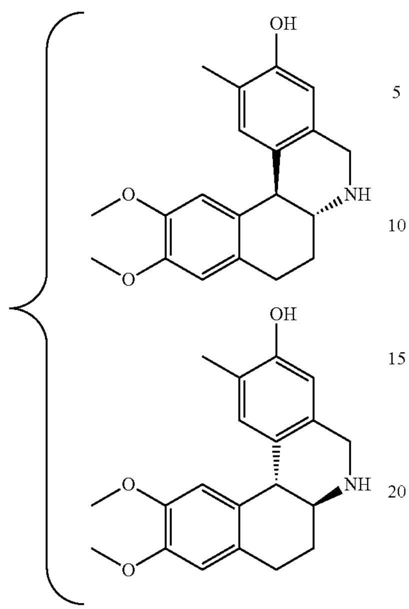

Method B:

trans-(6a,12b)-2-methyl-5,6,6a,7,8,12b-hexahydrobenzo[a]phenanthridine-3,10,11-triol (150 mg, 0.51 mmol) was resolved by chiral separation to give (6aR,12bS)-10,11-dimethoxy-2-methyl-5,6,6a,7,8,12b-hexahydrobenzo[a]phenanthridin-3-ol (25 mg, yield: 17%) as a light yellow solid. $^1$HNMR (400 MHz, $CD_3OD$): δ=7.17 (s, 1H), 6.72 (s, 1H), 6.63 (s, 1H), 6.57 (s, 1H), 4.26-4.16 (m, 2H), 3.98 (d, J=11.2 Hz, 1H), 2.93-2.78 (m, 2H), 2.73-2.66 (m, 1H), 2.21-2.07 (m, 4H), 1.94-1.81 (m, 1H). MS: m/z 298.1 $(M+H^+)$. ee %=99.1%.

Chiral separation also give another isomer (6aS,12bR)-10,11-dimethoxy-2-methyl-5,6,6a,7,8,12b-hexahydrobenzo[a]phenanthridin-3-ol (28 mg, yield: 19%) as a light yellow solid. $^1$HNMR (400 MHz, $CD_3OD$): δ=7.25 (s, 1H), 6.84 (s, 1H), 6.75 (s, 1H), 6.69 (s, 1H), 4.37-4.29 (m, 2H), 4.10 (d, J=10.8 Hz, 1H), 3.09-2.92 (m, 2H), 2.83-2.79 (m, 1H), 2.31-2.21 (m, 4H), 2.04-1.96 (m, 1H). MS: m/z 298.1 $(M+H^+)$. ee %=99.5%.

Example 5: Synthesis of Tran-(6a,12b)-5,6,6a,7,8,12b-hexahydrobenzo[a]phenanthridine-2,10,11-triol (Compound 5)

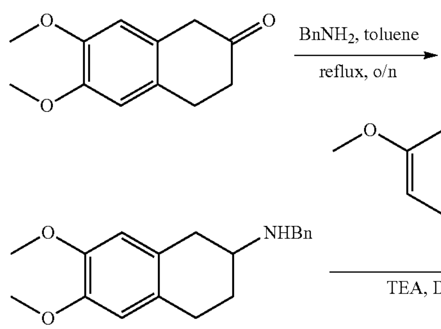

-continued

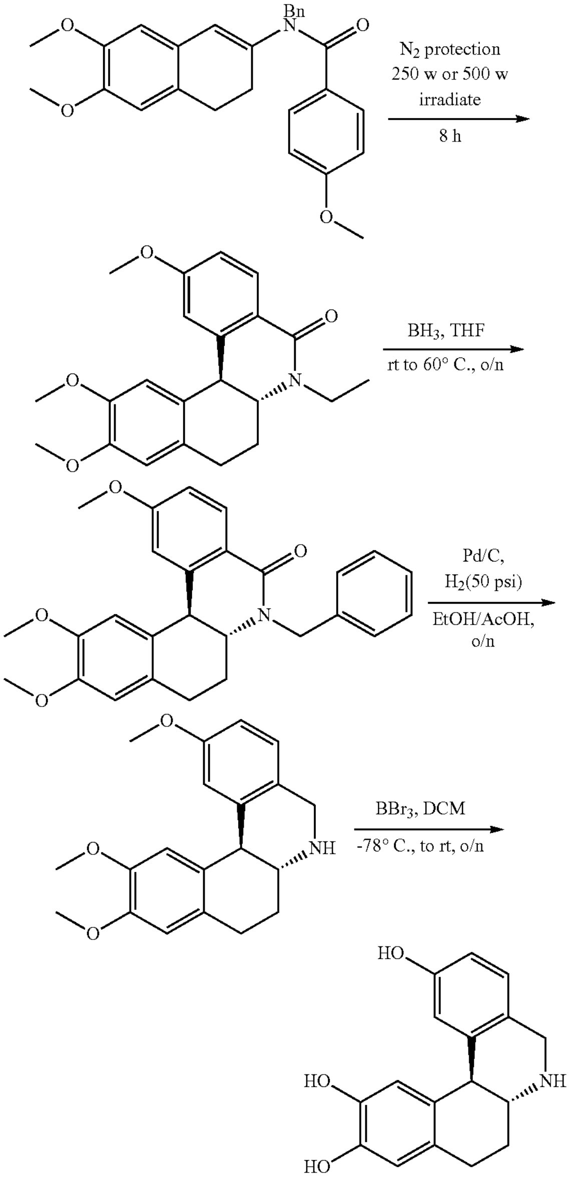

The title compound (HCl salt) was prepared using general procedure for trans-(6a,12b)-2-methyl-5,6,6a,7,8,12b-hexahydrobenzo[a]phenanthridine-3,10,11-triol. $^1$HNMR (400 MHz, $CD_3OD$): δ=7.13 (d, J=8.0 Hz, 1H), 6.75 (dd, J=8.4 Hz, 2.4 Hz, 1H), 6.64-6.59 (m, 3H), 4.28 (d, J=14.8 Hz, 1H), 4.18-4.13 (m, 2H), 4.01-3.98 (m, 1H), 2.83-2.74 (m, 2H), 2.19-2.14 (m, 1H), 1.79-1.73 (m, 1H). MS: m/z 284.1 $(M+H^+)$.

Example 6: Synthesis of Trans-(6a,12b)-5,6,6a,7,8,12b-hexahydrobenzo[a]phenanthridine-2,3,10,11-tetraol (Compound 6)

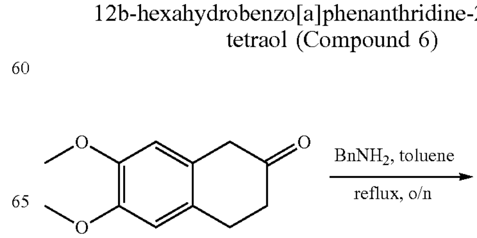

-continued

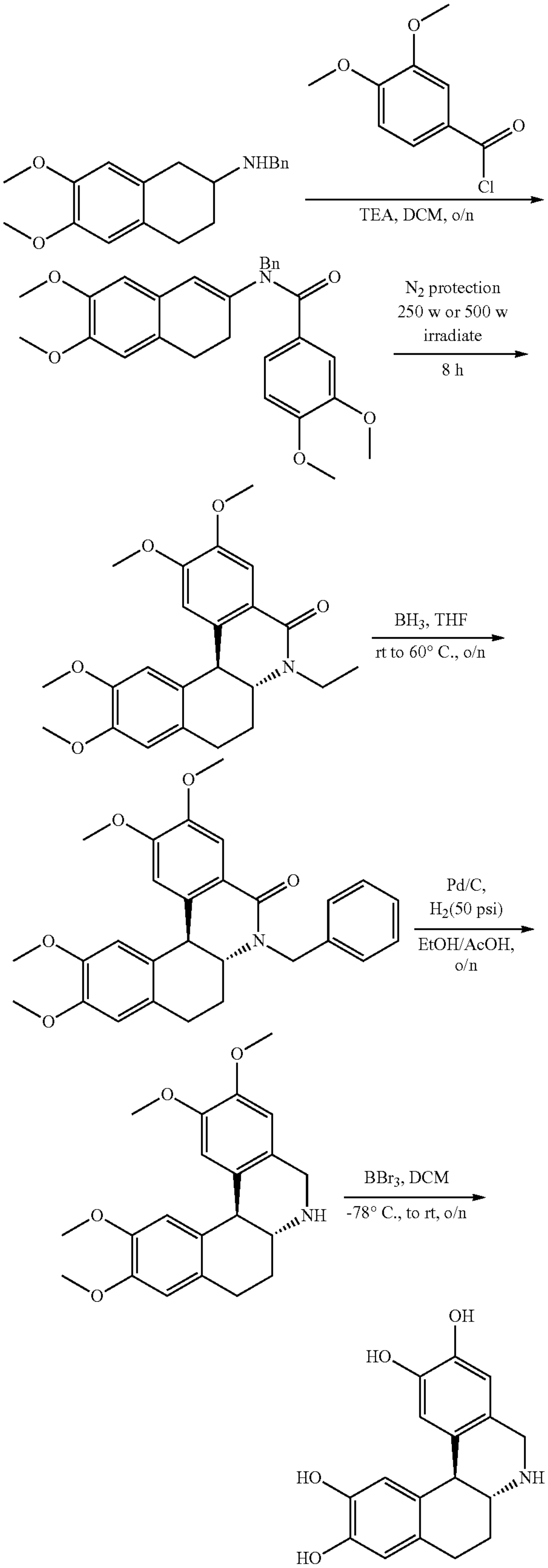

The title compound (HCl salt) was prepared using general procedure for trans-(6a,12b)-2-methyl-5,6,6a,7,8,12b-hexahydrobenzo[a]phenanthridine-3,10,11-triol. $^1$HNMR (400 MHz, $CD_3OD$): δ=6.99 (s, 1H), 6.90 (s, 1H), 6.82 (s, 1H), 6.71 (s, 1H), 4.37-4.29 (m, 2H), 4.12-4.08 (m, 1H), 3.04-2.80 (m, 3H), 2.37-2.26 (m, 1H), 2.04-1.92 (m, 1H). MS: m/z 300.1 (M+H$^+$).

Example 7: Synthesis of 4-(1,2,3,4-tetrahydro-2,6-naphthyridin-4-yl)benzene-1,2-diol (Compound 7)

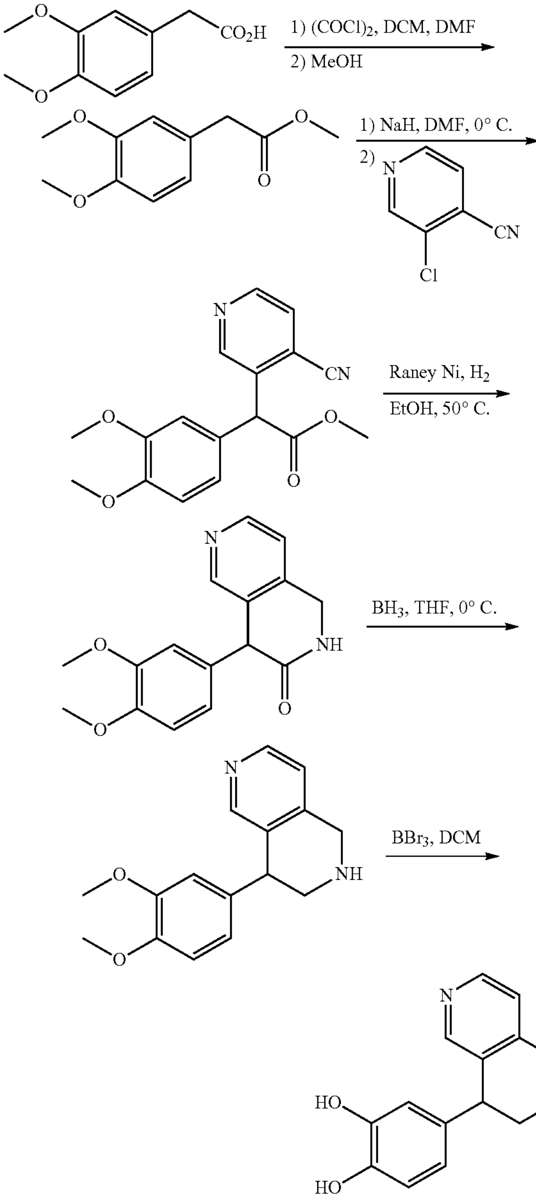

Step 1

To a solution of 2-(3,4-dimethoxyphenyl)acetic acid (10 g, 51.02 mmol) in DCM (20 mL) was added $(COCl)_2$ (17.4 mL, 204.08 mmol), DMF (1 d) and then stirred at room temperature. After 2 hrs, dry MeOH (10 mL) was added, followed by stirring at room temperature for 3 hrs. The reaction mixture was concentrated to remove solvents, and poured into $H_2O$ (100 mL) and extracted with EA (70 mL×3). The combined EA layers were washed with brine (100 mL), dried over $Na_2SO_4$ and concentrated to give methyl 2-(3,4-dimethoxyphenyl)acetate (9.13 g, yield: 86%) as a yellow oil.

Step 2

A solution of 2-(3,4-dimethoxyphenyl)acetate (2.1 g, 10 mmol) in DMF (10 mL) was added NaH (520 mg, 13 mmol) and then stirred at room temperature. After 2 hrs later, 3-chloroisonicotinonitrile (1.66 g, 12 mmol) was added, followed by stirring at 50° C. under $N_2$ overnight. The reaction mixture was poured into $H_2O$ (50 mL) and extracted with DCM (40 mL×3). The combined DCM layers were washed with brine (40 mL), dried over $Na_2SO_4$ and concentrated to dryness in vacuum. The residue was purified by silica gel column (PE/EA=1/1) to give methyl 2-(4-cyanopyridin-3-yl)-2-(3,4-dimethoxyphenyl)acetate (3.2 g, yield: >100%, crude) as a yellow oil.

Step 3

To a solution of methyl 2-(4-cyanopyridin-3-yl)-2-(3,4-dimethoxyphenyl)acetate (3.2 g, 10 mmol) in EtOH (10 mL) was added Raney Ni (1 g, 10 mmol) and then stirred at 50° C. under $H_2$ overnight. The reaction mixture was cooled to room temperature and filtered. The filtrated was concentrated to dryness in vacuum. The residue was purified by silica gel column (DCM/MeOH=20/1) to give 4-(3,4-dimethoxyphenyl)-1,2-dihydro-2,6-naphthyridin-3(4H)-one (1 g, yield: 34%, crude) as a yellow solid.

Step 4

A solution of 4-(3,4-dimethoxyphenyl)-1,2-dihydro-2,6-naphthyridin-3(4H)-one (200 mg, 0.704 mmol) in THE (4 mL) was added $BH_3$ (2.4 mL, 4.2 mmol) and then stirred at 70° C. under $N_2$ overnight. The reaction mixture was cooled to room temperature, quenched with MeOH (5 mL) and adjusted PH=2. The solution was heated to reflux for 2 hrs. After that, the reaction mixture was concentrated and poured into $NaHCO_3$ and extracted with DCM (30 mL×3). The combined DCM layers were concentrated to give 4-(3,4-dimethoxyphenyl)-1,2,3,4-tetrahydro-2,6-naphthyridine (100 mg, yield: 52%, crude) as a yellow oil.

Step 5

A solution of 4-(3,4-dimethoxyphenyl)-1,2,3,4-tetrahydro-2,6-naphthyridine (60 mg, 0.16 mmol) in DCM (3 mL) was added $BBr_3$ (0.4 mL, 0.88 mmol) and then stirred at −78° C. under $N_2$ overnight. The reaction mixture was added $NaHCO_3$ (5 mL), and adjusted PH=6 with HCl (2N). The reaction mixture was concentrated to dryness in vacuum. The residue was purified by prep-HPLC to give 4-(1,2,3,4-tetrahydro-2,6-naphthyridin-4-yl)benzene-1,2-diol (7 mg, yield: 18%) as a brown solid.

$^1$HNMR (400 MHz, $CD_3OD$): δ=8.76 (d, J=6.0 Hz, 1H), 8.34 (s, 1H), 8.10 (d, J=6.0 Hz, 1H), 6.86 (d, J=8.0 Hz, 1H), 6.81 (d, J=1.6 Hz, 1H), 6.72 (d, J=8.0 Hz, 1H), 5.02 (s, 1H), 4.84 (s, 1H), 4.66 (dd, J=10.8 Hz, J=5.6 Hz, 1H), 3.87 (dd, J=12.8 Hz, J=6.0 Hz, 1H), 3.68 (t, J=12.0 Hz, 1H). MS: m/z 243.1 (M+H$^+$).

Example 8: Synthesis of 4-(3-methyl-5,6,7,8-tetrahydro-1,7-naphthyridin-5-yl)benzene-1,2-diol (Compound 8)

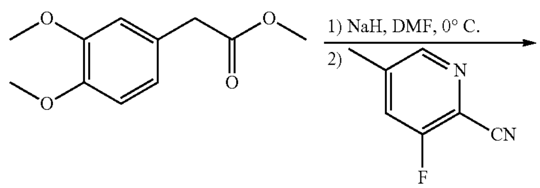

-continued

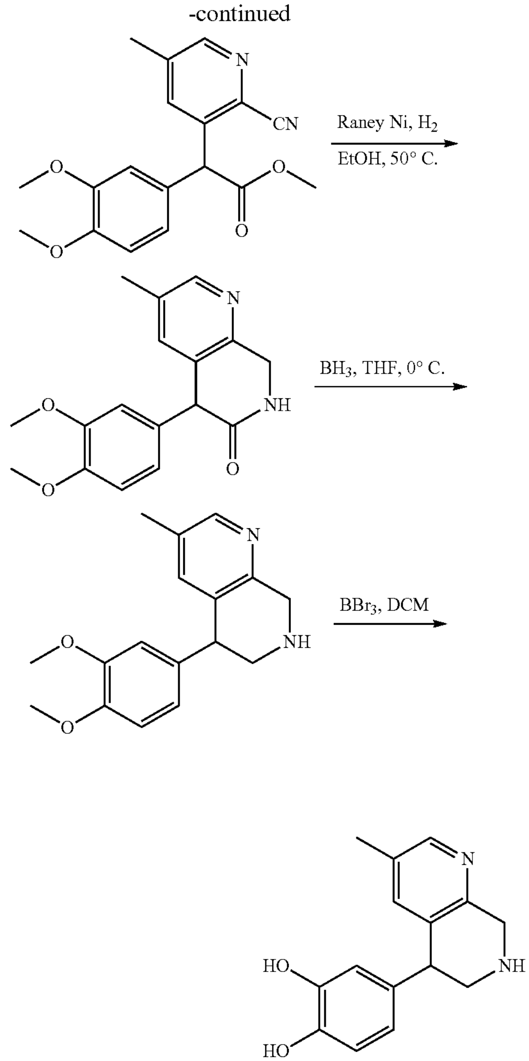

The title compound was prepared using general procedure of 4-(1,2,3,4-tetrahydro-2,6-naphthyridin-4-yl)benzene-1,2-diol.

$^1$H NMR (400 MHz, DMSO-d6): δ=9.44 (s, 1H), 9.30 (s, 1H), 8.96 (s, 1H), 8.30 (d, J=2.0 Hz, 1H), 7.04 (s, 1H), 6.73 (d, J=8.0 Hz, 1H), 6.57-6.50 (m, 2H), 4.49 (d, J=16.0 Hz, 1H), 4.30-4.22 (m, 2H), 3.64-3.60 (m, 1H), 3.34 (d, J=9.6 Hz, 1H), 2.19 (s, 3H). MS: m/z 257.1 (M+H$^+$). ($CF_3COOH$ salt).

Example 9: Synthesis of 4-(1,2,3,4-tetrahydro-2,7-naphthyridin-4-yl)benzene-1,2-diol (Compound 9)

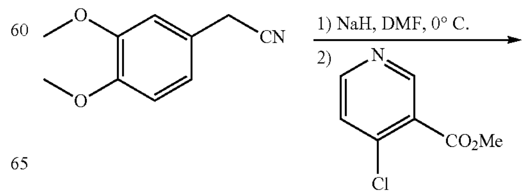

-continued

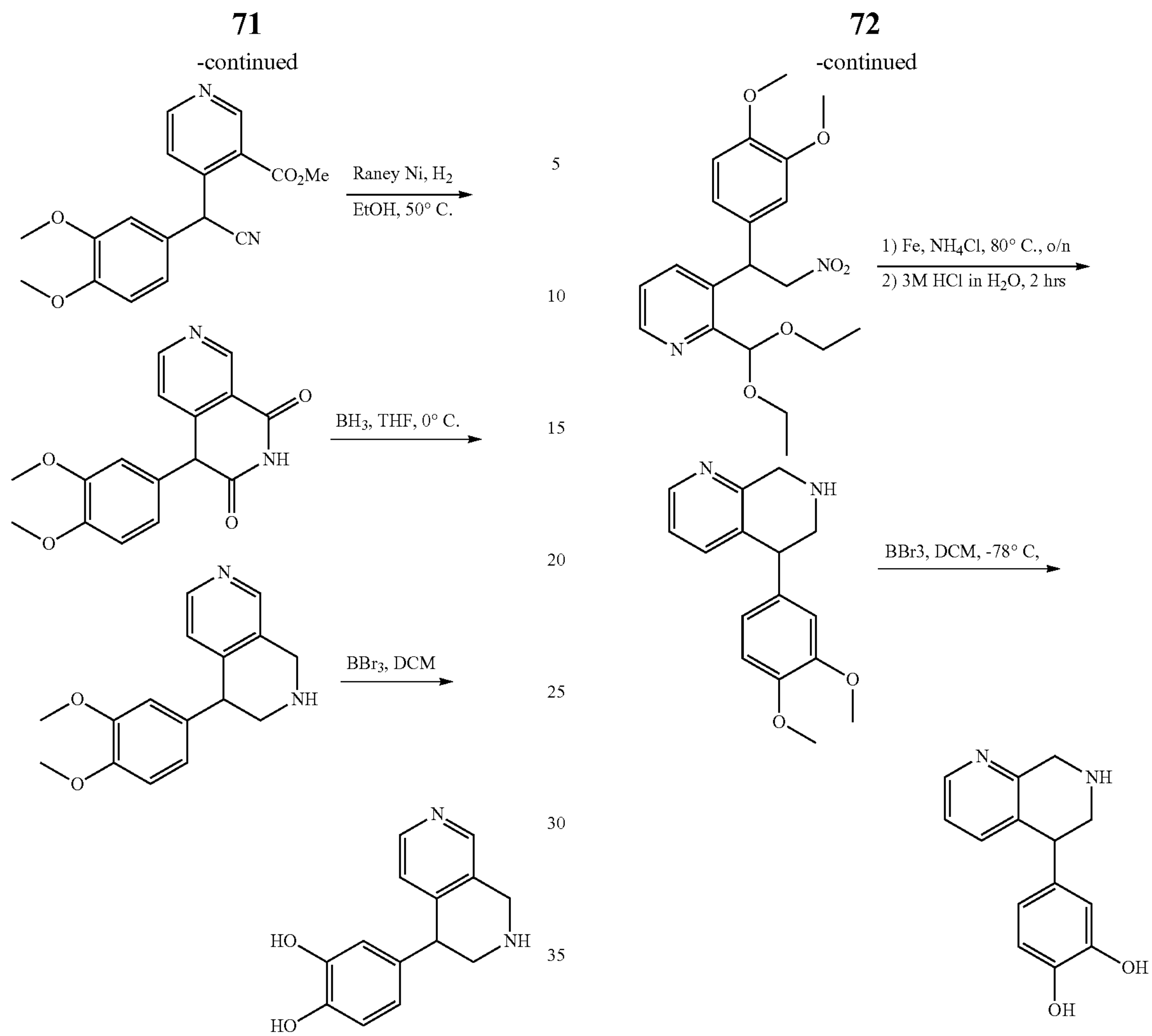

The title compound was prepared using general procedure of 4-(1,2,3,4-tetrahydro-2,6-naphthyridin-4-yl)benzene-1,2-diol. $^1$HNMR (400 MHz, $CD_3OD$): δ=8.26 (s, 1H), 8.16 (d, J=5.2 Hz, 1H), 6.86 (d, J=5.6 Hz, 1H), 6.65 (d, J=8.4 Hz, 1H), 6.46-6.41 (m, 2H), 4.17 (dd, J=23.6 Hz, J=16.4 Hz, 2H), 4.05 (dd, J=9.6 Hz, J=5.6 Hz, 1H), 3.40 (dd, J=12.8 Hz, J=6.0 Hz, 1H), 3.05 (dd, J=12.8 Hz, J=10.0 Hz, 1H). MS: m/z 243.1 (M+H$^+$).

Example 10: Synthesis of 4-(5,6,7,8-tetrahydro-1,7-naphthyridin-5-yl)benzene-1,2-diol (Compound 10)

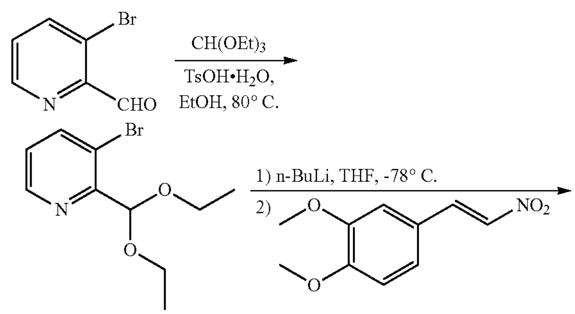

Step 1

To a solution of 3-bromopicolinaldehyde (500 mg, 2.69 mmol) in EtOH (10 mL), was added $(EtO)_3CH$ (3 mL) and p-TsOH (555 mg, 3.23 mmol). Then the mixture was stirred at 80° C. overnight. This reaction was monitored by LC-MS. The solvent was evaporated in vacuum. The reaction mixture was then diluted with $H_2O$ (10 mL), and extracted with EA (10 mL×3). Organic phase was combined, dried over anhydrous $Na_2SO_4$, and evaporated in vacuum. The residue was purified by silica column gel chromatography (PE/EA=4/1) to give 3-bromo-2-(diethoxymethyl)pyridine (531 mg, 76.2%) as a white oil. $^1$H NMR (400 MHz, DMSO-d6): δ=8.57-8.55 (m, 1H), 8.09-8.07 (m, 1H), 3.71-3.54 (m, 4H), 1.16-1.12 (m, 6H).

Step 2

To a solution of 3-bromo-2-(diethoxymethyl)pyridine (500 mg, 2.14 mmol) in THF (5 mL), was added n-BuLi (2.5 M in hexane, 0.85 mL, 2.14 mmol) dropwise in −78° C. $N_2$ atmosphere. Then, the mixture was stirred at −78° C. for 0.5 hrs. 1,2-dimethoxy-4-(2-nitrovinyl)benzene (536.7 mg, 2.57 mmol) was added. Then, the mixture was stirred at −78° C. for 2 hrs. This reaction was monitored by LC-MS. The reaction mixture was then diluted with HCl (3M in $H_2O$, 1 mL), $H_2O$ (10 mL), and extracted with EA (10 mL×3). Organic phase was combined, dried over anhydrous $Na_2SO_4$, and evaporated in vacuum. The residue was purified by flash column chromatography to give 2-(diethoxymethyl)-3-(1-(3,4-dimethoxyphenyl)-2-nitroethyl)pyridine (322.5 mg, 38.6%) as a yellow solid. $^1H$ NMR (400 MHz, DMSO-d6): δ=8.39-8.37 (m, 1H), 7.85-7.83 (m, 1H), 7.39-7.35 (m, 1H), 7.01-6.93 (m, 3H), 5.91-5.87 (m, 1H), 5.60 (s, 1H), 5.23-5.20 (m, 1H), 5.02-4.97 (m, 1H), 3.91-3.85 (m, 2H), 3.83-3.81 (m, 6H), 3.63-3.58 (m, 2H), 1.32-1.22 (m, 6H).

Step 3

To a solution of 2-(diethoxymethyl)-3-(1-(3,4-dimethoxyphenyl)-2-nitroethyl)pyridine (322.5 mg, 0.83 mmol) in EtOH (25 mL), was added Fe (186 mg, 3.32 mmol) and $NH_4Cl$ (177.6 mg, 3.32 mmol). Then, the mixture was stirred at 80° C. overnight. This reaction was monitored by LC-MS. HCl (3M in $H_2O$, 5 mL) was added. The mixture was stirred at 80° C. for 2 hrs. This reaction was monitored by LC-MS. The reaction mixture was evaporated in vacuum. The residue was purified by flash column chromatography to give 5-(3,4-dimethoxyphenyl)-5,6,7,8-tetrahydro-1,7-naphthyridine (80 mg, 8.9%) as a yellow solid.

Step 4

To a solution of 5-(3,4-dimethoxyphenyl)-5,6,7,8-tetrahydro-1,7-naphthyridine (50 mg, 0.135 mmol) in DCM (5 mL), was added $BBr_3$ (2.5 M in THF, 2 mL, 5 mmol) in −78° C. $N_2$ atmosphere. Then, the mixture was stirred at −78° C. for 2 hrs. This reaction was monitored by LC-MS. The reaction mixture was evaporated in vacuum. The residue was purified by prep-HPLC to give 4-(5,6,7,8-tetrahydro-1,7-naphthyridin-5-yl)benzene-1,2-diol (1 mg, 3.1%) as a yellow solid.

$^1H$ NMR (400 MHz, $CD_3OD$): δ=8.38 (d, J=2.2 Hz, 1H), 7.34 (d, J=3.8 Hz, 1H), 7.24-7.21 (m, 1H), 6.69 (d, J=4.0 Hz, 1H), 6.51 (s, 1H), 6.49-6.46 (m, 1H), 4.50 (d, J=8.0 Hz, 1H), 4.36-4.26 (m, 2H), 3.67-3.63 (m, 1H), 3.36 (t, J=12.8 Hz, 1H). MS: m/z 243.1 $(M+H)^+$.

Pharmaceutical Compositions

Example A-1: Parenteral Pharmaceutical Composition

To prepare a parenteral pharmaceutical composition suitable for administration by injection (e.g., subcutaneous or intravenous), 1-1000 mg of a water-soluble salt of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example A-2: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 1-1000 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 1-1000 mg of a compound described herein, or a pharmaceutically acceptable salt thereof, is placed into Size 4 capsule, or size 1 capsule (hypromellose or hard gelatin) and the capsule is closed.

BIOLOGICAL EXAMPLES

Material and Methods

Cell culture: Cells are maintained in EMEM (ATCC) containing 10% FBS. IMN/R-90 embryonic lung fibroblasts and NIH-3T3 mouse fibroblasts are purchased from ATCC. Normal Human Alveolar Epithelial Cells (NHAEpCs), Normal Human Microvascular Endothelial Cells (NHMVECs), Normal Human Lung Fibroblasts (NHLFs), and Human Dermal Fibroblasts (HDFs) are purchased from Lonza and are cultured in the proprietary media per Lonza's recommendation. Human Adult Cardiac Fibroblasts (HACFs) and Hepatic Stellate Cells (HSCs) are purchased from ScienCell and are cultured in the proprietary media per ScienCell's recommendation. Hepatocytes are purchased from Samsara and are cultured in the proprietary media per Samsara's recommendation. All additional experiments with pulmonary fibroblasts are primary human lung fibroblasts isolated by explant culture from the lungs of subjects diagnosed with IPF who underwent lung transplantation, or donors whose organs were rejected for transplantation (non-IPF), generously provided by Peter Bitterman and Craig Henke at the University of Minnesota under a protocol approved by the University of Minnesota Institutional Review Board. All primary cell culture experiments are performed with cells at passage six or less.

GPC Rome Profiling and qPCR: GPC Rome profiling is performed according to the manufacturer's suggestions (Qiagen). Cells are grown in their recommended growth media for 24 hours prior to RNA isolation using RNeasy Plus Mini Kit (Qiagen) according to manufacturer's instructions. Isolated RNA (1000 ng) are then used to synthesize cDNA using the $RT^2$ First Strand Kit (Qiagen) and the G Protein Coupled Receptors 384HT PCR Array is analyzed using a LightCycler 480 (Roche).

Cell Sorting: FACS/PBS perfused mouse lungs are finely minced with a razor blade in a 100 mm petri dish in 1 mL of cold DMEM medium containing 0.2 mg/mL-1 Liberase DL (Roche) and 100 U mL−1 DNase I (Roche). The mixture is then transferred to 15 mL tubes and incubated at 37° C. for 30 min in a water bath. Enzymatic digestion is inactivated by adding DMEM medium containing 10% fetal bovine serum. The cell suspension is passed once through a 40 m cell strainer (Fisher) to remove multicellular debris. Cells are then centrifuged at 1,300 r.p.m. at 4° C. for 10 min, washed once in PBS and resuspended in 0.2 ml of FACS buffer (1% BSA, 0.5 μM EDTA pH 7.4 in PBS). The single cell suspension is then incubated with anti-CD45-PerCp-Cy5.5, anti-CD31-PE, anti-PDGFRa-APC and anti-EpCAM-BV421 antibodies (1:200) (Biolegend) for 20 min on ice. After incubation, cells are washed with ice-cold FACS buffer and resuspended in 1 mL of FACS buffer. FACS sorting is conducted using a BD FACS Aria II (BD Biosciences). FACS-sorted epithelial cells, endothelial cells and fibroblasts are collected in 1.5 mL Eppendorf tubes containing RLT lysis buffer (Qiagen), which is subjected to mRNA extraction, complementary DNA synthesis and RT-PCR analysis. MACS/PBS perfused mouse lungs is finely minced with a razor blade in a 100 mm petri dish in 1 mL of MACs dissociation solution described in the MACS mouse lung dissociation kit. The mixture is then transferred to 15 mL tubes and incubated at 37° C. for 30 min in a water bath. Enzymatic digestion is inactivated by adding DMEM containing 10% fetal bovine serum. The cell suspension is passed once through a 40 μm cell strainer (Fisher) to remove multicellular debris. Cells are then centrifuged at 1,350 r.p.m. at 4° C. for 10 min and the supernatant is aspirated. The samples are resuspended in 0.1 ml 15% BSA-autoMACS rinsing solution. The single cell suspension is than incubated with mouse anti-CD45 MicroBeads (1:10) for 15 minutes at 4-8° C. Cells are then magnetically filtered using LS column (Miltenyi Biotec). Positively selected cells are pelleted at 1350 r.p.m at 4° C. and resuspended in RLT lysis buffer (Qiagen). Samples are then subjected to mRNA extraction, complementary DNA synthesis and RT-PCR analysis.

Immunofluorescence Microscopy: Cells are plated into 96 well plates (Corning 3603) in their specific growth media and are allowed to attach (8 hours). Media is then be exchanged for the indicated conditions for each experiment. Cells are fixed in 3.7% formalin (Sigma-Aldrich), permeabilized in 0.25% Triton X-100 (Sigma-Aldrich) and then blocked with 1% BSA for 1 h. Cells or tissue sections are incubated overnight with mouse monoclonal antibody against aSMA (Sigma-Aldrich F3777), and/or a rabbit monoclonal antibody against YAP/TAZ (Cell Signaling D24E4) diluted 1:200 in PBS with 1% BSA. Cells are then washed and exposed to flourescence-conjugated secondary antibodies (Invitrogen) diluted 1:1000 and DAPI (Thermo Fisher Scientific). Images are taken with a Cytation5 (BioTek) microscope. For scoring aSMA positive cells, an observer blinded to the treatment conditions counts aSMA-positive cells using a visual threshold for bright fibrous staining; a minimum of 200 cells is counted for each condition. YAP/TAZ localization is quantified using Gen5 (Biotek) software. Images are taken at 4× magnification of both DAPI and YAP/TAZ staining.

Traction Force Microscopy: Traction analysis is conducted. Polyacrylamide substrates with shear moduli of 6.4 kPa are prepared, and fluorescent sulfate-modified latex microspheres (0.2 m, 505/515ex/em) (FluoSpheres, Life Technologies) is conjugated to the gel surfaces after treatment with 1 mg/ml-1 of dopamine hydrochloride (Sigma-Aldrich) in 50 mM HEPES solution (pH 8.5). IPF patient derived fibroblasts are plated on the gels overnight and treated as indicated before traction force measurements. Images of gel surface-conjugated fluorescent beads are acquired for each cell before and after trypsinization using a Nikon ECLIPSE Ti microscope at 10× magnification. Traction forces is estimated by measuring bead displacement fields and computing corresponding traction fields using TractionsForAll (freely distributed program that calculates 2-D tractions exerted by an adherent cell on its substrate).

cAMP Assay: IPF patient derived fibroblasts are plated in EMEM containing 10% FBS overnight. Media is exchanged with EMEM containing 0.1% FBS for 24 hours. cAMP is measured using the cAMP-Glo™ Assay (Promega) according to manufacturer's suggestions. Twenty minutes prior to cell lysis the media is removed and cells are treated with "induction buffer" containing nonselective phosphodiesterase inhibitors and the indicated concentration of compound(s). Luminescence is measured on a Flexstation 3 (Molecular Devices) plate reader.

Western Blotting: Cells are plated in EMEM containing 10% FBS overnight. Media is exchanged with EMEM containing 0.1% FBS for 24 hours. Prior to protein isolation cells are treated with the indicated concentration of compounds for the indicated time. Total protein is isolated using RIPA buffer (pH 8.0) containing Pierce Phosphatase Inhibitor (Thermo) and Halt Protease Inhibitor Cocktail (Thermo). Lysate total protein concentration are determined using Pierce BCA Protein Assay Kit (Thermo) and samples are run on a 10% polyacrylamide gel. Blots are incubated overnight with primary antibodies: pYAP (Ser 127, Cell Signaling D9W21), YAP/TAZ (Cell Signaling D24E4), GAPDH (Cell Signaling 14C10), HSC70 (Santa Cruz sc-7298), aSMA (Abcam ab5694), and fibronectin (Santa Cruz sc-9068) diluted 1:1000 in Li-Cor Odyssey Blocking Buffer. Blots are washed with TBS-Tween before 60 minute incubation with IR-dye-conjugated secondary antibodies (Li-Cor) diluted 1:10,000. Plates are imaged via a Li-Cor OdysseyXL system with quantification performed via densitometry.

Immuno-ECM: Adapting from previously published methods, IPF patient-derived fibroblasts are plated to confluence in clear-bottom 96-well plates. After cells attached, the medium is swapped for EMEM containing 0.1% FBS±2 ng/mL TGF-β. After 48 hrs the indicated concentration of DHX or DMSO control is added to each well and incubated for 24 hrs. WST-1 viability reagent is added to each well (Sigma-Aldrich) and measured on a Flexstation 3 (Molecular Devices) plate reader. Cells are then fixed in 3.7% formalin (Sigma-Aldrich), and permeabilized in 0.25% Triton X-100 (Sigma-Aldrich). Wells are next washed with tris-buffered saline (TBS) and blocked with Li-Cor Odyssey Blocking Buffer for 60 minutes before overnight incubation in a polyclonal rabbit antibody for fibronectin (Sigma sc-9068) or collagen I (Novus NB600-408) diluted 1:200 in blocking buffer. Wells are washed with TBS-Tween before 45 minute incubation with IR-dye-conjugated secondary antibody (Li-Cor #926-32211) diluted 1:400. Plates are imaged via a Li-Cor OdysseyXL system with quantification performed via densitometry. Data is expressed as IR intensity relative to WST-1 signal absorbance in order to account for any potential compound toxicity.

Matrix Remodeling Measured by Atomic Force Microscopy: NIH-3T3 cells are plated to confluence onto gelatin coated (Cell Biologics) AFM compatible tissue culture dishes (Willco) in DMEM containing 10% FBS. After cells attached overnight, media is replaced with DMEM containing 2% FBS, 2 ng/mL TGFf3, and 20 μg/mL ascorbic acid to promote matrix deposition. After 72 hrs, measurements are made using a BioScope Catalyst AFM (Bruker, MA, USA). Microindentations are performed using a 2.5 μm radius sphere-tipped probe (Novascan, IA, USA) with a spring constant determined at ~100 pN nm-1 by thermal fluctuation method. For each dish, 3 different areas are analyzed. Force curves are acquired with MIRO 2.0 (NanoScope 9.1; Bruker) at an indentation rate of 20 μm s−1 and a ramp size of 10 m on different points. The Young's modulus E is determined by the fitting of force curve by Hertz model using NanoScope Analysis software (Bruker) and considering Poisson's ratio of 0.5. Media is next exchanged for fresh DMEM containing 2% FBS, 2 ng/mL TGFf3, and 20 μg/mL ascorbic acid with the indicated concentration of DHX or 0.1% DMSO (vehicle control). After another 72 hrs, AFM measurements are made as before. The resulting cell-derived matrix is decellularized with Phosphate-buffered saline (Gibco) containing: 0.5% (v/v) Triton X-100 (Sigma-Aldrich) and 20 mM $NH_4OH$ (LabChem Inc.). Matrices are washed 3× with PBS and then plated with low passage (P3), NHLFs for 24 hrs prior to RNA isolation.

RNA Interference: Cells are transfected using Lipofectamine RNAiMAX (Life Technologies) with 25 nM siGENOME siRNA SMARTpool (Dharmacon) targeting DRD1 (L-005477-00-0005) or a nontargeting SMARTpool (D-001810-10-05). Cells are cultured for 72 hrs before collecting RNA. For the YAP/TAZ localization experiments, the cells are transfected in their 6-well plates for 48 hrs prior to re-plating into 96-well plates for the immunofluorescence assays.

Bleomvcin Mouse Study: In the initial in vivo siRNA study, adult male age-matched C57BL/6N mice at 6-8 weeks of age are purchased from the National Cancer Institute (NCI)-Frederick Mouse Repository (Frederick, MD, USA). All experiments are performed in accordance with National Institute of Health guidelines and protocols approved by the Massachusetts General Hospital Subcommittee on Research Animal Care, and maintained all mice in a specific pathogen-free (SPF) environment certified by the American Association for Accreditation of Laboratory Animal Care (AAALAC). 6-8 weeks old mice were anesthetized with ketamine and xylazine before exposure of the trachea. Lung fibrosis is induced by intratracheal injection of bleomycin (50 μL at 1.2 U/kg) or phosphate buffered saline (PBS; as control) on day 0. After 14 days, small interfering RNA (siRNA) duplexes targeting mouse YAP (L-046247-01-0005) or TAZ (L-058248-01-0005) mRNA (Dharmacon) or nontargeting control siRNA are administered in vivo by intratracheal instillation at a single dose of 25 μg (each siRNA) per mouse. On day 21, mice were sacrificed and lungs harvested for collagen determination and biochemical analyses. To obtain BAL samples for total protein concentration determination, lungs were lavaged with six 0.5-mL aliquots of PBS. BAL samples were centrifuged at 3,000 g for 20 min at 4° C. and the supernatants is transferred to siliconized low-binding Eppendorf tubes (PGC Scientifics) for subsequent analysis. Total protein concentration of the BAL fluid was determined by BCA Protein Assay Kit (Pierce).

Histological Scoring: Five μm thick sections are cut from Paraffin embedded lung tissues, and the sections were stained either with hematoxylin and eosin (H&E) or with Masson's Trichrome stain kit (Abcam). All H&E-stained slides and trichrome-stained slides were reviewed in a blinded fashion by a thoracic pathologist. The severity of interstitial and peribronchiolar lung immature and mature fibrosis was estimated on a numerical scale according to Ashcroft et al. For scoring purposes, all H&E stained slides were systematically scanned at 100× magnification and successive 100× fields were be scored. Scoring was based on the following scale: 0 (no fibrosis), 1 (minimal interstitial and/or peribronchiolar thickening due to fibrosis), 3 (moderate thickening without obvious architectural distortion), 5 (increased fibrosis with formation of fibrous bands and/or small masses), 7 (severe architectural distortion with large areas of fibrosis and areas of honeycomb changes), and 8 (total fibrous obliteration of the field). Liver trichrome stained sections were computationally measured using Image J software. After converting each image in an RGB stack, the threshold was adjusted and kept at the same level for all the images.

Hydroxyproline: Hydroxyproline content was measured using a hydroxyproline assay kit (Biovision) according to the manufacture's instruction. The lung tissues was weighed, homogenized in sterile water (10 mg of tissue per 100 μL $H_2O$) and hydrolyzed in 12N HCl in a pressure-tight, Teflon-capped vial at 120° C. for 3 hrs followed by filtration through a 45 m Spin-X® Centrifuge Tube filter (Corning). Ten μL of the hydrolyzed samples were dried in a Speed-Vac for 2 hrs, followed by incubation with 100 μL of Chloramine T reagent for 5 minutes at room temperature and 100 μL of 4-(Dimethylamino) benzaldehyde (DMAB) for 90 minutes at 60° C. The absorbance of oxidized hydroxyproline was determined at 560 nm. Hydroxyproline concentrations were calculated from a standard curve generated using known concentrations of trans-4-hydroxyl-L-proline. The total amount of protein isolated from the weighed tissues was determined by using a protein assay kit (Bio-Rad, absorbance at 595 nm). The amount of collagen was expressed in g/mg total protein.

Figure 2:
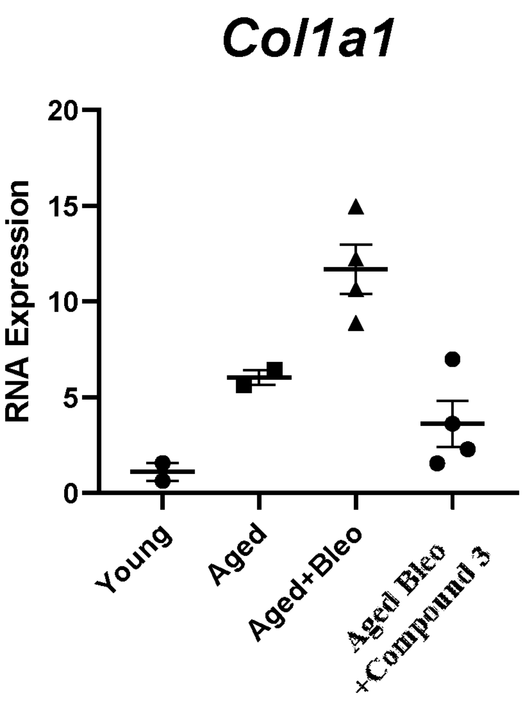
FIG. 2 shows that Compound 3 at a concentration of 10 μM inhibits expression of Col1a1 in precision cut lung slices cultured for 3 days in 24 months aged mice injured with bleomycin.

Representative data obtained for Compound 3 and Compound 4a is shown in FIGS. 1 and 2.

As shown in FIG. 1, Compound 3 (left) and Compound 4a (right) selectively inhibit YAP/TAZ nuclear localization in human lung fibroblasts and not in human alveolar epithelial cells.

As shown in FIG. 2, Compound 3 inhibits expression of Col1a1 in precision cut lung slices cultured for 3 days from aged mice (24 months) injured with bleomycin. (10 μM Compound 3).

Example B-1: Enzyme Assay of Inhibition of YAP/TAZ and DR1

Representative data for exemplary compounds disclosed herein is presented in Table 4.

TABLE 4

| Name | YAP/TAZ $IC_{50}$ (μM) | DR1 $EC_{50}$ (μM) |
|---|---|---|
| (6aR,12bR)-5,6,6a,7,8,12b-hexahydrobenzo[a]phenanthridine-3,4,10,11-tetraol | B | — |
| (6aR,12bS)-5,6,6a,7,8,12b-hexahydrobenzo[a]phenanthridine-3,4,10,11-tetraol | B | — |
| (6aR,12bS)-5,6,6a,7,8,12b-hexahydrobenzo[a]phenanthridine-2,10,11-triol | B | A |
| (6aS,12bR)-2-methyl-5,6,6a,7,8,12b-hexahydrobenzo[a]phenanthridine-3,10,11-triol | B | A |
| 4-(1,2,3,4-tetrahydro-2,7-naphthyridin-4-yl)benzene-1,2-diol | B | — |
| 4-(6-methyl-1,2,3,4-tetrahydro-2,7-naphthyridin-4-yl)benzene-1,2-diol | B | — |
| 4-(1,2,3,4-tetrahydro-2,6-naphthyridin-4-yl)benzene-1,2-diol | B | — |
| 4-(5,6,7,8-tetrahydro-1,7-naphthyridin-5-yl)benzene-1,2-diol | B | A |
| 3-chloro-5-(3a,4,5,6,7,7a-hexahydrothieno[2,3-c]pyridin-4-yl)benzene-1,2-diol | B | A |
| 4-(3-chloro-4,5-dimethoxyphenyl)-3a,4,5,6,7,7a-hexahydrothieno[2,3-c]pyridine | B | B |
| 4-((4S)-3-propyl-3a,4,5,6,7,7a-hexahydrothieno[2,3-c]pyridine-4-yl)benzene-1,2-diol | B | B |
| 4-((4R)-3-propyl-3a,4,5,6,7,7a-hexahydrothieno[2,3-c]pyridine-4-yl)benzene-1,2-diol | B | B |
| 3-chloro-5-(3a,4,5,6,7,7a-hexahydrothieno[2,3-c]pyridin-4-yl)-2-methoxyphenol | B | B |
| 4-(3,4-dimethoxyphenyl)-3-propyl-3a,4,5,6,7,7a-hexahydrothieno[2,3-c]pyridine | B | B |
| 4-(3-propyl-3a,4,5,6,7,7a-hexahydrothieno[2,3-c]pyridine-4-yl)benzene-1,2-diol | B | B |

TABLE 4-continued

| Name | YAP/TAZ $IC_{50}$ (μM) | DR1 $EC_{50}$ (μM) |
|---|---|---|
| 4-((4S)-3a,4,5,6,7,7a-hexahydrothieno[2,3-c] pyridine-4-yl)benzene-1,2-diol | B | A |
| 4-((4R)-3a,4,5,6,7,7a-hexahydrothieno[2,3-c] pyridine-4-yl)benzene-1,2-diol | B | A |
| 4-(6-methyl-3a,4,5,6,7,7a-hexahydrothieno[2,3-c] pyridine-4-yl)benzene-1,2-diol | B | B |
| 4-(3,4-dimethoxyphenyl)-3a,4,5,6,7,7a-hexahydrothieno[2,3-c]pyridine | B | B |

A: $IC_{50}/EC_{50}$ is ≤ 1 μM
B: $IC_{50}/EC_{50}$ is > 1 μM and ≤ 20 μM; and
C: $IC_{50}/EC_{50}$ > 20 μM (a compound that is active).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the structure of Formula (I), or a pharmaceutically acceptable salt or solvate thereof:

Formula (I)

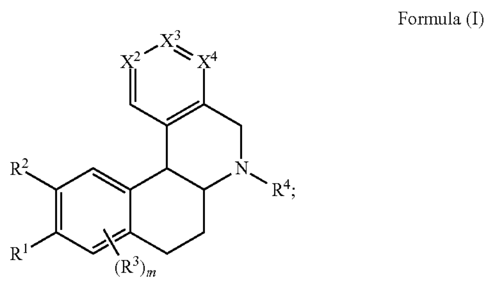

wherein:

$X^2$ is N or $CR^5$;
$X^3$ is N or $CR^6$;
$X^4$ is $CR^7$;
m is 0, 1, or 2;
$R^1$ is halogen, —OH, —$OR^a$, or $C_1$-$C_6$ alkyl;
$R^2$ is —OH, —$OR^a$, or $C_1$-$C_6$ alkyl,
$R^3$ is halogen, —CN, —OH, —$OR^a$, or $C_1$-$C_6$ alkyl;
$R^4$ is hydrogen or $C_1$-$C_6$ alkyl;
i) $R^5$ is hydrogen, halogen, —CN, —OH, —$OR^a$, or $C_1$-$C_6$ alkyl;
$R^6$ is —OH, or —$OR^a$; and
$R^7$ is —OH, or —$OR^a$, or
ii) $R^5$ is —OH, or —$OR^a$;
$R^6$ is —OH, or —$OR^a$; and
$R^7$ is hydrogen, halogen, —CN, —OH, —$OR^a$, or $C_1$-$C_6$ alkyl; and
each $R^a$ is independently $C_1$-$C_6$ alkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each $C_1$-$C_6$ alkyl, cycloalkyl, heterocycloalkyl, aryl, and heteroaryl is independently unsubstituted or substituted with one, two, or three halogen, —OH, $C_1$-$C_6$ alkyl, or $C_1$-$C_6$ haloalkyl.

2. The compound of claim 1, or a pharmaceutically acceptable salt or solvate thereof, wherein:
$R^1$ is —OH, or —$OR^a$.

3. The compound of claim 1, or a pharmaceutically acceptable salt or solvate thereof, wherein:
$R^2$ is —OH, or —$OR^a$.

4. The compound of claim 1, or a pharmaceutically acceptable salt or solvate thereof, wherein:
each $R^1$ and $R^2$ is —OH.

5. The compound of claim 1, or a pharmaceutically acceptable salt or solvate thereof, wherein:
$X^2$ is $CR^5$;
$X^3$ is $CR^6$; and
$X^4$ is $CR^7$.

6. The compound of claim 1, or a pharmaceutically acceptable salt or solvate thereof, wherein:
$R^5$ is hydrogen;
$R^6$ is —OH, or —$OR^a$; and
$R^7$ is, —OH, or —$OR^a$.

7. The compound of claim 6, or a pharmaceutically acceptable salt or solvate thereof, wherein:
$R^5$ is hydrogen;
$R^6$ is —OH; and
$R^7$ is —OH.

8. The compound of claim 1, or a pharmaceutically acceptable salt or solvate thereof, wherein:
$R^5$ is —OH, or —$OR^a$;
$R^6$ is —OH, or —$OR^a$; and
$R^7$ is hydrogen.

9. The compound of claim 8, or a pharmaceutically acceptable salt or solvate thereof, wherein:
$R^5$ is —OH;
$R^6$ is —OH; and
$R^7$ is hydrogen.

10. The compound of claim 1, or a pharmaceutically acceptable salt or solvate thereof, wherein:
$R^3$ is halogen, —OH, —$OR^a$, or $C_1$-$C_6$ alkyl.

11. The compound of claim 1, or a pharmaceutically acceptable salt or solvate thereof, wherein the compound of Formula (I) has the structure of Formula (III):

Formula (III-2)

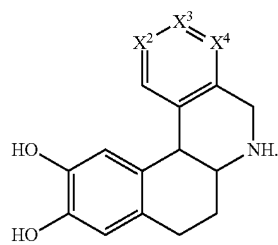

12. The compound of claim 1, or a pharmaceutically acceptable salt or solvate thereof, wherein the compound is:

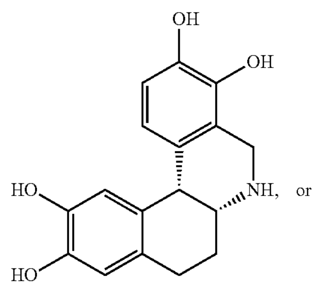
or

-continued

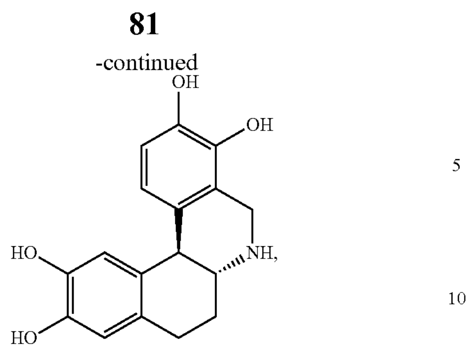

or a pharmaceutically acceptable salt or solvate thereof.

13. A pharmaceutical composition comprising a compound of claim 1, or a pharmaceutically acceptable salt or solvate thereof, and one or more pharmaceutically acceptable excipients.

14. The pharmaceutical composition of claim 13, wherein the pharmaceutical composition is formulated for administration to a mammal by intravenous administration, subcutaneous administration, oral administration, inhalation, nasal administration, dermal administration, or ophthalmic administration.

* * * * *